United States Patent
Neumann et al.

(10) Patent No.: US 12,412,668 B2
(45) Date of Patent: Sep. 9, 2025

(54) INTERPRETABLE INDEX SCORE FOR COMBINING MULTIMODAL METRICS FOR REMOTE MONITORING OF CONDITION PROGRESSION

(71) Applicant: Modality.AI, Inc., San Francisco, CA (US)

(72) Inventors: Michael Neumann, Winterbach (DE); Hardik Kothare, Burlingame, CA (US); Vikram Ramanarayanan, San Francisco, CA (US)

(73) Assignee: Modality.AI, Inc., San Francisco, CA (US)

( * ) Notice: Subject to any disclaimer, the term of this patent is extended or adjusted under 35 U.S.C. 154(b) by 0 days.

(21) Appl. No.: 18/810,490

(22) Filed: Aug. 20, 2024

(65) Prior Publication Data
US 2025/0253060 A1    Aug. 7, 2025

Related U.S. Application Data

(60) Provisional application No. 63/551,060, filed on Feb. 7, 2024.

(51) Int. Cl.
*G16H 50/70* (2018.01)
*A61B 5/00* (2006.01)

(52) U.S. Cl.
CPC ........... *G16H 50/70* (2018.01); *A61B 5/4842* (2013.01)

(58) Field of Classification Search
CPC ............................. G16H 50/70; A61B 5/4842
See application file for complete search history.

(56) References Cited

U.S. PATENT DOCUMENTS

| | | | | |
|---|---|---|---|---|
| 2008/0294692 | A1* | 11/2008 | Angell | G16H 50/70 |
| 2015/0380009 | A1* | 12/2015 | Chang | A61B 5/4076 |
| | | | | 704/263 |
| 2018/0107791 | A1* | 4/2018 | Guo | G06Q 40/08 |
| 2019/0153056 | A1* | 5/2019 | Shneider | A61K 45/06 |
| 2020/0349859 | A1* | 11/2020 | Shah | G06F 3/016 |
| 2021/0215610 | A1* | 7/2021 | Robertson | G16H 10/40 |

(Continued)

OTHER PUBLICATIONS

Lian Haijuan, et al., Early prediction of cerebral-cardiac syndrome after ischemic stroke: the PANSCAN scale, Jul. 8, 2020, BMC Neurology (Year: 2020).*

(Continued)

*Primary Examiner* — Sun M Li
(74) *Attorney, Agent, or Firm* — Sikander M Khan

(57) ABSTRACT

A computer-implemented method of generating interpretable, composite marker indexes that are discriminative and noise-robust is provided. The method comprises storing remotely collected multimodal digital markers from a first cohort and a second cohort. The method further comprises grouping multicollinear features in the multimodal digital markers into clusters, and then selecting representative features for the clusters for multiple classification tasks that require discrimination between the first cohort and the second cohort. The method further comprises linearly combining the representative features into an interpretable, composite marker index such that relative contributions of each of the representative features to the interpretable, composite marker index are known.

20 Claims, 30 Drawing Sheets

(56) References Cited

U.S. PATENT DOCUMENTS

2022/0241353 A1* 8/2022 Landau ............... A23L 29/219
2024/0194339 A1* 6/2024 Nassiri ............... G16H 50/20

OTHER PUBLICATIONS

Bohn L, Drouin SM, McFall GP, Rolfson DB, Andrew MK, Dixon RA. Machine learning analyses identify multi-modal frailty factors that selectively discriminate four cohorts in the Alzheimer's disease spectrum: a COMPASS-ND study. BMC Geriatr. Dec. 11, 2023; 23(1):837. doi: 10.1186/s12877-023-04546-1. (Year: 2023).*

Tritt A, Yue JK, Ferguson AR, Torres Espin A, Nelson LD, Yuh EL, Markowitz AJ, Manley GT, Bouchard KE; TRACK-TBI Investigators. Data-driven distillation and precision prognosis in traumatic brain injury with interpretable machine learning. Sci Rep. Dec. 1, 2023;13(1):21200. doi: 10.1038/s41598-023-48054 (Year: 2023).*

M. Neumann, O. Roesler, J. Liscombe, H. Kothare, D. Suendermann Oeft, D. Pautler, I. Navar, A. Anvar, J. Kumm, R. Norel, E. Fraenkel, A. V. Sherman, J. D. Berry, G. L. Pattee, J. Wang, J. R. Green, V. Ramanarayanan, Investigating the Utility of Multimodal Conversational Technology and Audiovisual Analytic Measures for the Assessment and Monitoring of Amyotrophic Lateral Sclerosis at Scale, in: Proc. Interspeech 2021, 2021, pp. 4783-4787, 5 pages.

M. Proudfoot, A. Jones, K. Talbot, A. Al-Chalabi, M. R. Turner, The ALSFRS as an outcome measure in therapeutic trials and its relationship to symptom onset, Amyotrophic Lateral Sclerosis and Frontotemporal Degeneration 17 (5-6) (2016) 414-425, 13 pages.

M. S. Pepe and M. L. Thompson, "Combining diagnostic test results to increase accuracy," Biostatistics, vol. 1, No. 2, pp. 123-140, 2000.

O. Roesler, H. Kothare, W. Burke, M. Neumann, J. Liscombe, A. Cornish, D. Habberstad, D. Pautler, D. Suendermann-Oeft, V. Ramanarayanan, Exploring Facial Metric Normalization for Within- and Between-Subject Comparisons in a Multimodal Health Monitoring Agent, in: Companion Publication of the 2022 International Conference on Multimodal Interaction, ICMI '22 Companion, Association for Computing Machinery, New York, NY, USA, 2022, p. 160-165, 8 pages.

P. Boersma, Praat, a system for doing phonetics by computer, Glot International 5 (9/10) (2001) 341-345, 8 pages.

P. J. Curran, K. Obeidat, D. Losardo, Twelve frequently asked questions about growth curve modeling, Journal of Cognition and Development 11 (2) (2010) pp. 121-136.

P. Rong, Y. Yunusova, M. Eshghi, H. P. Rowe, J. R. Green, A Speech Measure for Early Stratification of Fast and Slow Progressors of Bulbar Amyotrophic Lateral Sclerosis: Lip Movement Jitter, Amyotrophic Lateral Sclerosis and Frontotemporal Degeneration 21 (1-2) (2020) 34-4, 17 pages.

P. Virtanen, R. Gommers, T. E. Oliphant, M. Haberland, T. Reddy, D. Cournapeau, E. Burovski, P. Peterson, W. Weckesser, J. Bright et al., "Scipy 1.0: fundamental algorithms for scientific computing in python," Nature methods, vol. 17, No. 3, pp. 261-272, 202.

R. Aznar-Gimeno, L. M. Esteban, R. del Hoyo-Alonso, A. Borque-Fernando, and G. Sanz, "A stepwise algorithm for linearly combining biomarkers under Youden index maximization," Mathematics, vol. 10, No. 8, p. 1221, 2022.

R. Kueffner, N. Zach, M. Bronfeld, R. Norel, N. Atassi, V. Balagurusamy, B. Di Camillo, A. Chio, M. Cudkowicz, D. Dillenberger et al., "Stratification of amyotrophic lateral sclerosis patients: a crowdsourcing approach," Scientific reports, vol. 9, No. 1, p. 690, 2019.

R. Norel, M. Pietrowicz, C. Agurto, S. Rishoni, G. Cecchi, Detection of Amyotrophic Lateral Sclerosis (ALS) via Acoustic Analysis, in: Proc. Interspeech 2018, 2018, pp. 377-381, 5 pages.

S. Schneider, A. Baevski, R. Collobert, M. Auli, wav2vec: Unsupervised pre-training for speech recognition, (2019) 9 pages.

S. Van Der Walt, S. C. Colbert, G. Varoquaux, The NumPy Array: A Structure for Efficient Numerical Computation, Computing in Science & Engineering 13 (2) (2011) 22-30, 9 pages.

T. E. Oliphant, "Python for scientific computing," Computing in science & engineering, vol. 9, No. 3, pp. 10-20, 2007.

T. J. Moore, J. Heyward, G. Anderson, G. C. Alexander, Variation in the estimated costs of pivotal clinical benefit trials supporting the US approval of new therapeutic agents, 2015-2017: a cross-sectional study, BMJ open 10 (6) (2020) 5 pages.

T. Sing, O. Sander, N. Beerenwinkel, T. Lengauer, ROCR: Visualizing Classifier Performance in R, Bioinformatics 21 (20) (2005) 7881, 2 pages.

V. Bazarevsky, Y. Kartynnik, A. Vakunov, K. Raveendran, M. Grundmann, BlazeFace: Sub-millisecond Neural Face Detection on Mobile GPUs, CoRR abs/1907.05047 (2019), 4 pages.

V. Boschi, E. Catricala, M. Consonni, C. Chesi, A. Moro, and S. F. Cappa, "Connected speech in neurodegenerative language disorders: a review," Frontiers in psychology, vol. 8, p. 269, 2017, 21 pages.

V. Ramanarayanan, A. C. Lammert, H. P. Rowe, T. F. Quatieri, and J. R. Green, "Speech as a biomarker: opportunities, interpretability, and challenges," Perspectives of the ASHA Special Interest Groups, vol. 7, No. 1, pp. 276-283, 2022, 8 pages.

V. Ramanarayanan, D. Pautler, L. Arbatti, A. Hosamath, M. Neumann, H. Kothare, O. Roesler, J. Liscombe, A. Cornish, D. Habberstad, V. Richter, D. Fox, D. Suendermann-Oeft, I. Shoulson, When Words Speak Just as Loudly as Actions: Virtual Agent Based Remote Health Assessment Integrating What Patients Say with What They Do, in: Proc. Interspeech, 2023, pp. 678-679.

V. Richter, M. Neumann, H. Kothare, O. Roesler, J. Liscombe, D. Suendermann-Oeft, S. Prokop, A. Khan, C. Yavorsky, J.-P. Lindenmayer, V. Ramanarayanan, Towards multimodal dialog-based speech & facial biomarkers of schizophrenia, in: Companion Publication of the 2022 International Conference on Multimodal Interaction, ICMI'22 Companion, Association for Computing Machinery, New York, NY, USA, 2022, p. 171-176.

W. J. Youden, "Index for rating diagnostic tests," Cancer, vol. 3, No. 1, pp. 32-35, 1950.

W. McKinney et al., "Data structures for statistical computing in python," in Proceedings of the 9th Python in Science Conference, vol. 445, No. 1. Austin, TX, 2010, pp. 51-56.

W. Yu and T. Park, "Two simple algorithms on linear combination of multiple biomarkers to maximize partial area under the ROC curve," Computational Statistics & Data Analysis, vol. 88, pp. 15-27, 2015.

W.-N. Hsu, B. Bolte, Y.-H. H. Tsai, K. Lakhotia, R. Salakhutdinov, A. Mohamed, Hubert: Self-supervised speech representation learning by masked prediction of hidden units, IEEE/ACM Transactions on Audio, Speech, and Language Processing 29 (2021) 3451-3460, 10 pages.

X. Robin, N. Turck, A. Hainard, N. Tiberti, F. Lisacek, J.-C. Sanchez, and M. Muller, "pROC: an open-source package for r "and s+ to analyze and compare ROC curves," BMC Bioinformatics, vol. 12, p. 77, 2011.

Y. A. Reshef, D. N. Reshef, H. K. Finucane, P. C. Sabeti, and M. Mitzenmacher, "Measuring dependence powerfully and equitably," The Journal of Machine Learning Research, vol. 17, No. 1, pp. 7406-7468, 2016, 63 pages.

Y. Kartynnik, A. Ablavatski, I. Grishchenko, M. Grundmann, Real-time Facial Surface Geometry from Monocular Video on Mobile GPUs, CoRR abs/1907.06724 (2019), 4 pages.

Y. Yunusova, J. R. Green, M. J. Lindstrom, G. L. Pattee, L. Zinman, Speech in ALS: Longitudinal Changes in Lips and Jaw Movements and Vowel Acoustics, Journal of Medical Speech-Language Pathology 21 (1) (2013), 20 pages.

Y. Yunusova, J. R. Green, M. J. Lindstrom, L. J. Ball, G. L. Pattee, L. Zinman, Kinematics of disease progression in bulbar ALS, Journal of Communication Disorders 43 (1) (2010) 6-20, 21 pages.

Y. Yunusova, N. L. Graham, S. Shellikeri, K. Phuong, M. Kulkarni, E. Rochon, D. F. Tang-Wai, T. W. Chow, S. E. Black, L. H. Zinman, et al., Profiling speech and pausing in amyotrophic lateral sclerosis (ALS) and frontotemporal dementia (FTD), PLOS ONE 11 (1) (2016), 18 pages.

J. Robin, J. E. Harrison, L. D. Kaufman, F. Rudzicz, W. Simpson, M. Yancheva, Evaluation of Speech-Based Digital Biomarkers: Review and Recommendations, Digital Biomarkers 4 (3) (2020) 99-108, 10 pages.

(56) References Cited

OTHER PUBLICATIONS

J. W. van Unnik, M. Meyjes, M. R. J. van Mantgem, L. H. van den Berg, R. P. van Eijk, Remote monitoring of amyotrophic lateral sclerosis using wearable sensors detects differences in disease progression and survival: a prospective cohort study, Ebiomedicine 103 (2024) 13 pages.
L. J. Haverkamp, V. Appel, S. H. Appel, Natural history of amyotrophic lateral sclerosis in a database population validation of a scoring system and a model for survival prediction, Brain 118 (3) (1995) 707-719, 13 pages.
R. Dubbioso, M. Spisto, L. Verde, V. V. Iuzzolino, G. Senerchia, G. De Pietro, I. De Falco, G. Sannino, Precision medicine in ALS: Identification of new acoustic markers for dysarthria severity assessment, Biomedical Signal Processing and Control 89 (2024) 105706, 10 pages.
A. Baevski, Y. Zhou, A. Mohamed, M. Auli, wav2vec 2.0: A framework for self-supervised learning of speech representations, Advances in neural information processing systems 33 (2020) 12449-12460, 12 pages.
A. Bandini, J. R. Green, B. Taati, S. Orlandi, L. Zinman, Y. Yunusova, Automatic Detection of Amyotrophic Lateral Sclerosis (ALS) From Video-Based Analysis of Facial Movements: Speech and Non-speech Tasks, in: 2018 13th IEEE International Conference on Automatic Face & Gesture Recognition (FG 2018), IEEE, 2018, pp. 150-157, 8 pages.
A. Bansal and M. Sullivan Pepe, "When does combining markers improve classification performance and what are implications for practice?" Statistics in medicine, vol. 32, No. 11, pp. 1877-1892, 2013, 24 pages.
A. E. McGlothlin, R. J. Lewis, Minimal clinically important difference: Defining what really matters to patients, JAMA 312 (13) (2014) 1342-1343, 2 pages.
A. G. Copay, B. R. Subach, S. D. Glassman, D. W. Polly Jr, T. C. Schuler, Understanding the minimum clinically important difference: a review of concepts and methods, The Spine Journal 7 (5) (2007) pp. 541-546.
A. K. Silbergleit, A. F. Johnson, and B. H. Jacobson, "Acoustic analysis of voice in individuals with amyotrophic lateral sclerosis and perceptually normal vocal quality," Journal of Voice, vol. 11, No. 2, pp. 222-231, 1997.
B. Tomik and R. J. Guiloff, "Dysarthria in amyotrophic lateral sclerosis: A review," Amyotrophic Lateral Sclerosis, vol. 11, No. 1-2, pp. 4-15, 2010.
C. Agurto, M. Pietrowicz, E. K. Eyigoz, E. Mosmiller, E. Baxi, J. D. Rothstein, P. Roy, J. Berry, N. J. Maragakis, O. Ahmad, G. A. Cecchi, R. Norel, Analyzing Progression of Motor and Speech Impairment in ALS, in: 2019 41st Annual International Conference of the IEEE Engineering in Medicine and Biology Society (EMBC), 2019, pp. 6097-6102.
C. Barnett, J. R. Green, R. Marzouqah, K. L. Stipancic, J. D. Berry, L. Korngut, A. Genge, C. Shoesmith, H. Briemberg, A. Abrahao, et al., Reliability and validity of speech & pause measures during passage reading in ALS, Amyotrophic Lateral Sclerosis and Frontotemporal Degeneration 21 (1-2) (2020) 42-50.
C. N. Fournier, R. Bedlack, C. Quinn, J. Russell, D. Beckwith, K. H.Kaminski, W. Tyor, V. Hertzberg, V. James, M. Polak, et al., Development and Validation of the Rasch-Built Overall Amyotrophic Lateral Sclerosis Disability Scale (Roads), Jama Neurology 77 (4) (2020) 480-488.
D. Albanese, S. Riccadonna, C. Donati, and P. Franceschi, "A practical tool for maximal information coefficient analysis," GigaScience, vol. 7, No. 4, p. giy032, 2018, 8 pages.
D. Ienco and R. Meo, "Exploration and reduction of the feature space by hierarchical clustering," in Proceedings of the 2008 siam international conference on data mining. SIAM, 2008, pp. 577-587.
D. L. Guarin, B. Taati, A. Abrahao, L. Zinman, Y. Yunusova, Video based facial movement analysis in the assessment of bulbar amyotrophic lateral sclerosis: clinical validation, Journal of Speech, Language, and Hearing Research 65 (12) (2022) 4667-4678.
D. M. Low, K. H. Bentley, and S. S. Ghosh, "Automated assessment of psychiatric disorders using speech: A systematic review," Laryngoscope investigative otolaryngology, vol. 5, No. 1, pp. 96-116, 2020, 21 pages.
D. Ramamoorthy, K. Severson, S. Ghosh, K. Sachs, J. D. Glass, C. Fournier, A. Sherman, T. M. Herrington, J. Berry, E. Fraenkel, Identifying patterns in amyotrophic lateral sclerosis progression from sparse longitudinal data, Nature Computational Science 2 (9) (2022) 605-616, 23 pages.
D. Suendermann-Oeft, A. Robinson, A. Cornish, D. Habberstad, D. Pautler, D. Schnelle-Walka, F. Haller, J. Liscombe, M. Neumann, M. Merrill, et al., Nemsi: A Multimodal Dialog System for Screening of Neurological or Mental Conditions, in: Proceedings of the 19th ACM International Conference on Intelligent Virtual Agents, 2019, pp. 245-247.
D. Von Rosen, The growth curve model: a review, Communications in Statistics—Theory and Methods 20 (9) (1991) 2791-2822.
E. G. Baxi, T. Thompson, J. Li, J. A. Kaye, R. G. Lim, J. Wu, D. Ramamoorthy, L. Lima, V. Vaibhav, A. Matlock et al., "Answer ALS, a large-scale resource for sporadic and familial ALS combining clinical and multi-omics data from induced pluripotent cell lines," Nature neuroscience, pp. 1-12, 2022.
F. Pedregosa, G. Varoquaux, A. Gramfort, V. Michel, B. Thirion, O. Grisel, M. Blondel, P. Prettenhofer, R. Weiss, V. Dubourg et al., "Scikit-learn: Machine learning in python," the Journal of machine Learning research, vol. 12, pp. 2825-2830, 2011.
G. M. Stegmann, S. Hahn, J. Liss, J. Shefner, S. Rutkove, K. Shelton, C. J. Duncan, V. Berisha, Early detection and tracking of bulbar changes in ALS via frequent and remote speech analysis, NPJ Digital Medicine 3 (1) (2020) 132, 5 pages.
H. C. de Vet, C. B. Terwee, R. W. Ostelo, H. Beckerman, D. L. Knol, L. M. Bouter, Minimal changes in health status questionnaires: distinction between minimally detectable change and minimally important change, Health and Quality of Life Outcomes 4 (2006) 1-5 pages.
H. Kothare, M. Neumann, J. Liscombe, J. Green, V. Ramanarayanan, Responsiveness, Sensitivity and Clinical Utility of Timing Related Speech Biomarkers for Remote Monitoring of ALS Disease Progression, in: Proc. Interspeech, 2023, pp. 2323-2327, 5 pages.
H. Kothare, M. Neumann, J. Liscombe, O. Roesler, D. Habberstad, W. Burke, A. Cornish, L. Arbatti, A. Hosamath, D. Fox, et al., Assessment of atypical speech in multiple sclerosis via a multimodal dialogue platform: An exploratory study, in: Proceedings of the 8th International Conference on Speech Motor Control (SMC), 2022.
H. Kothare, M. Neumann, J. Liscombe, O. Roesler, W. Burke, A. Exner, S. Snyder, A. Cornish, D. Habberstad, D. Pautler, et al., Statistical and clinical utility of multimodal dialogue-based speech and facial metrics for Parkinson's disease assessment, Proc. Interspeech 2022 (2022) 3658-3662, 5 pages.
H. Kothare, V. Ramanarayanan, O. Roesler, M. Neumann, J. Liscombe, W. Burke, A. Cornish, D. Habberstad, B. Kopald, A. Bai, et al., Atypical speech acoustics and jaw kinematics during affect production in children with autism spectrum disorder assessed by an interactive multi-modal conversational platform, in: Proceedings of the 8th International Conference on Speech Motor Control (SMC), 2022.
H. P. Rowe, S. E. Gutz, M. F. Maffei, and J. R. Green, "Acoustic based articulatory phenotypes of amyotrophic lateral sclerosis and parkinson's disease: Towards an interpretable, hypothesis-driven framework of motor control." in Interspeech, 2020, pp. 4816-4820.
H. P. Rowe, S. Shellikeri, Y. Yunusova, K. V. Chenausky, and J. R. Green, "Quantifying articulatory impairments in neurodegenerative motor diseases: A scoping review and meta-analysis of interpretable acoustic features," International Journal of Speech Language Pathology, pp. 1-14, 2022.
H. Wickham, ggplot2: Elegant Graphics for Data Analysis, Springer Verlag New York, 2016.
J. Cohen, V. Richter, M. Neumann, D. Black, A. Haq, J. Wright Berryman, V. Ramanarayanan, A multimodal dialog approach to mental state characterization in clinically depressed, anxious, and suicidal populations, Frontiers in psychology 14 (2023), 17 Pages.
J. D. Hunter, Matplotlib: A 2D Graphics Environment, Computing in Science & Engineering 9 (3) (2007) 90-95, 6 pages.

(56) References Cited

OTHER PUBLICATIONS

J. Liscombe, M. Neumann, H. Kothare, O. Roesler, D. Suendermann Oeft, V. Ramanarayanan, On timing and pronunciation metrics for intelligibility assessment in pathological ALS speech, in: vol. 27: Suppl. (2022): Abstracts 8th International Conference on Speech Motor Control Groningen, Aug. 2022, 1 page.

J. M. Cedarbaum, N. Stambler, E. Malta, C. Fuller, D. Hilt, B. Thurmond, A. Nakanishi, B. A. S. Group, A. complete listing of the BDNF Study Group, et al., The ALSFRS-R: a revised ALS functional rating scale that incorporates assessments of respiratory function, Journal of the Neurological Sciences 169 (1-2) (1999) 13-21, 9 pages.

J. Pinheiro, D. Bates, R Core Team, nlme: Linear and Nonlinear Mixed Effects Models, r package version 3.1-164 (2023), 339 pages.

J. Q. Su and J. S. Liu, "Linear combinations of multiple diagnostic markers," Journal of the American Statistical Association, vol. 88, No. 424, pp. 1350-1355, 1993.

J. R. Green, D. R. Beukelman, L. J. Ball, Algorithmic estimation of pauses in extended speech samples of dysarthric and typical speech, Journal of Medical Speech-Language Pathology 12 (4) (2004) 149, 9 pages.

J. R. Green, Y. Yunusova, M. S. Kuruvilla, J. Wang, G. L. Pattee, L. Synhorst, L. Zinman, J. D. Berry, Bulbar and speech motor assessment in ALS: Challenges and future directions, Amyotrophic Lateral Sclerosis and Frontotemporal Degeneration 14 (7-8) (2013) 494-500, 8 pages.

K. L. Stipancic, Y. Yunusova, J. D. Berry, J. R. Green, Minimally detectable change and minimal clinically important difference of a decline in sentence intelligibility and speaking rate for individuals with amyotrophic lateral sclerosis, Journal of Speech, Language, and Hearing Research 61 (11) (2018) 2757-2771, 15 pages.

K. M. Allison, Y. Yunusova, T. F. Campbell, J. Wang, J. D. Berry, and J. R. Green, "The diagnostic utility of patient-report and speech-language pathologists' ratings for detecting the early onset of bulbar symptoms due to als," Amyotrophic Lateral Sclerosis and Frontotemporal Degeneration, vol. 18, No. 5-6, pp. 358-366, 2017.

K. Yorkston, D. Beukelman, R. Tice, Sentence intelligibility test, Lincoln, NE: Tice Technologies (1996), 34 pages.

L. C. Wijesekera, P. Nigel Leigh, Amyotrophic lateral sclerosis, Orphanet Journal of Rare Diseases 4 (2009) 1-22, 22 pages.

L. E. Simmatis, J. Robin, T. Pomm'ee, S. Mckinlay, R. Sran, N. Taati, J. Truong, B. Koyani, Y. Yunusova, Validation of automated pipeline for the assessment of a motor speech disorder in amyotrophic lateral sclerosis (ALS), Digital Health 9 (2023).

L. Kang, A. Liu, and L. Tian, "Linear combination methods to improve diagnostic/prognostic accuracy on future observations," Statistical methods in medical research, vol. 25, No. 4, pp. 1359-1380, 2016, 22 pages.

L. Xu, T. Liu, L. Liu, X. Yao, L. Chen, D. Fan, S. Zhan, S. Wang, Global variation in prevalence and incidence of amyotrophic lateral sclerosis: A systematic review and meta-analysis, Journal of Neurology 267 (2020), 944-953, 10 pages.

M. Eshghi, Y. Yunusova, K. P. Connaghan, B. J. Perry, M. F. Maffei, J. D. Berry, L. Zinman, S. Kalra, L. Korngut, A. Genge, et al., Rate of speech decline in individuals with amyotrophic lateral sclerosis, Scientific Reports 12 (1) (2022) 15713, 14 pages.

M. McAuliffe, M. Socolof, S. Mihuc, M. Wagner, M. Sonderegger, Montreal Forced Aligner: Trainable Text-Speech Alignment Using Kaldi, in: Proc. Interspeech, 2017, pp. 498-502. doi: 10.21437/Interspeech.2017-1386, 5 pages.

M. Milling, F. B. Pokorny, K. D. Bartl-Pokorny, B. W. Schuller, Is Speech the New Blood? Recent Progress in AI-Based Disease Detection From Audio in a Nutshell, Frontiers in Digital Health 4 (2022) 7 pages.

\* cited by examiner

```
batch_size = tf.shape(x)[0]

x = self.rescale(x)

patches = self.extract_patches(x)

x = self.patch_proj(patches)

class_emb = tf.broadcast_to(
    self.class_emb, [batch_size, 1, self.d_model]
)

x = tf.concat([class_emb, x], axis=1)

x = x + self.pos_emb for layer in self.enc_layers:
    x = layer(x, training)

return self.mlp_head(x[:, 0])
```

Figure 10

|  | F | M | Age (years) | #Sess. | ALSFRS-R Baseline | ALSFRS-R speech BL | #Sessions per participant | Time span first-to-last (days) |
|---|---|---|---|---|---|---|---|---|
| Bulbar onset | 18 | 18 | 61.6 (11.9) | 598 | 38.5; 35.9 (6.1) | 3.0; 2.7 (0.8) | 16.6 (19.4) | 232.8 (222.2) |
| Non-bulbar onset | 52 | 55 | 59.9 (9.6) | 2,790 | 38.0; 35.6 (7.4) | 4.0; 3.6 (0.6) | 26.1 (25.0) | 377.5 (305.1) |
| All pALS | 70 | 73 | 60.4 (10.2) | 3,388 | 38.0; 36.4 (7.2) | 4.0; 3.4 (0.8) | 23.7 (24.7) | 341.1 (292.6) |
| Healthy controls | 71 | 64 | 59.9 (10.3) | 3,428 | - | - | 25.4 (24.5) | 317.7 (262.6) |

Table 1: Participant statistics. F: number of female participants. M: number of male participants. BL: baseline (first session). The time span *first-to-last* is the mean number of days between participants' first and last session in the data collection. The large variation of the number of samples per participant in this data collection is due to the continuous and ongoing recruitment of new participants in this study. Statistics are reported as *median; mean (standard deviation)* for ALSFRS-R scores, and as *mean (standard deviation)* otherwise.

Figure 13

Table 2: Overview of extracted metrics. For visual metrics, functionals (minimum, maximum, average) are applied to produce one value across all video frames of an utterance. Visual distance metrics are measured in pixels and are normalized by dividing them by the intercanthal distance (distance between inner corners of the eyes) for each participant. *specific to DDK task

| | Domain | Exemplar Metrics |
|---|---|---|
| Audio | Energy | shimmer (%), intensity (dB), signal-to-noise ratio (dB) |
| | Timing | speaking and articulation duration (sec.), articulation and speaking rate (WPM), percent pause time (PPT, %), canonical timing agreement (CTA, %), cycle-to-cycle temporal variability* (cTV, sec.), syllable rate* (syl./sec.), number of syllables* |
| | Voice quality | cepstral peak prominence (CPP, dB), harmonics-to-noise ratio (HNR, dB) |
| | Frequency | mean, max., min. fundamental frequency F0 (Hz), first three formants F1, F2, F3 (Hz), slope of 2nd formant (Hz/sec.), jitter (%) |
| Text | Lexico-semantic | word count, percentage of content words, noun rate, verb rate, pronoun rate, noun-to-verb ratio, noun-to-pronoun ratio, closed class word ratio, idea density |
| Video | Mouth (distances) | lip aperture/opening, lip width, mouth surface area, mean symmetry ratio between left and right half of the mouth |
| | Lip/Jaw Movement | velocity, acceleration, jerk, and speed of lower lip and jaw center |
| | Eyes | number of eye blinks per sec., eye opening, vertical distance placement of eyebrows |

Figure 15

Table 3: Feature clusters from hierarchical clustering and the selected representative features. *AUC* represents the mean AUC for distinguishing bulbar onset and non-bulbar onset pALS samples across five cross validation folds. Only features with AUC> 0.65 were included in the longitudinal analyses. *Resp. p* are the p-values of the responsiveness analysis (see Table 4) and an asterisk (*) indicates features that showed signal in the sensitivity analysis.
LL: lower lip, JC: jaw center, RP: reading passage, DDK: diadochokinesis, PD: picture description, SBC: single breath counting, SIT: sentence intelligibility test.

| Cluster description | Selected representative | AUC | Resp. p |
|---|---|---|---|
| Timing: duration and rates | Speaking duration (RP) | 0.84 | 0.0001* |
| Temporal DDK measures | cTV (DDK) | 0.83 | |
| Timing alignment | CTA (RP) | 0.83 | 0.0020* |
| Duration and word count for PD | Word count (PD) | 0.83 | < 0.0001* |
| Eyebrow displacement | Max. eyebrow displ. (SIT) | 0.78 | |
| Pause time | PPT (SIT) | 0.77 | 0.0001 |
| Lip width | Max. lip width (RP) | 0.72 | 0.0490 |
| Voice quality (read/free speech) | HNR (SIT) | 0.71 | 0.0020 |
| Cepstral peak prominence (CPP) | CPP (RP) | 0.69 | 0.0280* |
| Voice quality for SBC and DDK | HNR (DDK) | 0.68 | 0.0010 |
| Lip aperture, mouth surface area | Mean lip aperture (SIT) | 0.68 | |
| Eye opening measures | Max. eye opening (SIT) | 0.68 | |
| Content and closed class words | Closed class word ratio (PD) | 0.67 | |
| Min. and mean F0 | Mean F0 (RP) | 0.67 | 0.0351 |
| JC velocity for SIT | Max. JC velocity down (SIT) | 0.66 | |
| Duration measures for SBC and DDK | Number of syllables (DDK) | 0.65 | |
| JC velocity for RP | Max. JC velocity up (RP) | 0.65 | |
| Verb/noun/pronoun rates | Pronoun rate (PD) | 0.62 | |
| LL velocity for PD | Max. LL jerk up (PD) | 0.61 | |
| JC velocity for PD | Max. JC velocity down (PD) | 0.61 | |
| JC velocity for SBC | Mean JC speed (SBC) | 0.60 | |
| Max. F0 and F0 stdev. | Max. F0 (SIT) | 0.60 | |
| LL velocity for read speech | Mean LL speed (SIT) | 0.58 | |
| JC velocity for DDK | Max. JC velocity down (DDK) | 0.58 | |
| LL velocity for DDK | Mean LL jerk (DDK) | 0.57 | |
| LL velocity for SBC | Max. LL speed (SBC) | 0.55 | |
| Mouth symmetry ratio | Mean mouth symmetry ratio (RP) | 0.54 | |

Figure 17

Table 4: Responsiveness of metrics. Bulbar onset: n = 36 (598 sessions). Non-Bulbar onset: n = 107 (2700 sessions)

| Metric | MCID | Onset | Slope ± standard error of slope per week | Standard error (SE) of the mean | Weeks to detect change > SE | Weeks to detect change > MCID |
|---|---|---|---|---|---|---|
| RP CTA (%) | 0.60 | Bulbar | -0.2010 ± 0.0408 | 0.48 | 2.34 | 3.28 |
| | | Non-Bulbar | -0.0750 ± 0.0185 | 0.23 | 3.07 | 8.8 |
| PD word count (words) | 2.5 | Bulbar | -0.2447 ± 0.1286 | 1.26 | 6.88 | 10.92 |
| | | Non-Bulbar | 0.2851 ± 0.0873 | 0.93 | 3.26 | 8.77 |
| RP speaking duration (seconds) | 1.46 | Bulbar | 0.3196 ± 0.0854 | 0.67 | 2.11 | 4.56 |
| | | Non-Bulbar | 0.0617 ± 0.0110 | 0.31 | 5.02 | 23.5 |
| RP mean F0 (Hz) | 1.02 | Bulbar | 0.1576 ± 0.0403 | 1.48 | 9.39 | 11.55 |
| | | Non-Bulbar | 0.0662 ± 0.0181 | 0.67 | 10.12 | 27.40 |
| DDK HNR (dB) | 0.41 | Bulbar | 0.0264 ± 0.0068 | 0.15 | 5.68 | 16.07 |
| | | Non-Bulbar | 0.0059 ± 0.0031 | 0.06 | 15.28 | 112.82 |
| RP CPP (dB) | 0.41 | Bulbar | 0.0157 ± 0.0034 | 0.13 | 9.40 | 29.00 |
| | | Non-Bulbar | 0.0120 ± 0.0024 | 0.06 | 3.93 | 34.5 |
| RP Max. lip width | 0.01 | Bulbar | 0.0002 ± 0.0002 | 0.0030 | 38.5 | 100 |
| | | Non-Bulbar | 0.0003 ± 0.0001 | 0.0020 | 8.75 | 34 |
| SIT PPT (s) | 0.66 | Bulbar | 0.0003 ± 0.0042 | 0.23 | 30.59 | 252.26 |
| | | Non-Bulbar | 0.0157 ± 0.0055 | 0.07 | 5.05 | 30.59 |
| SIT HNR (dB) | 0.39 | Bulbar | 0.0017 ± 0.0025 | 0.16 | 20.41 | 247.06 |

Figure 18

Table 5: Sensitivity of metrics. 47 pALS (793 sessions), 135 controls (3428 sessions). Controls had a slope significantly different from 0 for metrics with an asterisk (*) next to them. pALS had a slope significantly different from controls for metrics with two asterisks (**) next to their p-value of difference.

| Metric | p-value of difference | Cohort | Intercept ± standard error | Slope ± standard error |
|---|---|---|---|---|
| RP speaking duration* (seconds) | < 0.0001** | Controls | 34.55 ± 0.87 | -0.0368 ± 0.0101 |
| | | pALS | 44.96 ± 1.88 | 0.1153 ± 0.0220 |
| RP CTA* (%) | 0.0017** | Controls | 79.92 ± 0.85 | -0.0084 ± 0.0113 |
| | | pALS | 66.81 ± 1.83 | -0.1130 ± 0.0238 |
| PD word count* (words) | 0.0071** | Controls | 100.63 ± 4.47 | 0.6204 ± 0.0602 |
| | | pALS | 70.94 ± 9.72 | 0.2355 ± 0.1430 |
| RP CPP (dB) | 0.0341** | Controls | 25.64 ± 0.21 | -0.0055 ± 0.0029 |
| | | pALS | 27.37 ± 0.47 | 0.0073 ± 0.0060 |
| DDK HNR (dB) | 0.1047 | Controls | 7.11 ± 0.23 | 0.0055 ± 0.0033 |
| | | pALS | 9.62 ± 0.49 | 0.0171 ± 0.0071 |
| SIT PPT (%) | 0.1594 | Controls | 1.66 ± 0.34 | -0.0036 ± 0.0040 |
| | | pALS | 4.71 ± 0.73 | 0.0083 ± 0.0084 |
| RP mean F0* (Hz) | 0.1885 | Controls | 147.23 ± 3.09 | 0.0417 ± 0.0188 |
| | | pALS | 156.85 ± 6.33 | 0.1007 ± 0.0449 |
| SIT HNR (dB) | 0.2657 | Controls | 10.01 ± 0.22 | -0.0002 ± 0.0025 |
| | | pALS | 12.10 ± 0.47 | 0.0059 ± 0.0055 |
| RP Max. lip width (Hz) | 0.0014 | Controls | 1.65 ± 0.01 | -0.0001 ± 0.0001 |
| | | pALS | 1.69 ± 0.03 | -0.0001 ± 0.0003 |

Figure 19

Table 1: Overview of extracted metrics, feature clusters and selected representative features. For visual metrics, functionals (minimum, maximum, average) are applied to produce one value across all video frames of an utterance. Visual distance metrics are measured in pixels and are normalized by dividing them by the intercanthal distance (distance between inner corners of the eyes) for each subject. *the text metric word count for the picture description task was clustered together with timing related audio features. TRR: test-retest reliability, LL: lower lip, JC: jaw center, RP: reading passage, PD: picture description, DDK: diadochokinesis

|  | Metrics | Feature cluster | Selected representative | TRR |
|---|---|---|---|---|
| Audio | shimmer (%), harmonics-to-noise ratio (HNR, dB), jitter (%) | Voice quality | HNR (DDK) | 0.81 |
|  | speaking and articulation duration (sec.)*, articulation and speaking rate (WPM) | Duration & Rate | speaking duration (RP) | 0.95 |
|  | mean, max., min. stdev. of fundamental frequency F0 (Hz) | F0-related | mean F0 (RP) | 0.95 |
|  | percent pause time (PPT, %), canonical timing alignment (CTA, %) [36], number of syllables (specific for DDK), word count* | Timing alignment | CTA (RP) | 0.92 |
| Video | velocity, acceleration, jerk, and speed of jaw center | Jaw movement | avg. JC speed (DDK) | 0.73 |
|  | lip aperture/opening, lip width, mouth surface area | Mouth measurements | max. lip width (RP) | 0.80 |
|  | velocity, acceleration, jerk, and speed of lower lip | Lip movement | max. LL velocity upwards (RP) | 0.61 |
|  | eye opening, vertical displacement of eyebrows | Eyes-related | max. vertical eyebrow displacement (RP) | 0.77 |
|  | mean symmetry ratio between left and right half of the mouth | Mouth symmetry | avg. mouth sym. ratio (PD) | 0.69 |
| Text | percentage of content words, noun rate, verb rate, pronoun rate, noun-to-verb ratio, noun-to-pronoun ratio, closed class word ratio, idea density | Lexico-semantic | verb-to-noun ratio (PD) | 0.25 |

Figure 24

Table 2: Mean results from 5-fold cross validation for the binary classification task bulbar onset vs. non-bulbar onset. [1]DDK, [2]Reading passage, [3]Picture description. UAR: unweighted average recall, Sen.: sensitivity, Spec.: specificity.

| | TRAIN | | | TEST | | |
|---|---|---|---|---|---|---|
| | J | AUC | Sen. | Spec. | UAR | |
| HNR[1] | 0.33 | 0.69 | 0.71 | 0.62 | 0.67 | |
| sp. dur[2] | 0.70 | 0.86 | 0.87 | 0.73 | 0.80 | |
| mean F0[2] | 0.25 | 0.64 | 0.43 | 0.66 | 0.55 | |
| CTA[2] | 0.64 | 0.84 | 0.14 | 0.93 | 0.53 | |
| avg. JC speed[1] | 0.14 | 0.55 | 0.71 | 0.39 | 0.55 | |
| max. lip width[2] | 0.30 | 0.70 | 0.79 | 0.48 | 0.63 | |
| max. LL vel. up[2] | 0.14 | 0.58 | 0.62 | 0.45 | 0.54 | |
| max. eyebrow displ.[2] | 0.34 | 0.70 | 0.57 | 0.73 | 0.65 | |
| avg. mouth sym.[3] | 0.06 | 0.53 | 0.48 | 0.43 | 0.46 | |
| verb:noun ratio[3] | 0.16 | 0.54 | 0.40 | 0.74 | 0.57 | |
| Baseline | 0.53 | 0.82 | 0.69 | 0.74 | 0.71 | |
| Youden | 0.75 | 0.87 | 0.88 | 0.74 | 0.81 | |
| LDA | 0.67 | 0.88 | 0.83 | 0.70 | 0.77 | |
| Log. regr. | 0.67 | 0.87 | 0.88 | 0.71 | 0.79 | |

Figure 25

INTERPRETABLE INDEX SCORE FOR COMBINING MULTIMODAL METRICS FOR REMOTE MONITORING OF CONDITION PROGRESSION

PRIORITY DATA

This application claims the benefit of and priority to U.S. Provisional Patent Application No. 63/551,060, titled "System and Method to Estimate Responsiveness and Optimal Participant Sample Sizes for ALS Clinical Trials Using Digital Speech Biomarkers," filed Feb. 7, 2024. The priority application is incorporated herein by reference in its entirety and for all purposes as if completely and fully set forth herein.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Deep learning is a frontier for artificial intelligence, aiming to be closer to its primary goal-artificial intelligence. Deep learning has seen great success in a wide variety of applications, such as natural language processing, speech recognition, medical applications, computer vision, and intelligent transportation systems. The great success of deep learning is due to the larger models. The scale of these models has included hundreds of millions of parameters. These hundreds of millions of parameters allow the model to have more degrees of freedom enough to produce awe-inspiring description capability.

However, the large number of parameters requires a massive amount of training data with labels. Improving model performance by data annotation has two crucial challenges. On the one hand, the data growth rate is far behind the growth rate of model parameters, so data growth has primarily hindered the further development of the model. On the other hand, the emergence of new tasks has far exceeded the speed of data updates, and annotating for all samples is laborious.

To tackle this challenge, new datasets are built by generating synthetic samples, thereby speeding up model iteration and reducing the cost of data annotation. Pre-training methods and transfer learning have also been used to solve this challenge, such as Transformers, BERT, and GPT. These works have achieved incredible results.

However, the generated data is only used as base data to initialize the model. In order to obtain a high-precision usable model, it is often necessary to label and update specific data.

Integrating apriori knowledge in the learning framework is an effective means to deal with sparse data, as the learner does not need to induce the knowledge from the data itself. As special agents, humans have rich prior knowledge. If the machine can learn human wisdom and knowledge, it will help deal with sparse data.

Human-in-the-loop (HITL) addresses these issues by incorporating human knowledge into the modeling process. HITL aims to train an accurate prediction model with minimum cost by integrating human knowledge and experience. Humans can provide training data for machine learning applications and directly accomplish some tasks that are hard for computers in the pipeline with the help of machine-based approaches.

At present, there is still a high degree of coupling between deep learning tasks and data, and the performance of deep learning largely depends on the quality of the data. For a new task, if you want to obtain better performance, you need to provide a large amount of high-quality labeled data. However, the labeled data requires a large amount of labor. In addition, large-scale data annotation takes a long time, and many iterations of tasks cannot wait such a long time. Unlike weak annotate and automatic annotate, HITL-based methods emphasize finding the key samples that play a decisive factor in new sample data.

A core set is a weighted subset of a larger set. A core set guarantees that a model fitting the core set also fits the larger set. Core set construction methods perform importance sampling with respect to sensitivity score, to provide high-probability solutions for a particular problem, such as k-means and k-median clustering, naïve Bayes and nearest-neighbors, mixture models, low rank approximation, spectral approximation, Nystrom methods, and Bayesian inference.

Supervised learning usually requires a large set of labeled data to train the prediction model. As the learning algorithms become more and more complicated, the required size of training set gets larger and larger. Meanwhile, labeling data examples is rather expensive, because the annotation process is usually time-consuming and needs high expertise in some difficult tasks. It is thus a significant challenge to learn with insufficient labeled data.

Active learning is a primary approach to overcome this challenge. It iteratively selects the most useful examples from the unlabeled dataset to query their labels from the oracle. After adding the newly labeled data into the training set, the model can be updated to achieve better performance. The key task in active learning is how to accurately estimate the potential utility of an example on improving the performance, such that the model can be well trained with minimal queries.

An opportunity arises to use human-in-the-loop (HITL) active learning for core set discovery. Accelerated deep learning with minimal coding may result.

Amyotrophic lateral sclerosis (ALS) is a progressive neurodegenerative disease that severely impacts affected persons' speech and motor functions and has an estimated global prevalence of 4.42 per 100,000 persons. Neuronal death leads to muscular atrophy, loss of voluntary motor control in persons with ALS (pALS) and a median survival of 3 to 5 years after disease onset. Up to 30% of pALS present with bulbar onset of ALS, characterised by a rapid loss of speech and swallowing functions, while the rest present with non-bulbar onset characterised by muscular atrophy in the limbs and the trunk. However, a vast majority of non-bulbar onset pALS eventually also exhibit bulbar symptoms in the course of their disease progression.

Early detection and tracking of disease progression in patients remains challenging. The current clinical gold standard to track disease progression in ALS is the ALS Functional Rating Scale-Revised (ALSFRS-R), a questionnaire comprising 12 questions across four functional domains impacted by ALS: bulbar, fine motor, gross motor and respiratory. However, the ALSFRS-R scale may track disease progression in a non-linear manner and may lack sensitivity in the early stages of bulbar disease onset. In particular, the ALSFRS-R scale is based on subjective ratings of symptom severity and may not capture subtle but meaningful changes due to a lack of granularity. To combat the difficulty in capturing early disease detection and progression, multimodal speech measured can be utilized, in which the speech measures are captured from patents and analyzed in an effort to quantify how long it takes to detect a meaningful change associated with disease progression. Accordingly, the heterogeneous nature of ALS onset and progression underlines the importance of identifying efficacious biomarkers to improve the predictive modelling of disease progression.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which.

FIG. 10 is a flowchart of a process to train a machine learning algorithm, according to some implementations.

FIG. 13 is a table showing one example of participant statistics used for identifying efficacious markers.

FIG. 15 is a table showing an overview of extracted metrics from remotely collected multimodal digital markers.

FIG. 17 is a table showing resulting feature clusters from hierarchical clustering and the corresponding selected representative features.

FIG. 18 is a table showing resulting metric responsiveness for both sign and non-sign onsets.

FIG. 19 is a table showing corresponding metric sensitivity.

FIG. 24 is a table showing extracted metrics, feature clusters, and selected representative metrics.

FIG. 25 is a table showing mean results from 5-fold cross validation.

DETAILED DESCRIPTION

Figure 1:
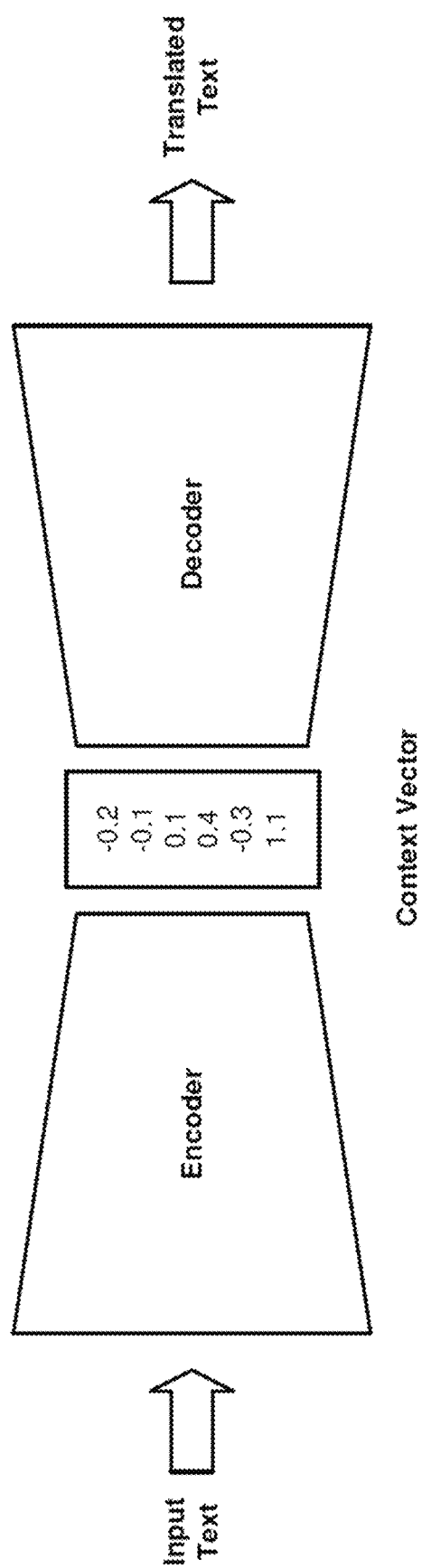
FIG. 1 is a block diagram of a system illustrating large language models (LLMs) to perform specialized healthcare-related functions, according to some implementations.

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

Some implementations of the technology disclosed relate to using a Transformer model to provide an AI system. In particular, the technology disclosed proposes a parallel input, parallel output (PIPO) AI system based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence. This stands in contrast to, e.g., convolutional architectures which typically only have a limited receptive field.

In one implementation, the disclosed AI system is a multilayer perceptron (MLP). In another implementation, the disclosed AI system is a feedforward neural network. In yet another implementation, the disclosed AI system is a fully connected neural network. In a further implementation, the disclosed AI system is a fully convolution neural network. In a yet further implementation, the disclosed AI system is a semantic segmentation neural network. In a yet another further implementation, the disclosed AI system is a generative adversarial network (GAN) (e.g., CycleGAN, StyleGAN, pixelRNN, text-2-image, DiscoGAN, IsGAN). In a yet another implementation, the disclosed AI system includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLAMA versions, BERT, Span-BERT, ROBERTa, XLNet, ELECTRA, UniLM, BART, T5, ERNIE (THU), KnowBERT, DeiT-Ti, DeiT-S, DeiT-B, T2T-ViT-14, T2T-ViT-19, T2T-ViT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCiT-S12/16, CMT-S, CMT-B, VOLO-D1, VOLO-D2, VOLO-D3, VOLO-D4, MoCo v3, ACT, TSP, Max-Deep-Lab, VisTR, SETR, Hand-Transformer, HOT-Net, METRO, Image Transformer, Taming transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, VITB/16-FRCNN, VIT-B/16-FRCNN, PVT-Small+RetinaNet, Swin-T+Retina-Net, Swin-T+ATSS, PVT-Small+DETR, TNT-S+DETR, YOLOS-Ti, YOLOS-S, and YOLOS-B.

In one implementation, the disclosed AI system is a convolution neural network (CNN) with a plurality of convolution layers. In another implementation, the disclosed AI system is a recurrent neural network (RNN) such as a long short-term memory network (LSTM), bi-directional LSTM (Bi-LSTM), or a gated recurrent unit (GRU). In yet another implementation, the disclosed AI system includes both a CNN and an RNN.

In yet other implementations, the disclosed AI system can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The disclosed AI system can use one or more loss functions such as logistic regression/log loss, multi-class cross-entropy/softmax loss, binary cross-entropy loss, mean-squared error loss, L1 loss, L2 loss, smooth L1 loss, and Huber loss. The disclosed AI system can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed AI system can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The disclosed AI system can be a linear regression model, a logistic regression model, an Elastic Net model, a support vector machine (SVM), a random forest (RF), a decision tree, and a boosted decision tree (e.g., XGBoost), or some other tree-based logic (e.g., metric trees, kd-trees, R-trees, universal B-trees, X-trees, ball trees, locality sensitive hashes, and inverted indexes). The disclosed AI system can be an ensemble of multiple models, in some implementations.

In some implementations, the disclosed AI system can be trained using backpropagation-based gradient update techniques. Example gradient descent techniques that can be used for training the disclosed AI system include stochastic gradient descent, batch gradient descent, and mini-batch gradient descent. Some examples of gradient descent optimization algorithms that can be used to train the disclosed AI system are Momentum, Nesterov accelerated gradient, Adagrad, Adadelta, RMSprop, Adam, AdaMax, Nadam, and AMSGrad.

Transformer Logic

Machine learning is the use and development of computer systems that can learn and adapt without following explicit instructions, by using algorithms and statistical models to analyze and draw inferences from patterns in data. Some of the state-of-the-art models use Transformers, a more powerful and faster model than neural networks alone. Transformers originate from the field of natural language processing (NLP), but can be used in computer vision and many other fields. Neural networks process input in series and weight relationships by distance in the series. Transformers can process input in parallel and do not necessarily weigh by distance. For example, in natural language processing, neural networks process a sentence from beginning to end with the weights of words close to each other being higher than those further apart. This leaves the end of the sentence very disconnected from the beginning causing an effect called the vanishing gradient problem. Transformers look at each word in parallel and determine weights for the relationships to each of the other words in the sentence. These relationships are called hidden states because they are later condensed for use into one vector called the context vector. Transformers can be used in addition to neural networks. This architecture is described here.

Encoder-Decoder Architecture

FIG. 1 is a schematic representation of an encoder-decoder architecture. This architecture is often used for NLP and has two main building blocks. The first building block is the encoder that encodes an input into a fixed-size vector. In the system we describe here, the encoder is based on a recurrent neural network (RNN). At each time step, t, a hidden state of time step, t-1, is combined with the input value at time step t to compute the hidden state at timestep t. The hidden state at the last time step, encoded in a context vector, contains relationships encoded at all previous time steps. For NLP, each step corresponds to a word. Then the context vector contains information about the grammar and the sentence structure. The context vector can be considered a low-dimensional representation of the entire input space. For NLP, the input space is a sentence, and a training set consists of many sentences.

The context vector is then passed to the second building block, the decoder. For translation, the decoder has been trained on a second language. Conditioned on the input context vector, the decoder generates an output sequence. At each time step, t, the decoder is fed the hidden state of time step, t-1, and the output generated at time step, t-1. The first hidden state in the decoder is the context vector, generated by the encoder. The context vector is used by the decoder to perform the translation.

The whole model is optimized end-to-end by using backpropagation, a method of training a neural network in which the initial system output is compared to the desired output and the system is adjusted until the difference is minimized. In backpropagation, the encoder is trained to extract the right information from the input sequence, the decoder is trained to capture the grammar and vocabulary of the output language. This results in a fluent model that uses context and generalizes well. When training an encoder-decoder model, the real output sequence is used to train the model to prevent mistakes from stacking. When testing the model, the previously predicted output value is used to predict the next one.

When performing a translation task using the encoder-decoder architecture, all information about the input sequence is forced into one vector, the context vector. Information connecting the beginning of the sentence with the end is lost, the vanishing gradient problem. Also, different parts of the input sequence are important for different parts of the output sequence, information that cannot be learned using only RNNs in an encoder-decoder architecture.

Attention Mechanism

Figure 2:
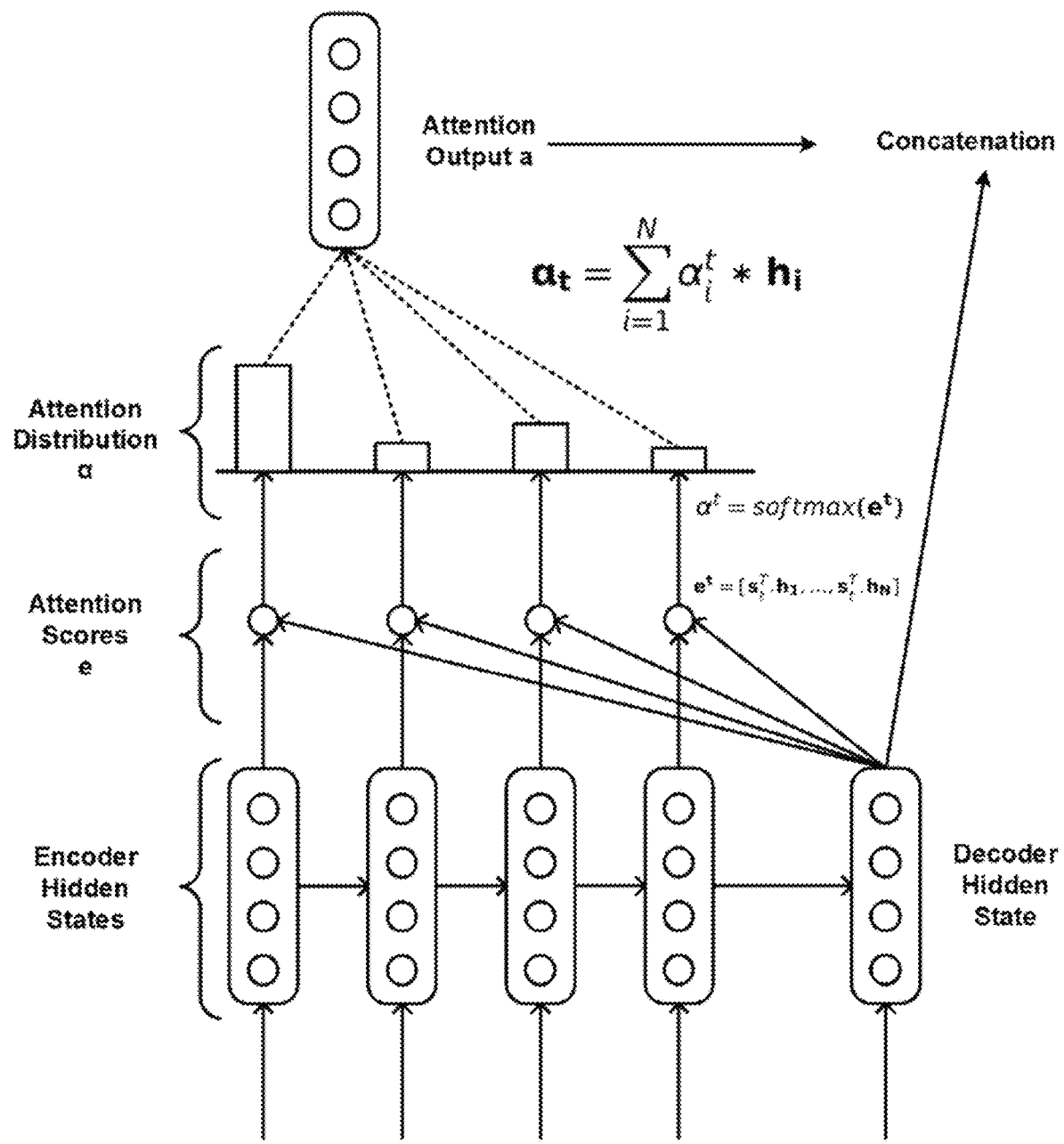
FIG. 2 is a block diagram illustrating an artificial intelligence (AI) architecture, according to some implementations.

Attention mechanisms distinguish Transformers from other machine learning models. The attention mechanism provides a solution for the vanishing gradient problem. FIG. 2 shows an overview of an attention mechanism added onto an RNN encoder-decoder architecture. At every step, the decoder is given an attention score, e, for each encoder hidden state. In other words, the decoder is given weights for each relationship between words in a sentence. The decoder uses the attention score concatenated with the context vector during decoding. The output of the decoder at time step t is based on all encoder hidden states and the attention outputs. The attention output captures the relevant context for time step t from the original sentence. Thus, words at the end of a sentence may now have a strong relationship with words at the beginning of the sentence. In the sentence "The quick brown fox, upon arriving at the doghouse, jumped over the lazy dog," fox and dog can be closely related despite being far apart in this complex sentence.

To weight encoder hidden states, a dot product between the decoder hidden state of the current time step, and all encoder hidden states, is calculated. This results in an attention score for every encoder hidden state. The attention scores are higher for those encoder hidden states that are similar to the decoder hidden state of the current time step. Higher values for the dot product indicate the vectors are pointing more closely in the same direction. The attention scores are converted to fractions that sum to one using the SoftMax function.

The SoftMax scores provide an attention distribution. The x-axis of the distribution is position in a sentence. The y-axis is attention weight. The scores show which encoder hidden states are most closely related. The SoftMax scores specify which encoder hidden states are the most relevant for the decoder hidden state of the current time step.

The elements of the attention distribution are used as weights to calculate a weighted sum over the different encoder hidden states. The outcome of the weighted sum is called the attention output. The attention output is used to predict the output, often in combination (concatenation) with the decoder hidden states. Thus, both information about the inputs, as well as the already generated outputs, can be used to predict the next outputs.

By making it possible to focus on specific parts of the input in every decoder step, the attention mechanism solves the vanishing gradient problem. By using attention, information flows more directly to the decoder. It does not pass through many hidden states. Interpreting the attention step can give insights into the data. Attention can be thought of as a soft alignment. The words in the input sequence with a high attention score align with the current target word. Attention describes long-range dependencies better than RNN alone. This enables analysis of longer, more complex sentences.

The attention mechanism can be generalized as: given a set of vector values and a vector query, attention is a technique to compute a weighted sum of the vector values, dependent on the vector query. The vector values are the encoder hidden states, and the vector query is the decoder hidden state at the current time step.

The weighted sum can be considered a selective summary of the information present in the vector values. The vector query determines on which of the vector values to focus. Thus, a fixed-size representation of the vector values can be created, in dependence upon the vector query.

The attention scores can be calculated by the dot product, or by weighing the different values (multiplicative attention).

Embeddings

For most machine learning models, the input to the model needs to be numerical. The input to a translation model is a sentence, and words are not numerical. multiple methods exist for the conversion of words into numerical vectors. These numerical vectors are called the embeddings of the words. Embeddings can be used to convert any type of symbolic representation into a numerical one.

Embeddings can be created by using one-hot encoding. The one-hot vector representing the symbols has the same length as the total number of possible different symbols. Each position in the one-hot vector corresponds to a specific symbol. For example, when converting colors to a numerical vector, the length of the one-hot vector would be the total number of different colors present in the dataset. For each input, the location corresponding to the color of that value is one, whereas all the other locations are valued at zero. This works well for working with images. For NLP, this becomes problematic, because the number of words in a language is very large. This results in enormous models and the need for a lot of computational power. Furthermore, no specific information is captured with one-hot encoding. From the numerical representation, it is not clear that orange and red are more similar than orange and green. For this reason, other methods exist.

A second way of creating embeddings is by creating feature vectors. Every symbol has its specific vector representation, based on features. With colors, a vector of three elements could be used, where the elements represent the amount of yellow, red, and/or blue needed to create the color. Thus, all colors can be represented by only using a vector of three elements. Also, similar colors have similar representation vectors.

For NLP, embeddings based on context, as opposed to words, are small and can be trained. The reasoning behind this concept is that words with similar meanings occur in similar contexts. Different methods take the context of words into account. Some methods, like GloVe, base their context embedding on co-occurrence statistics from corpora (large texts) such as Wikipedia. Words with similar co-occurrence statistics have similar word embeddings. Other methods use neural networks to train the embeddings. For example, they train their embeddings to predict the word based on the context (Common Bag of Words), and/or to predict the context based on the word (Skip-Gram). Training these contextual embeddings is time intensive. For this reason, pre-trained libraries exist. Other deep learning methods can be used to create embeddings. For example, the latent space of a variational autoencoder (VAE) can be used as the embedding of the input. Another method is to use 1D convolutions to create embeddings. This causes a sparse, high-dimensional input space to be converted to a denser, low-dimensional feature space.

Self-Attention: Queries (Q), Keys (K), Values (V)

Transformer models are based on the principle of self-attention. Self-attention allows each element of the input sequence to look at all other elements in the input sequence and search for clues that can help it to create a more meaningful encoding. It is a way to look at which other sequence elements are relevant for the current element. The Transformer can grab context from both before and after the currently processed element.

When performing self-attention, three vectors need to be created for each element of the encoder input: the query vector (Q), the key vector (K), and the value vector (V). These vectors are created by performing matrix multiplications between the input embedding vectors using three unique weight matrices.

After this, self-attention scores are calculated. When calculating self-attention scores for a given element, the dot products between the query vector of this element and the key vectors of all other input elements are calculated. To make the model mathematically more stable, these self-attention scores are divided by the root of the size of the vectors. This has the effect of reducing the importance of the scalar thus emphasizing the importance of the direction of the vector. Just as before, these scores are normalized with a SoftMax layer. This attention distribution is then used to calculate a weighted sum of the value vectors, resulting in a vector z for every input element. In the attention principle explained above, the vector to calculate attention scores and to perform the weighted sum was the same, in self-attention two different vectors are created and used. As the self-attention needs to be calculated for all elements (thus a query for every element), one formula can be created to calculate a Z matrix. The rows of this Z matrix are the z vectors for every sequence input element, giving the matrix a size length sequence dimension QKV.

Figure 3:
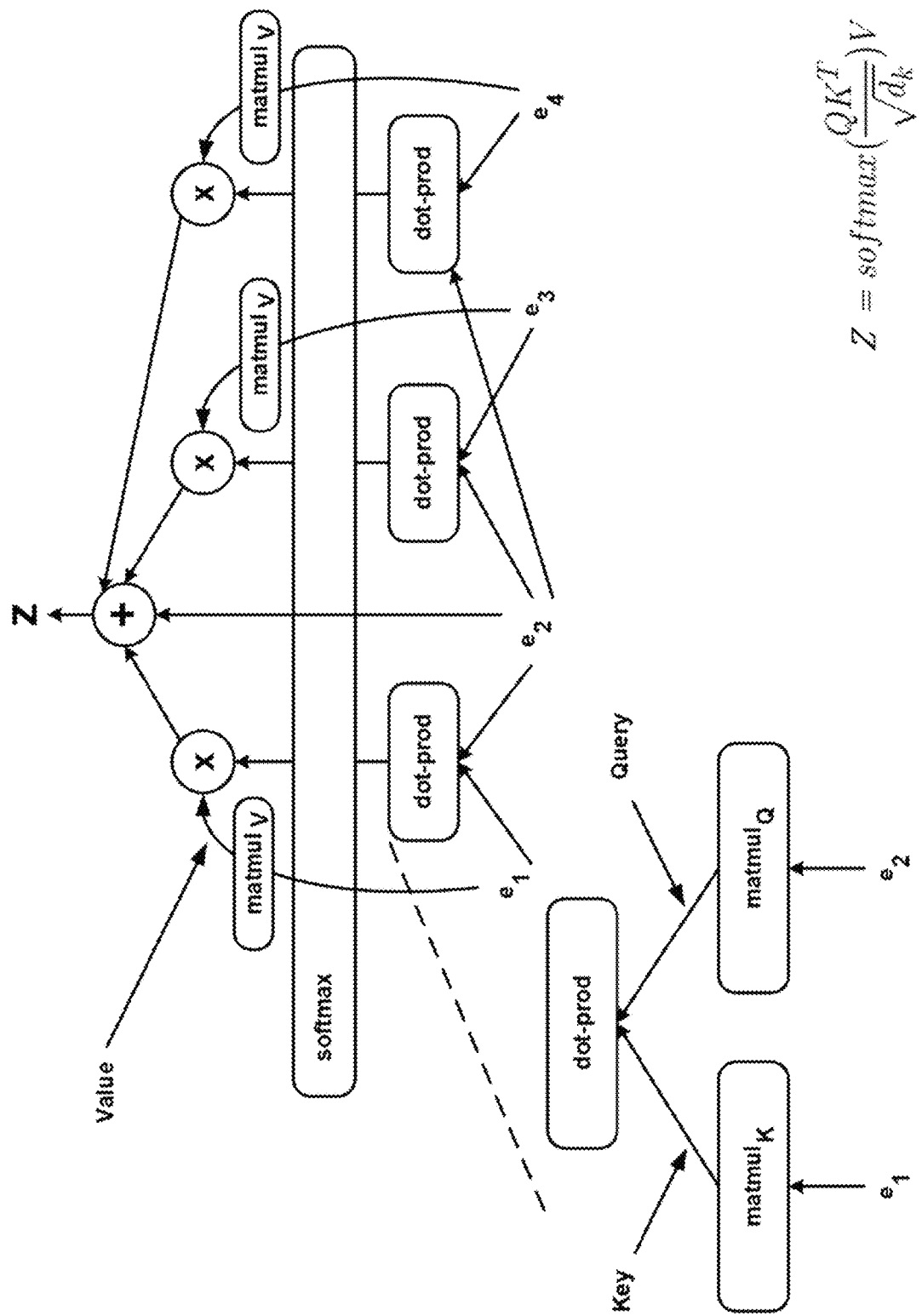
FIG. 3 is a block diagram of a system that includes a low-latency conversational artificial intelligence (AI) architecture with a parallelized in-depth analysis and feedback loop, according to some implementations.

Multi-headed attention is executed in the Transformer. FIG. 3 is a schematic representation of the calculation of self-attention showing one attention head. For every attention head, different weight matrices are trained to calculate Q, K, and V. Every attention head outputs a matrix Z. Different attention heads can capture different types of information. The different Z matrices of the different attention heads are concatenated. This matrix can become large when multiple attention heads are used. To reduce dimensionality, an extra weight matrix W is trained to condense the different attention heads into a matrix with the same size as one Z matrix. This way, the amount of data given to the next step does not enlarge every time self-attention is performed.

When performing self-attention, information about the order of the different elements within the sequence is lost. To address this problem, positional encodings are added to the embedding vectors. Every position has its unique positional encoding vector. These vectors follow a specific pattern, which the Transformer model can learn to recognize. This way, the model can consider distances between the different elements.

As discussed above, in the core of self-attention are three objects: queries (Q), keys (K), and values (V). Each of these objects has an inner semantic meaning of their purpose. One can think of these as analogous to databases. We have a user-defined query of what the user wants to know. Then we have the relations in the database, i.e., the values which are the weights. More advanced database management systems create some apt representation of its relations to retrieve values more efficiently from the relations. This can be achieved by using indexes, which represent information about what is stored in the database. In the context of attention, indexes can be thought of as keys. So instead of running the query against values directly, the query is first executed on the indexes to retrieve where the relevant values or weights are stored. Lastly, these weights are run against the original values to retrieve data that is most relevant to the initial query.

Figure 4:
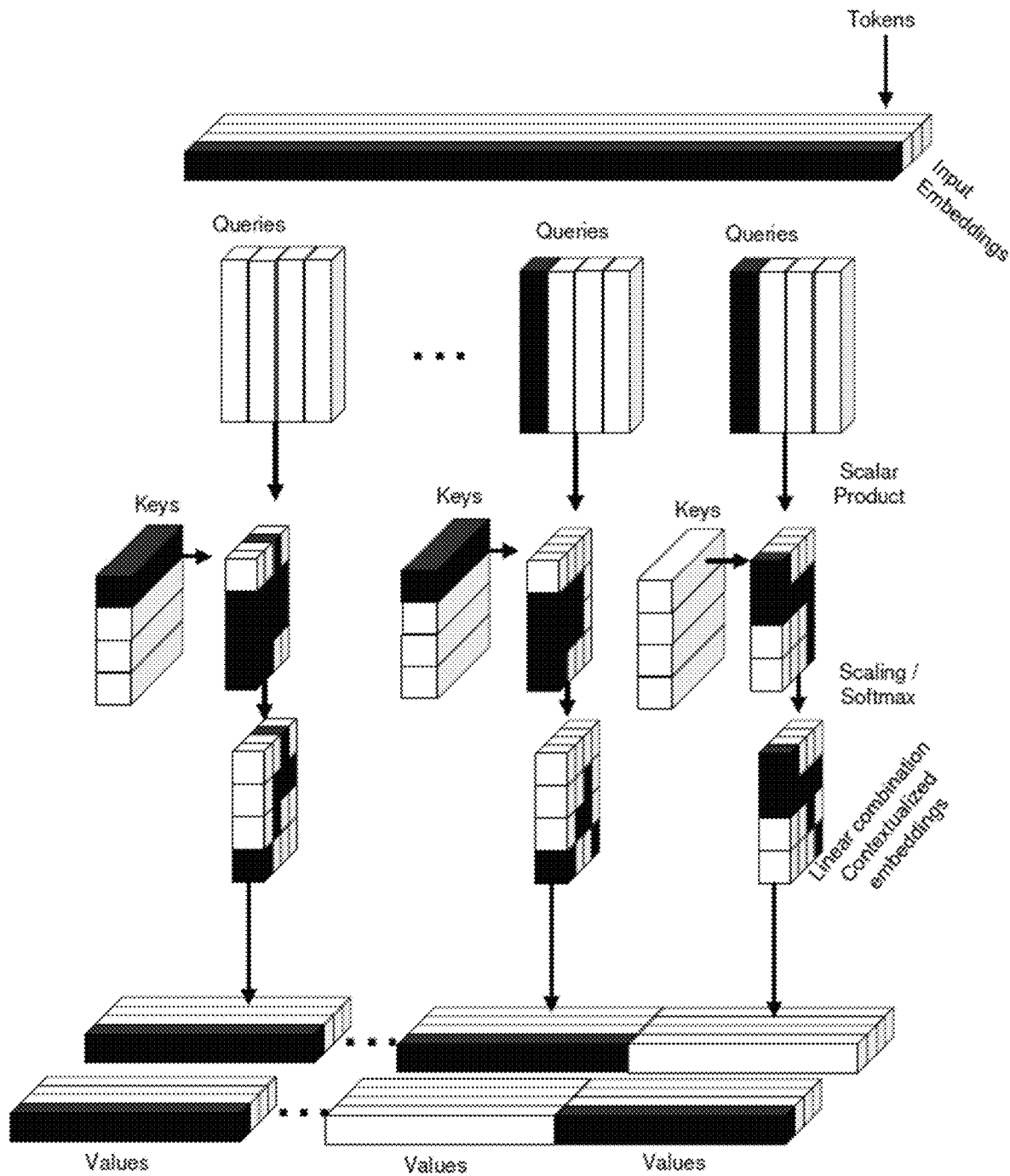
FIG. 4 is a block diagram illustrating components of training data, according to some implementations.

FIG. 4 depicts several attention heads in a Transformer block. We can see that the outputs of queries and keys dot products in different attention heads are differently colored. This depicts the capability of the multi-head attention to focus on different aspects of the input and aggregate the obtained information by multiplying the input with different attention weights.

Examples of attention calculation include scaled dot-product attention and additive attention. There are several reasons why scaled dot-product attention is used in the Transformers. Firstly, the scaled dot-product attention is relatively fast to compute, since its main parts are matrix operations that can be run on modern hardware accelerators. Secondly, it performs similarly well for smaller dimensions of the K matrix, dk, as the additive attention. For larger dk, the scaled dot-product attention performs a bit worse because dot products can cause the vanishing gradient problem. This is compensated via the scaling factor, which is defined as $\sqrt{dk}$.

As discussed above, the attention function takes as input three objects: key, value, and query. In the context of Transformers, these objects are matrices of shapes (n, d), where n is the number of elements in the input sequence and d is the hidden representation of each element (also called the hidden vector). Attention is then computed as:

$$\text{Attention}(Q, K, V) = \text{SoftMax}\left(\frac{QK^T}{\sqrt{dk}}\right)V$$

where Q, K, L' are computed as:

$$X \cdot W_Q, X \cdot W_K, X \cdot W_V$$

X is the input matrix and $W_Q$, $W_K$, $W_V$ are learned weights to project the input matrix into the representations. The dot products appearing in the attention function are exploited for their geometrical interpretation where higher values of their results mean that the inputs are more similar, i.e., pointing in the geometrical space in the same direction. Since the attention function now works with matrices, the dot product becomes matrix multiplication. The SoftMax function is used to normalize the attention weights into the value of 1 prior to being multiplied by the values matrix. The resulting matrix is used either as input into another layer of attention or becomes the output of the Transformer.

Multi-Head Attention

Transformers become even more powerful when multi-head attention is used. Queries, keys, and values are computed the same way as above, though they are now projected into h different representations of smaller dimensions using a set of h learned weights. Each representation is passed into a different scaled dot-product attention block called a head. The head then computes its output using the same procedure as described above.

Formally, the multi-head attention is defined as:

MultiHeadAttention$(Q,K,V)$=[head$_1$, ... ,head$_h$]$W_0$
where head$_i$=Attention $(QW_i^Q, KW_i^K, VW_i^V)$ The outputs of all heads are concatenated together and projected again using the learned weights matrix $W_0$ to match the dimensions expected by the next block of heads or the output of the Transformer. Using the multi-head attention instead of the simpler scaled dot-product attention enables Transformers to jointly attend to information from different representation subspaces at different positions.

Figure 5:
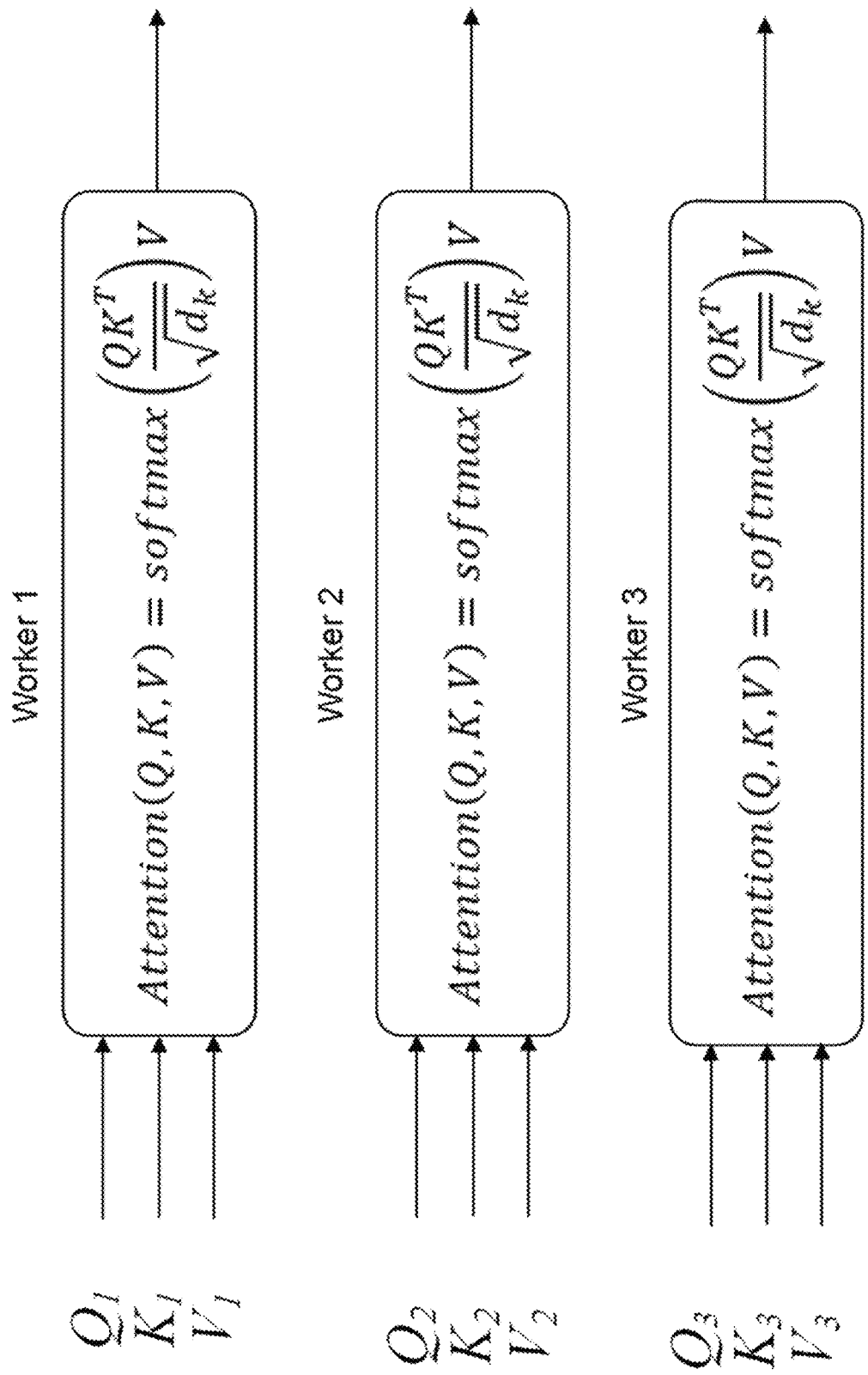
FIG. 5 is a block diagram illustrating an AI checklist, according to some implementations.

As shown in FIG. 5, one can use multiple workers to compute the multi-head attention in parallel, as the respective heads compute their outputs independently of one another. Parallel processing is one of the advantages of Transformers over RNNs.

Assuming the naive matrix multiplication algorithm which has a complexity of:

$$a \cdot b \cdot c$$

For matrices of shape (a, b) and (c, d), to obtain values Q, K, V, we need to compute the operations:

$$X \cdot W_Q, X \cdot W_K, X \cdot W_V$$

The matrix X is of shape (n, d) where n is the number of patches and d is the hidden vector dimension. The weights $W_Q$, $W_K$, $W_V$ are all of shape (d, d). Omitting the constant factor 3, the resulting complexity is:

$$n \cdot d^2$$

We can proceed to the estimation of the complexity of the attention function itself, i.e., of $$SoftMax\left(\frac{QK^T}{\sqrt{dk}}\right)V.$$

The matrices Q and K are both of shape (n, d). The transposition operation does not influence the asymptotic complexity of computing the dot product of matrices of shapes (n, d)·(d, n), therefore its complexity is:

$$n^2 \cdot d$$

Scaling by a constant factor of $\sqrt{dk}$, where dk is the dimension of the keys vector, as well as applying the SoftMax function, both have the complexity of a·b for a matrix of shape (a, b), hence they do not influence the asymptotic complexity. Lastly the dot product $$SoftMax\left(\frac{QK^T}{\sqrt{dk}}\right) \cdot V$$

is between matrices of shapes (n, n) and (n, d) and so its complexity is:

$$n^2 \cdot d$$

The final asymptotic complexity of scaled dot-product attention is obtained by summing the complexities of computing Q, K, V, and of the following attention function:

$$n \cdot d^2 + n^2 \cdot d.$$

The asymptotic complexity of multi-head attention is the same since the original input matrix X is projected into h matrices of shapes $$\left(n, \frac{d}{h}\right),$$

where h is the number or heads. From the point of view of asymptotic complexity, h is constant, therefore we would arrive at the same estimate of asymptotic complexity using a similar approach as for the scaled dot-product attention.

Transformer models often have the encoder-decoder architecture, although this is not necessarily the case. The encoder is built out of different encoder layers which are all constructed in the same way. The positional encodings are added to the embedding vectors. Afterward, self-attention is performed.

Encoder Block of Transformer

Figure 6:
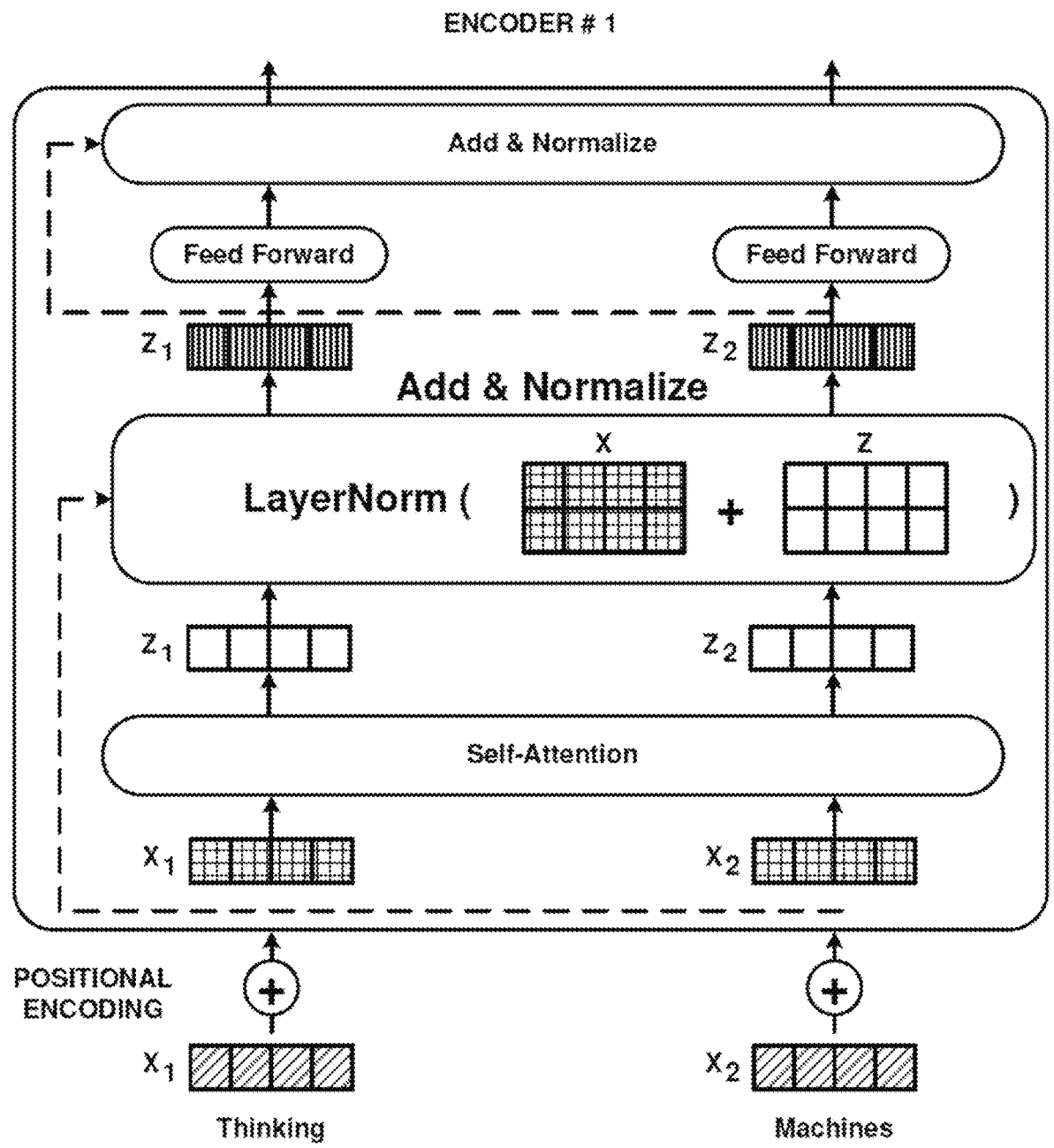
FIG. 6 is a block diagram illustrating AI-human engagement, according to some implementations.

FIG. 6 portrays one encoder layer of a Transformer network. Every self-attention layer is surrounded by a residual connection, summing up the output and input of the self-attention. This sum is normalized, and the normalized vectors are fed to a feed-forward layer. Every z vector is fed separately to this feed-forward layer. The feed-forward layer is wrapped in a residual connection and the outcome is normalized too. Often, numerous encoder layers are piled to form the encoder. The output of the encoder is a fixed-size vector for every element of the input sequence.

Just like the encoder, the decoder is built from different decoder layers. In the decoder, a modified version of self-attention takes place. The query vector is only compared to the keys of previous output sequence elements. The elements further in the sequence are not known yet, as they still must be predicted. No information about these output elements may be used.

Encoder-Decoder Blocks of Transformer

Figure 7:
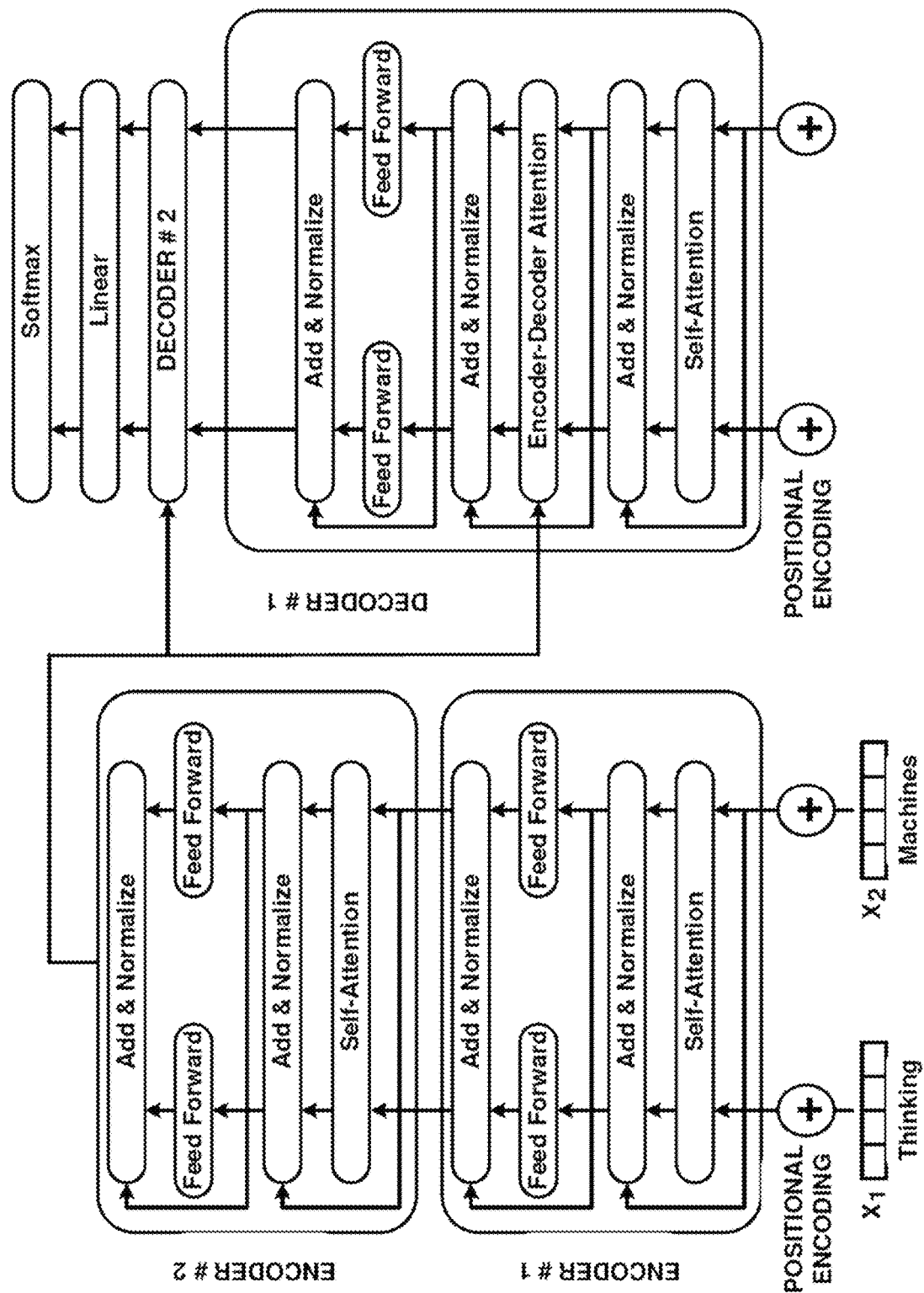
FIG. 7 is a block diagram of system that includes an LLM routing system, according to some implementations.

FIG. 7 shows a schematic overview of a Transformer model. Next to a self-attention layer, a layer of encoder-decoder attention is present in the decoder, in which the decoder can examine the last Z vectors of the encoder, providing fluent information transmission. The ultimate decoder layer is a feed-forward layer. All layers are packed in a residual connection. This allows the decoder to examine all previously predicted outputs and all encoded input vectors to predict the next output. Thus, information from the encoder is provided to the decoder, which could improve the predictive capacity. The output vectors of the last decoder layer need to be processed to form the output of the entire system. This is done by a combination of a feed-forward layer and a SoftMax function. The output corresponding to the highest probability is the predicted output value for a subject time step.

For some tasks other than translation, only an encoder is needed. This is true for both document classification and name entity recognition. In these cases, the encoded input vectors are the input of the feed-forward layer and the SoftMax layer. Transformer models have been extensively applied in different NLP fields, such as translation, document summarization, speech recognition, and named entity recognition. These models have applications in the field of biology as well for predicting protein structure and function and labeling DNA sequences.

Vision Transformer

Figure 8B:
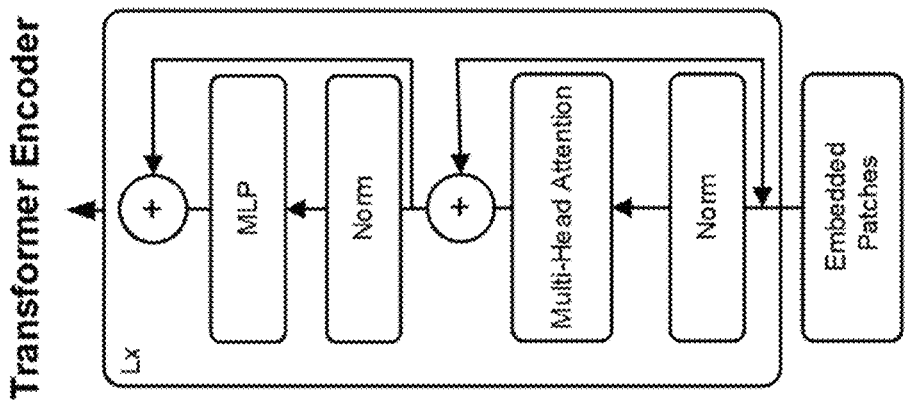
FIGS. 8A-8B are flowcharts of a process that includes analyzing a human response using a second opinion module, according to some implementations.
Figure 8A:
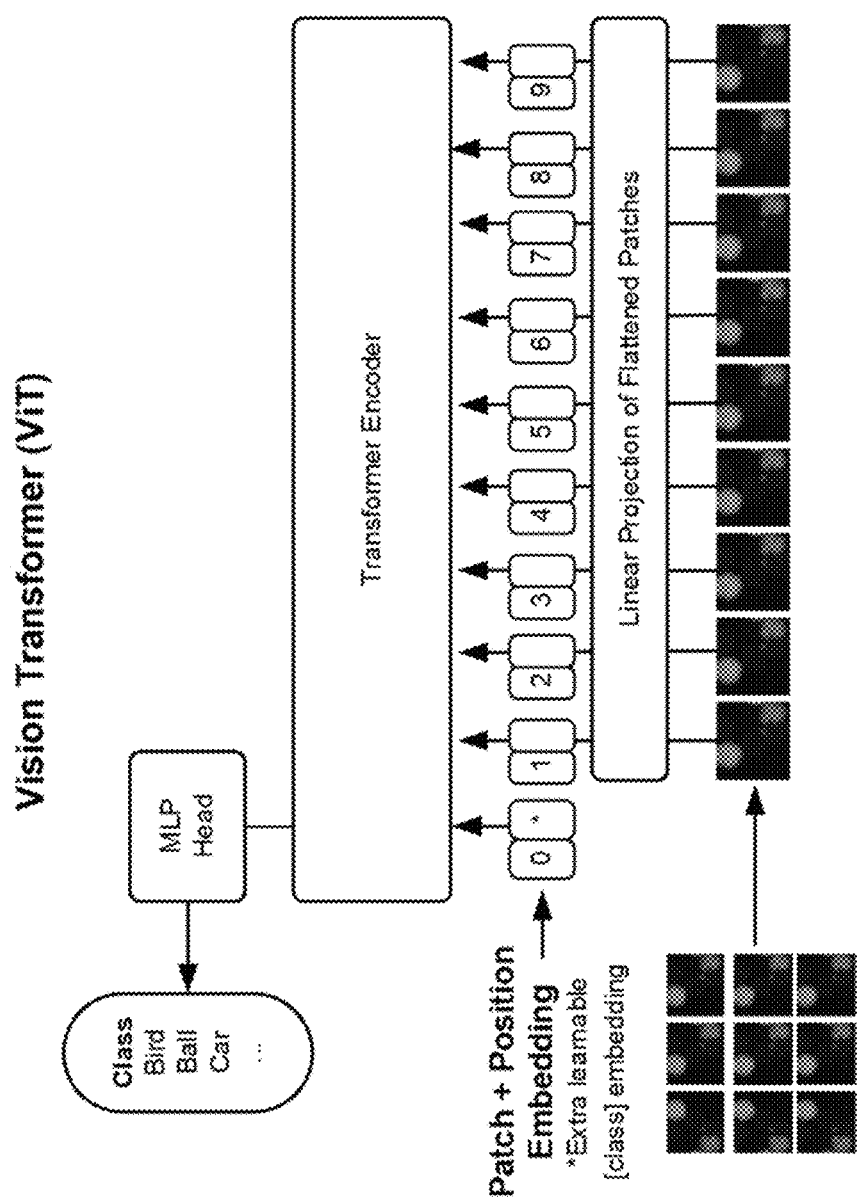
Figures 9A, 9B, 9C, 9D:
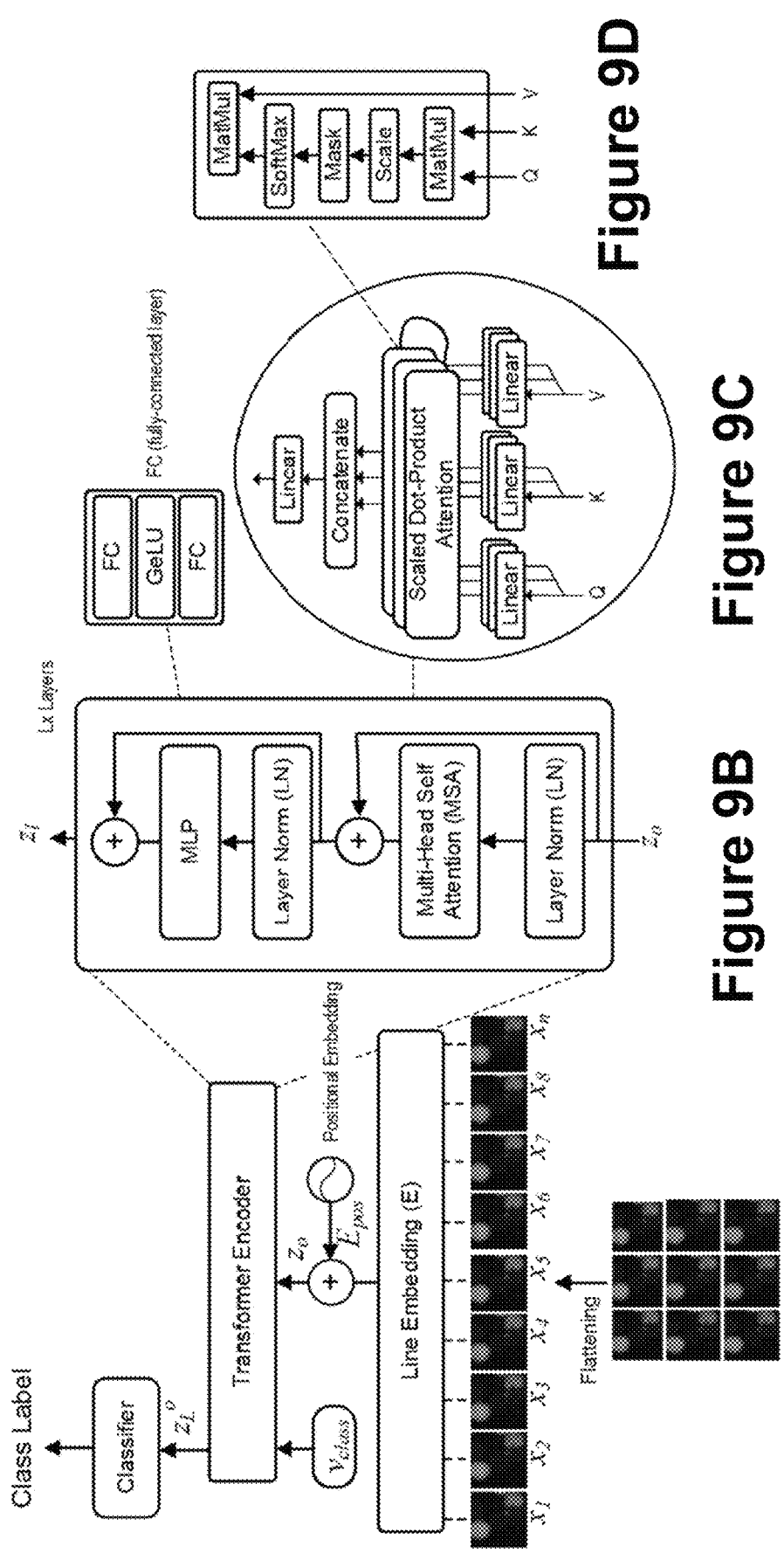
FIGS. 9A-9D are flowcharts of a process that includes accessing a conversation summary, a knowledge graph, or both, according to some implementations.

FIGS. 8A-8B are flowcharts of a process that includes analyzing a human response using a second opinion module, according to some implementations. FIGS. 9A-9D are flowcharts of a process that includes accessing a conversation summary, a knowledge graph, or both, according to some implementations. There are extensive applications of transformers in vision including popular recognition tasks (e.g., image classification, object detection, action recognition, and segmentation), generative modeling, multi-modal tasks (e.g., visual-question answering, visual reasoning, and visual grounding), video processing (e.g., activity recognition, video forecasting), low-level vision (e.g., image super-resolution, image enhancement, and colorization) and 3D analysis (e.g., point cloud classification and segmentation).

Transformers were originally developed for NLP and worked with sequences of words. In image classification, we often have a single input image in which the pixels are in a sequence. To reduce the computation required, Vision Transformers (ViTs) cut the input image into a set of fixed-sized patches of pixels. The patches are often 16×16 pixels. They are treated much like words in NLP Transformers. ViTs are depicted in FIGS. 8A, 8B, 9A, 9B, 9C, and 9D. Unfortunately, important positional information is lost because image sets are position-invariant. This problem is solved by adding a learned positional encoding into the image patches.

The computations of the ViT architecture can be summarized as follows. The first layer of a ViT extracts a fixed number of patches from an input image (FIG. 8A). The patches are then projected to linear embeddings. A special class token vector is added to the sequence of embedding vectors to include all representative information of all tokens through the multi-layer encoding procedure. The class vector is unique to each image. Vectors containing positional information are combined with the embeddings and the class token. The sequence of embedding vectors is passed into the Transformer blocks. The class token vector is extracted from the output of the last Transformer block and is passed into a multilayer perceptron (MLP) head whose output is the final classification. The perceptron takes the normalized input and places the output in categories. It classifies the images. This procedure directly translates into the Python Keras code shown in FIG. 10.

When the input image is split into patches, a fixed patch size is specified before instantiating a ViT. Given the quadratic complexity of attention, patch size has a large effect on the length of training and inference time. A single Transformer block comprises several layers. The first layer implements Layer Normalization, followed by the multi-head attention that is responsible for the performance of ViTs. In the depiction of a Transformer block in FIG. 8B, we can see two arrows. These are residual skip connections. Including skip connection data can simplify the output and improve the results. The output of the multi-head attention is followed again by Layer Normalization. And finally, the output layer is an MLP (Multi-Layer Perceptron) with the GELU (Gaussian Error Linear Unit) activation function.

ViTs can be pretrained and fine-tuned. Pretraining is generally done on a large dataset. Fine-tuning is done on a domain specific dataset.

Domain-specific architectures, like convolutional neural networks (CNNs) or long short-term memory networks (LSTMs), have been derived from the usual architecture of MLPs and suffer from so-called inductive biases that predispose the networks towards a certain output. ViTs stepped in the opposite direction of CNNs and LSTMs and became more general architectures by eliminating inductive biases. A ViT can be seen as a generalization of MLPs because MLPs, after being trained, do not change their weights for different inputs. On the other hand, ViTs compute their attention weights at runtime based on the particular input.

While the systems and methods disclosed herein are discussed with reference to pALS, it is expressly contemplated that the systems and methods described herein could be applied to other neurological or mental disorders as well. While the specific set of selected useful features, including the relative utility of different modalities, will likely be different in other disorders (cf. related work in Parkinson disease or mental health disorders like depression and schizophrenia), as well as the sensitivity analysis with respect to a traditional clinical outcome (which is dependent on the disease), it is expressly contemplated that the systems and methods described herein can be readily transferred to other diseases.

Speech and oro-facial markers have shown great promise for remote assessment and monitoring of neurological and mental health. For example, efficacy of multiple speech metrics that capture how a given disease impacts multiple domains of speech performance—be it motor, anatomical, cognitive, linguistic or affective have been shown to be effective for neurological health and assessment. Objective speech and facial kinematic measures can be very powerful in early detection of bulbar symptoms and the progression of bulbar decline in pALS. Speaking rate has been consistently found to be an important marker for early diagnosis and stratification, along with other timing-related measures like percentage pause time, speaking duration and others. Additionally, some timing-related speech markers, collected remotely through a conversational dialog platform, have the requisite responsiveness and sensitivity to track speech decline in the context of clinical interventional trials targeting neurodegenerative disorders.

To establish the efficacy of multimodal markers in tracking disease progression, it is important to consider what constitutes a minimal clinically-important difference (MCID) and whether these markers show change greater than any measurement errors. It is important that these multimodal markers are also sensitive in detecting bulbar decline, which could be well before corresponding changes are observed in the relevant clinical gold standard (i.e., ALSFRS-R) functional scores or equivalent clinical scales.

In this patent document, "biomarker(s)" and "marker(s)" are used interchangeably.

In this patent document, "neurogenerative disease," "disease", and "condition" are used interchangeable. Amyotrophic lateral sclerosis (ALS) is an example of a neurogenerative disease, a disease, or a condition.

In this patent document, "bulbar" and "sign" are used interchangeably. For example, bulbar is a sign or a trait or a symptom of having ALS.

In this patent document, a "meaningful change" refers to a "clinically meaningful change."

In this patent document, "external clinical gold standard" and "external gold standard" are used interchangeably.

As used herein, the term "metric" is utilized to denote the concept of speech and facial characteristics (e.g., speaking rate), and the term "feature" is utilized to denote a metric that was extracted for a specific stimulus or task (e.g., speaking rate for a reading passage task).

Figure 11A:
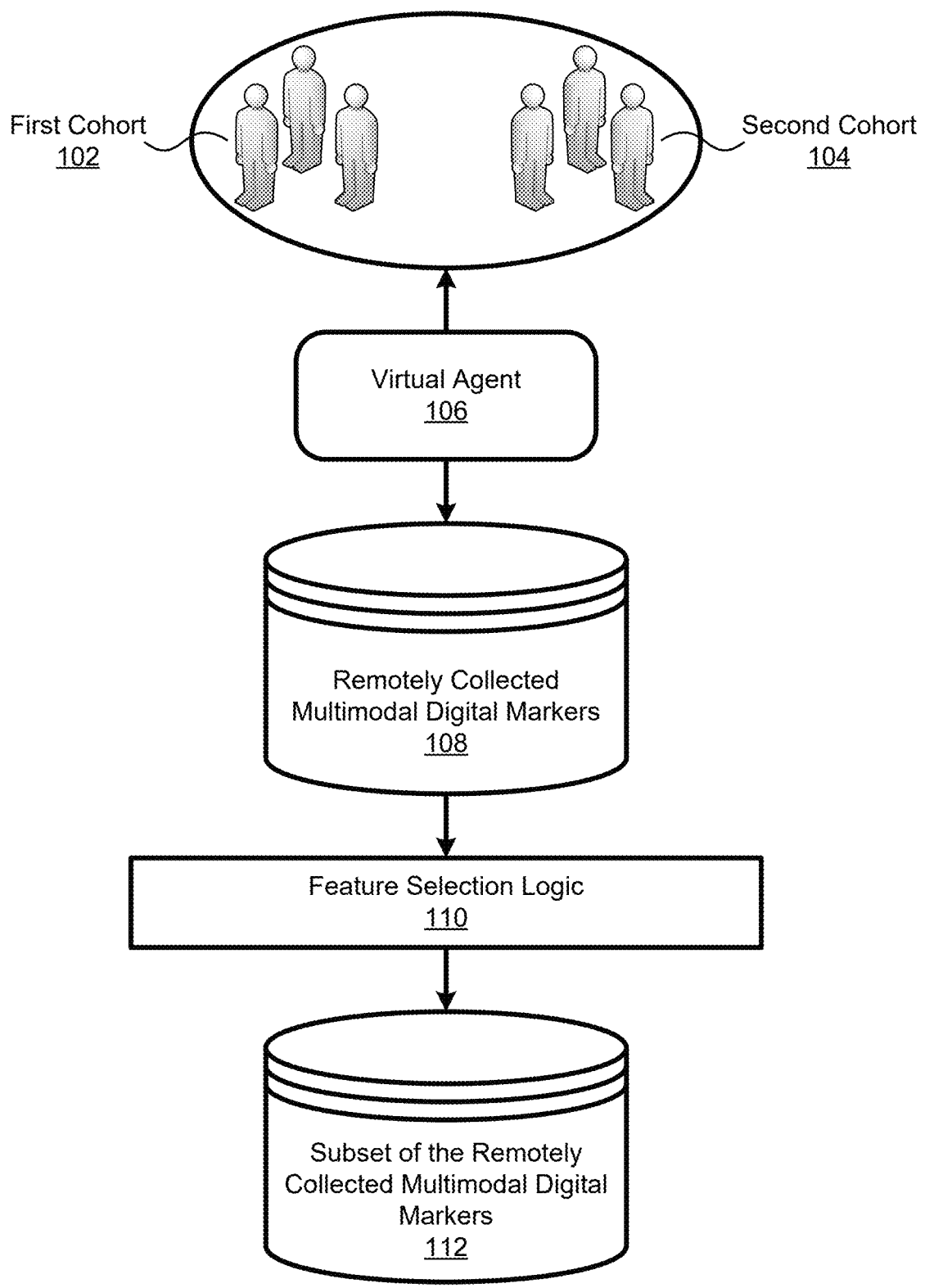
FIGS. 11A, 11B, 11C are diagrams showing one example of a marker identification system.
Figure 11B:
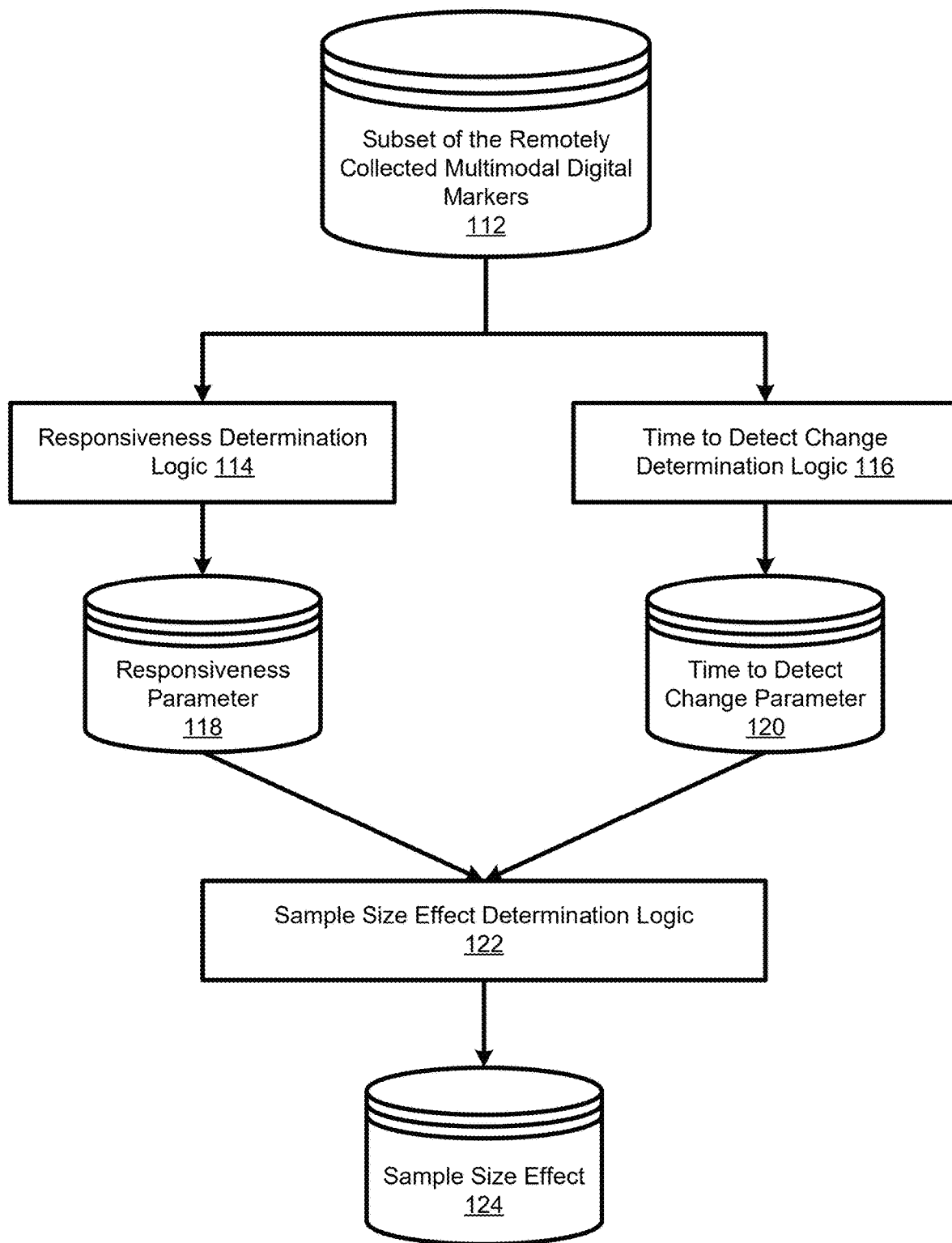
Figure 11C:
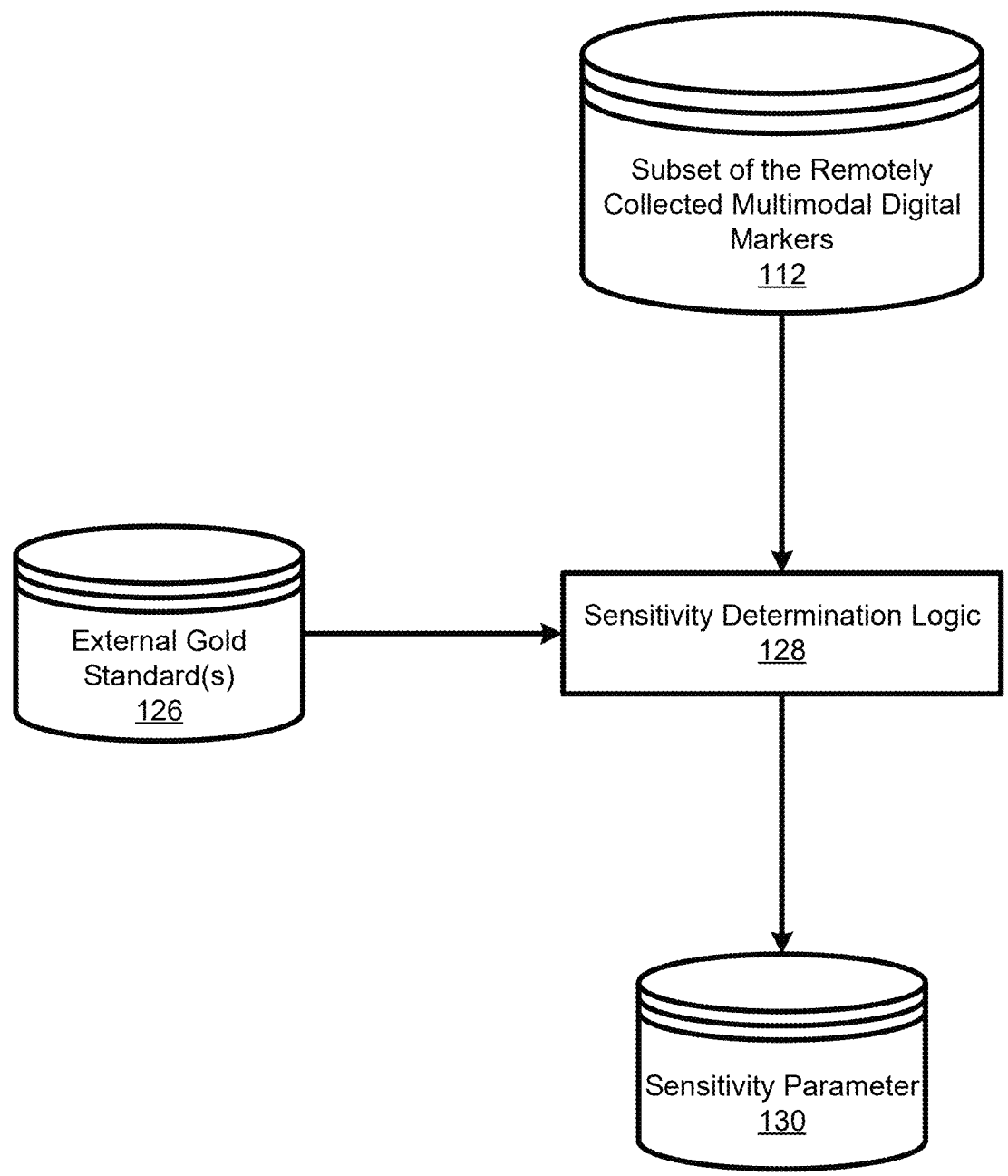

FIGS. 11A, 11B, 11C are diagrams showing one example of a marker identification system. As shown in FIG. 11A, a first cohort 102 and second cohort 104 can be assessed by virtual agent 106 to remotely collect multimodal digital markers. In one example, first cohort 102 can be a cohort experiencing a bulbar onset in condition progression, and the second cohort can be a cohort experiencing a non-bulbar onset in condition progression.

Virtual agent 106 is equipped with analytics modules that automatically extract metrics to capture information from acoustic (energy, timing, voice quality, spectral), facial (articulatory kinematics, range of motion, eye and facial movement), motoric (finger tapping kinematics) and textual (lexico-semantic, sentiment) domains during the different tasks. For example, Praat (v6.2.17) and the Montreal Forced Aligner (v2.0.0.a22) can be utilized to extract speech metrics, including timing measures, such as percentage of pause time (PPT; proportion of the total duration of all pauses to the total duration of the utterance), rate measures such as speaking rate (the total number of words in the passage divided by the speaking duration, or time taken to read a passage), frequency related measures, such as fundamental frequency (F0), energy related measures, such as signal-to-noise ratio, and voice quality measures, such as the harmonics-to-noise ratio (HNR). Additionally, Canonical Timing Alignment (CTA; indicated as a percent), can be calculated, which is a number between 0 percent (non-alignment) and 100 percent (perfect alignment), measured as the normalized inverse Levenstein edit distance between words and silence boundaries.

Facial video metrics can be based on facial landmarks generated with, for example, MediaPipe Face Mesh. First, MediaPipe Face Detection is used to determine the (x, y)-coordinates of the face for every video frame. Then, facial landmarks are extracted using MediaPipe Face Mesh. key landmarks can be utilized to compute metrics like the speed of articulators (jaw, lower lip), surface area of the mouth, and eyebrow raises. These landmarks include center and corners of the lips, jaw center, nose tip, center and corners of the eyes, and the center of the eyebrows. Lastly, the features are normalized by dividing them by the inter-caruncular or inter-canthal distance, to handle variability across participant sessions due to position and movement relative to the camera. For visual metrics, functionals (e.g., minimum, maximum, average) are applied to produce one value across all video frames of an utterance. Visual distance metrics are measured in pixels and can be normalized by dividing them by the intercanthal distance (i.e., distance between inner corners of the eyes).

Linguistic metrics are computed for a picture description task only, using the Python package spaCy. The linguistic metrics are based on automatic transcriptions obtained with AWS Transcribe and include lexico-semantic metrics, such as word count, noun rate, and noun-to-verb ratio.

The remotely collected multimodal digital markers extracted by virtual agent 106 can span across an audio domain, a text domain, and/or a video domain, with associated metrics being measured for each utilized domain. For example, multimodal digital markers from an audio domain can include one or more energy metrics, one or more timing metrics, one or more voice quality metrics, and/or one or more frequency metrics. The energy metrics can include, for example, include shimmer (indicated as a percent), intensity (i.e., in decibels), and/or signal-to-noise ratio (i.e., in decibels). Additionally, the timing metrics can include, for example, timing speaking and articulation duration (indicated in seconds), articulation, and speaking rate (measured in words-per-minute), percent pause time (PPT, indicated as a percent) canonical timing agreement (CTA, indicated as a percent), cycle-to-cycle temporal variability (cTV, measured in seconds), syllable rate (i.e., syllables per second), and/or number of syllables. The voice quality metrics can include, for example, voice quality cepstral peak prominence (CPP, measured in decibels), and/or harmonics-to-noise ratio (HNR, measured in decibels). The frequency metrics can include, for example, frequency mean, frequency maximum, minimum fundamental frequency F0 (measured in Hertz), first three formants F1, F2, F3 (measured in Hertz), slope of 2nd formant (measured in Hertz per second), and/or jitter (indicated as a percent).

In another example, multimodal digital markers from a text domain can include one or more lexico-semantic metrics. The lexico-semantic metrics can include, for example, word count, percentage of content words, noun rate, verb rate, pronoun rate, noun-to-verb ratio, noun-to-pronoun ratio, closed class word ratio, and/or idea density.

In another example, multimodal digital markers from a video domain can include one or more mouth (distance) metrics, one or more lip/jaw movement metrics, and/or one or more eyes metrics. The mouth (distance) metrics can include, for example, lip aperture/opening, lip width, mouth surface area, and/or mean symmetry ratio between left and right half of the mouth. The lip/jaw movement metrics can include, for example, velocity, acceleration, jerk, and/or speed of the lower lip and jaw center. The eyes metrics can include, for example, number of eye blinks per second, eye opening, and/or vertical displacement of eyebrows. Of course, it is expressly contemplated that other metrics can be utilized for each respective domain as well. Additionally, it is expressly contemplated that other domains can be utilized as well with associated metrics.

The cloud-based multimodal dialog system can be utilized as virtual agent 106 to collect media recordings from participants who engage in a structured conversation with virtual agent 106. The media recording can be, for example, a video recording. In another example, the media recording can be a combination of a video and audio recording. Additionally, in other examples, it is expressly contemplated that other media recordings can be obtained and utilized as well. To ensure data privacy and protection of personal health information (PHI), the multimodal dialog system is fully compliant with the Health Insurance Portability and Accountability Act (HIPAA) and the General Data Protection Regulation (GDPR). Each participant within first cohort 102 and second cohort 104 is provided with a unique website link to the multimodal dialog system platform, which a participant can access to start the assessment. The assessment can be accessed by any suitable computing device, such as a mobile phone, laptop, or other computing device.

After completing microphone and camera checks to ensure data collection of good quality, participants engage in a conversation with virtual agent 106. The dialog protocol elicits different types of speech samples. For example, one or more of the following tasks can be included in a dialog protocol: read speech (sentence intelligibility test (SIT), 5-15 words; Bamboo reading passage (RP), 99 words), measure of diadochokinesis (DDK, rapidly repeating the syllables "pA-tA-kA"), single breath counting (SBC), and/or free speech in form of a picture description task (PD). During the assessment, virtual agent 106 can ask participants to do the aforementioned tasks. Due to the conversational nature, participants receive feedback (e.g., when they spoke shorter than a predefined threshold for a given task), and virtual agent 106 can provide demonstrations of how a given task should be performed. Participants' audio and video streams are subsequently uploaded and segmented in real-time, and stores in memory 108 as remotely collected multimodal digital markers. After dialog completion, participants are subsequently prompted to fill out the ALSFRS-R scale, the clinical gold standard to capture progression in ALS. Thus, remotely collected multimodal digital markers can be extracted by utilizing a structured conversational dialog with virtual agent 106.

As described above, after remotely collecting multimodal digital markers from first cohort 102 and second cohort 104, the resulting collected multimodal digital markers are stored in memory 108. Memory storing the remotely collected multimodal digital markers from first cohort 102 and second cohort 104 are subsequently passed to feature selection logic 110, which is configured to identify a subset of the multimodal digital markers 112 that are best at capturing differences between first cohort 102 (i.e., the sign onset) and second cohort 104 (i.e., the non-sign onset). In particular, feature selection logic 110 is configured to utilize multicollinearity in the feature selection process to select representative features that can distinguish first cohort 102 from second cohort 104 and identify the optimal multimodal digital markers as a subset 112.

In one example, remotely collected multimodal digital markers 108 include features that are metrics extracted for a specific stimulus or task. For instance, all audiovisual metrics can be extracted by feature selection logic 110 for each utilized task in the assessment provided by virtual agent 106. In this way, feature selection logic is further configured to group the features into clusters, and to identify one or more representative features for each of the clusters. To handle multicollinear features and identify an optimal set of representative features, hierarchical clustering can be applied by feature selection logic 110 (e.g., on Spearman rank-order correlations). A distance threshold to split clusters can be chosen manually to select clusters that represent sensible feature groupings in terms of the domain (e.g. frequency or timing related speech features) or the area of the face (e.g. features pertaining to jaw movement). One example of clustering is shown visually below with respect to FIG. 16.

Next, a representative feature for every cluster can be selected by feature selection logic 110 to form a final feature set, and receiver operating characteristic (ROC) curve analysis can be utilized to determine the area under the ROC curve (AUC) for distinguishing first cohort 102 (e.g., sign onset participants) from second cohort 104 (e.g., non-sign onset participants) for every individual feature. In this way, feature selection logic 110 is configured to identify the subset of remotely collected multimodal digital markers 112 that are best at capturing differences between the sign onset and the non-sign onset. In one example, validation via the ROC curve analysis is implemented with sklearn's Stratified-GroupKFold function, where the samples were stratified by the class label non-bulbar/bulbar onset. One such example of clustering and the selected representative features are shown below with respect to FIG. 17.

In one example, the clusters grouped by feature selection logic 110 can include timing: duration and rates, temporal diadochokinesis (DDK) measures, timing alignment, duration and word count for picture description (PD), eyebrow displacement, pause time, lip width, voice quality (read/free speech), cepstral peak prominence (CPP), voice quality for single breath counting (SBC) and DDK, lip aperture, mouth surface area, eye opening measures, content and closed class words, min. and mean F0, jaw center (JC) velocity for sentence intelligibility test (SIT), duration measures for SBC and DDK, JC velocity for reading passage (RP), verb/noun/pronoun rates, lower lip (LL) velocity, JC velocity, JC velocity, max. F0 and F0 stdev., LL velocity for read speech, JC velocity for DDK, LL velocity for DDK, LL velocity for SBC, and/or mouth symmetry ratio. Additionally, in one example, the representative features identified by feature selection logic 110 can include speaking duration (RP), cycle-to-cycle temporal variability (cTV) (DDK), canonical timing agreement (CTA) (RP), word count (PD), max. eyebrow displacement (SIT), percent pause time (PPT) (SIT), max. lip width (RP), harmonics-to-noise ratio (HNR) (SIT), CPP (RP), HNR (DDK), mean lip aperture (SIT), max. eye opening (SIT), closed class word ratio (PD), mean F0 (RP), max. JC velocity down (SIT), number of syllables (DDK), max. JC velocity up (RP), pronoun rate (PD), max. LL jerk up (PD), max. JC velocity down (PD), mean JC speed (SBC), max. F0 (SIT), mean LL speed (SIT), max. JC velocity down (DDK), mean LL jerk (DDK), max. LL speed (SBC), and/or mean mouth symmetry ratio (RP). Additionally, it is expressly contemplated that other clusters can be formed by feature selection logic 110 as well, and associated other different representative features can also be identified by feature selection logic 110.

Additionally, in one example, the identified subset of remotely collected multimodal digital markers 112 can include speaking duration (RP), cycle-to-cycle temporal variability (cTV) (DDK), canonical timing agreement (CTA) (RP), word count (PD), max. eyebrow displacement (SIT), percent pause time (PPT) (SIT), max. lip width (RP), harmonics-to-noise ratio (HNR) (SIT), CPP (RP), HNR (DDK), mean lip aperture (SIT), max. eye opening (SIT), closed class word ratio (PD), mean F0 (RP), max. JC velocity down (SIT), number of syllables (DDK), and/or max. JC velocity up (RP). Of course, it is expressly contemplated that a different subset of remotely collected multimodal digital markers can be utilized as well.

As shown in FIG. 11B, the resulting subset of remotely collected multimodal digital markers 112 is passed to both responsiveness determination logic 114 and time to detect change determination logic 116. Each of responsiveness determination logic 114 and time to detect change determination logic 116 are described below in turn.

Responsiveness determination logic 114 is configured to determine a responsiveness parameter 118 that specifies how a rate of change in the identified subset of the multimodal digital markers differs between first cohort 102 (i.e., the sign onset) and second cohort 104 (i.e., the non-sign onset). In particular, responsiveness determination logic 114 is further configured to determine responsiveness parameter 118 using growth curve models (GCMs). GCMs provide a linear fit for a non-linear mixed effects model to estimate the trajectory of a metric over time with random slopes and intercepts for each participant. Growth curve models produce estimates of smoothed trajectories of change over time by using observed repeated measures of each individual, making it an optimal statistical tool to be utilized. GCM curves for distinct cohorts can help identify differences in the longitudinal trajectory of measures in the two cohorts. For the responsiveness analysis by responsiveness determination logic 114, first cohort 102 and second cohort 104 are selected for growth curve modelling based on their association with the sign onset and non-sign onset, respectively. For each feature, the rate of change (e.g., slope of the linear fit) can be analyzed by responsiveness determination logic 114 between first cohort 102 and second cohort 104. For example, for each feature that demonstrates differences between first cohort 102 and second cohort 104, the responsiveness parameter can be determined based on two ways. First, responsiveness parameter 118 can be determined by responsiveness determination logic 114 based on a statistical utility that specifies the time taken in weeks to detect disease deterioration greater than a standard error of the mean for a given cohort. Second, responsiveness parameter 118 can be determined by responsiveness determination logic 114 based on a clinical utility that specifies the time taken in weeks to detect disease deterioration greater than a given minimal clinically-important difference (MCID) value. Of course, it is expressly contemplated that the two aforementioned ways of determining responsiveness parameter 118 are only for the purposes of example, and it is expressly contemplated that other ways of determining responsiveness parameter 118 can be utilized as well.

Based on responsiveness parameter 118, the system is further configured to identify from an identified subset of multimodal digital markers, a further subset of multimodal digital markers that show a significantly different change over time between first cohort 102 with the sign onset and second cohort 104 with the non-sign onset. For instance, from remotely collected multimodal digital markers 112, a further subset of multimodal digital markers can be identified including RP CTA (indicated as a percent), PD word count (words), RP speaking duration (seconds), RP mean F0 (Hertz (Hz)), DDK HNR (Decibels (dB)), RP CPP (dB), RP max. lip width, SIT PPT (indicated as a percent), and/or SIT HNR (dB).

Time to detect change determination logic 116 is configured to determine a time to detect change parameter 120 that specifies a time period required to detect a meaningful change in the identified subset of the multimodal digital markers 112 from disease onset in first cohort 102 and second cohort 104. In particular, the time to detect change parameter 120 can be determined by time to detect change determination logic 116 between each of first cohort 102 and second cohort 104. Time to detect change logic 116 is further configured to identify the most responsive digital markers that show the shortest time to detect a chance that is statistically and clinically relevant. For instance, in the above example where the further subset of multimodal digital markers can is identified including RP CTA (indicated as a percent), PD word count (words), RP speaking duration (seconds), RP mean F0 (Hertz (Hz)), DDK HNR (Decibels (dB)), RP CPP (dB), RP max. lip width, SIT PPT (indicated as a percent), and/or SIT HNR (dB), time to detect change logic 116 can identify, based on time to detect change parameter 120, that RP CTA and PD word count are most responsive digital markers that showed the shortest time to detect a change that was statistically and clinically relevant. Examples of time to detect change parameter determination are discussed in more detail below with respect to FIG. 18.

As shown in FIG. 11B, the determined responsiveness parameter 118 and time to detect change parameter 120 are passed to sample size effect determination logic 122. Sample size effect determination logic 122 is configured to determine how responsiveness parameter 118 and time to detect change parameter 120 change depending on a sample size of first cohort 102 and second cohort 104. For example, sample size effect determination logic 122 can analyze the relationship between responsiveness parameter 118 and time to detect change parameter 120 at varying sample sizes over a set number of iterations. In particular, a growth curve model can be applied to each iteration, and a mean responsiveness for a given sample size can be calculated by taking the average slope for each cohort across the total utilized iterations. In one example, sample sizes of thirty, twenty-five, twenty, fifteen, and ten participants are randomly sampled one hundred times from first cohort 102 and second cohort 104, and GCMs are applied for each of the one hundred total iterations. Upon determining how responsiveness parameter 118 and time to detect change parameter 120 change depending on sample size of first cohort 102 and second cohort 104, the resulting sample size effect 124 is generated.

In one example, sample size effect determination logic 122 is further configured to determine the responsiveness stability of the identified subset of multimodal digital markers relative to a utilized sample size. For example, sample size effect determination logic 122 can determine that the responsiveness of the identified subset of the multimodal digital markers remains relatively stable even with small sample sizes.

As shown in FIG. 11C subset of the remotely collected multimodal digital markers 112 are also passed to sensitivity determination logic 128. Sensitivity determination logic 128 is configured to determine a sensitivity parameter 130 that specifies whether the identified subset of the multimodal digital markers detect disease deterioration during intervals of time when no changes are reported in an external gold standard. In particular, one or more metrics indicating external gold standard(s) are also passed to sensitivity determination logic 128 to determine sensitivity parameter 130. For example, the external gold standard(s) can be one or more ALSFRS-R metrics. In this example, sensitivity determination logic 128 is configured to identify when there notable changes in the multimodal digital markers at points where there have been no reported changes in the ALSFRS-R metrics. For instance, sensitivity determination logic 128 may be configured to identify that the RP CTA, the PD word count, the RP speaking duration, and the RP CPP showed a statistically significant change over time even when the external gold standard indicated no clinical change in the first cohort with the sign onset. In this instance, sensitivity parameter 130 is output that specifies that the identified subset of the multimodal digital markers detect disease deterioration during intervals of time when no changes are reported in the external gold standard.

Sensitivity determination logic 128 is further configured to determine which of the identified subset of multimodal digital markers 112 are meaningful using an MCID parameter. The MCID is the smallest domain-specific change that is considered to be clinically relevant. It can be quantified as a threshold for a change corresponding to clinical improvement or deterioration and is tied to an external anchor, which is considered to be a clinical gold standard, (e.g., ALSFRS-R scale). MCID can be calculated for all features for a corresponding one-point change on the ALSFRS-R speech question where participants are asked to rate their speech on a scale. The scale can include, for example, values corresponding to normal speech processes, detectable speech disturbance, intelligible with repeating, speech combined with nonvocal communication, and/or loss of useful speech. In one example, MCID can be derived by using data-driven ROC analysis. The point representing maximum sensitivity and specificity on an ROC curve is determined as the optimal cutpoint corresponding to the MCID value. MCID calculation can be performed using the rpy2 package in Python along with the pROC and ROCR packages in R.

Sensitivity determination logic 128 is further configured to determine sensitivity parameter 130 using GCMs. GCMs provide a linear fit for a non-linear mixed effects model to estimate the trajectory of a metric over time with random slopes and intercepts for each participant. Growth curve models produce estimates of smoothed trajectories of change over time by using observed repeated measures of each individual, making it an optimal statistical tool to be utilized. GCM curves for distinct cohorts can help identify differences in the longitudinal trajectory of measures in the two cohorts. For the sensitivity analysis by sensitivity determination logic 128, first cohort 102 and second cohort 104 are selected for growth curve modelling based on their association with the sign onset and non-sign onset, respectively. A feature was determined to be sensitive if the slope of the GCM for pALS varied as compared to a slope of participants from a control cohort. The advantage of comparing the trajectory of metrics in 'clinically-stable' pALS with that in controls is that it will demonstrate a difference in slopes over any learning effects.

Figure 12:
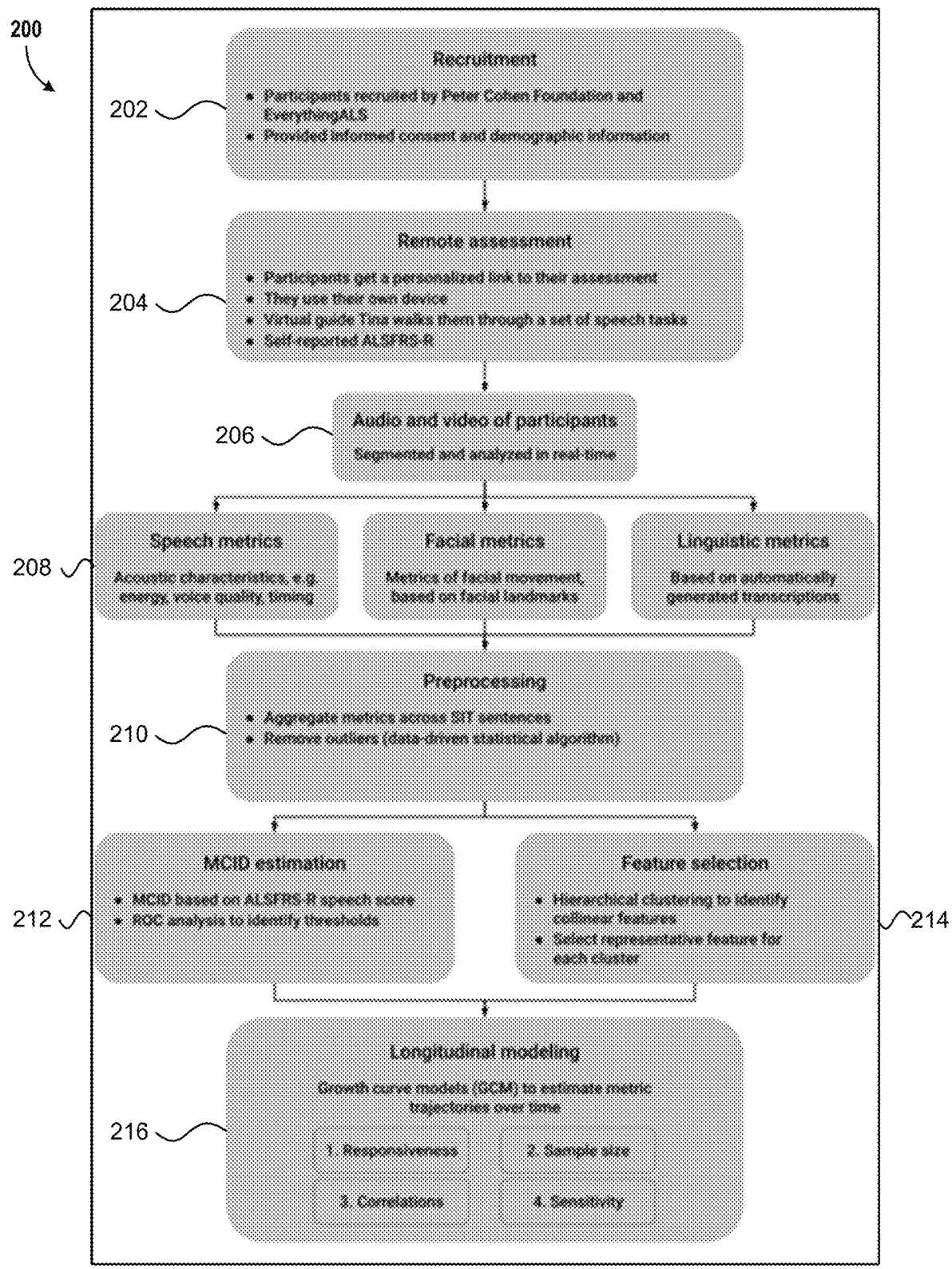
FIG. 12 is a flowchart showing one example operation of the design and modeling procedure.

FIG. 12 is a flowchart showing one example operation of the design and modeling procedure. Operation 200 begins at block 202 where participants are recruited for assessment. As shown at block 202, participants may be recruited by, for example, Everything ALS and the Peter Cohen Foundation. All participants are provided informed consent upon recruitment, prior to their first assessment on the assessment platform.

Operation 200 proceeds at block 204 where participants begin remote assessment. As indicated above with respect to FIGS. 11A, 11B, 11C, a cloud-based multimodal dialog system is used to collect video recordings from participants who engaged in a structured conversation with a virtual agent (Tina), such as virtual agent 106 described above. To ensure data privacy and protection of personal health information (PHI), the assessment service is fully compliant with the Health Insurance Portability and Accountability Act (HIPAA) and the General Data Protection Regulation (GDPR; European Union). Each participant is provided with a unique website link to the assessment platform, which they can click on to start the assessment using a browser and device of their choice.

After completing microphone and camera checks to ensure data collection of good quality, participants engage in a conversation with the virtual agent, as indicated by block 206. In one example data collection, the following tasks can be included: (a) read speech (sentence intelligibility test (SIT), 5-15 words; Bamboo reading passage (RP), 99 words), (b) measure of diadochokinesis (DDK, rapidly repeating the syllables/pAtAkA/), (c) single breath counting (SBC), and (d) free speech in form of a picture description task (PD). During the assessment, the virtual agent asks participants to do the aforementioned tasks. Due to the conversational nature, participants receive feedback (e.g., when they spoke shorter than a predefined threshold for a given task), and Tina can provide demonstrations of how a task should be performed. Participants' audio and video streams are uploaded to the cloud and segmented in real-time for downstream analysis. After dialog completion, participants were asked to fill out the ALS functional rating scale revised (ALSFRS-R), the standard clinical scale to capture progression in ALS.

Operation 200 proceeds at block 208 where the audio and video of participants are segmented based on speech metrics, facial metrics, and linguistic metrics. The multimodal dialog platform is equipped with analytics modules that automatically extract metrics to capture information from acoustic (energy, timing, voice quality, spectral), facial (articulatory kinematics, range of motion, eye and facial movement), motoric (finger tapping kinematics) and textual (lexico-semantic, sentiment) domains during the different tasks. FIG. 15 provides an overview of the extracted metrics.

Praat (v6.2.17) and the Montreal Forced Aligner (v2.0.0.a22) are utilized to extract speech metrics, including timing measures, such as percentage of pause time (PPT; proportion of the total duration of all pauses to the total duration of the utterance), rate measures such as speaking rate (the total number of words in the passage (99) divided by the speaking duration, or time taken to read the Bamboo passage), frequency related measures, such as fundamental frequency (F0), energy related measures, such as signal-to-noise ratio, and voice quality measures, such as the harmonics-to-noise ratio (HNR). We also computed Canonical Timing Alignment (CTA; indicated as a percent), a number between 0 percent (non-alignment) and 100 percent (perfect alignment), measured as the normalized inverse Levenstein edit distance between words and silence boundaries (here the participant's predicted word-level timing information, derived using the Montreal Forced Aligner is compared to a canonical production by virtual agent 106).

Facial video metrics are based on facial landmarks generated with MediaPipe Face Mesh. First, MediaPipe Face Detection, which is based on BlazeFace, is used to determine the (x, y)-coordinates of the face for every video frame. Then, facial landmarks are extracted using MediaPipe Face Mesh. Fourteen key landmarks are utilized to compute metrics like the speed of articulators (jaw, lower lip), surface area of the mouth, and eyebrow raises. These landmarks include center and corners of the lips, jaw center, nose tip, center and corners of the eyes, and the center of the eyebrows. Lastly, the features are normalized by dividing them by the inter-caruncular or inter-canthal distance, to handle variability across participant sessions due to position and movement relative to the camera.

Linguistic metrics are computed for the picture description task only, using the Python package spaCy. They are based on automatic transcriptions obtained with AWS Transcribe and include lexico-semantic metrics, such as word count, noun rate, and noun-to-verb ratio.

Operation 200 proceeds at block 210 where the one or more speech metrics, facial metrics, and/or linguistic metrics are preprocessed. Generally, every metric is computed for each task of the assessment on an utterance level, e.g., speaking rate for the reading passage, or speaking duration for the SBC task. As used herein, these task-metric combinations are referred to as "features". For the SIT task, metrics are aggregated across six SIT sentences by taking the mean values over these utterances (i.e., speaking rate for SIT denotes the average speaking rate across the six sentences).

To remove outlier values from speech and facial features, a distribution-based outlier detection algorithm is employed. Possible reasons for outlier occurrence include high-intensity background noise, bad lighting conditions, or incorrectly performed tasks. First, all feature values that are more than five standard deviations away from the population mean are removed. These are considered extreme outliers, which potentially skew the distribution mean. Such extreme events can happen when the recorded data is corrupted, for example through a poor network connection. The value of five standard deviations was empirically chosen after carefully analyzing the data distributions. Then, the mean is re-computed and values outside+3 standard deviations are flagged as outliers and removed from any further analysis. Finally, for the feature selection procedure discussed below at block 214, all features are normalized to zero mean and unit variance.

Operation 200 proceeds at blocks 212 and 214, which will be described herein in turn. At block 212, MCID is estimated. To clearly define what feature changes count as clinically meaningful, the concept MCID is utilized. The MCID is the smallest domain-specific change that is considered to be clinically relevant. It can be quantified as a threshold for a change corresponding to clinical improvement or deterioration and is tied to an external anchor, which is considered to be a clinical gold standard, the ALSFRS-R speech question in this case. MCID is calculated for all features for a corresponding one-point change on the ALSFRS-R speech question where participants are asked to rate their speech on the following scale: normal speech processes, detectable speech disturbance, intelligible with repeating, speech combined with nonvocal communication, and loss of useful speech.

One approach to derive the MCID is using data-driven ROC analysis, which is also applied. The point representing maximum sensitivity and specificity (closest to the top left corner) on an ROC curve is determined as the optimal cutpoint corresponding to the MCID value. MCID calculation is performed using the rpy2 package in Python along with the pROC and ROCR packages in R. The classes being discriminated were pALS who exhibited a one-point decline in their ALSFRS-R speech score and those who did not show any change in their ALSFRS-R speech score. For each pALS, adjacent sessions (with at least 14 days between sessions) are considered to calculate the change in every feature from the first to the second session. For pALS in the one-point decline class, only those adjacent sessions were taken into account where the decline is observed.

At block 214, feature selection is determined. All audiovisual metrics are extracted for each of the five speech tasks in the protocol. Considering all valid task-metric combinations as individual features results in a very large number of features. To handle multicollinear features and identify a good set of representative features, hierarchical clustering is applied on the Spearman rank-order correlations. For this feature clustering approach, only healthy controls' data is considered in order to avoid data leakage in the experimental design-note that all subsequent analyses focus on patient data only- and because data from healthy controls is most representative of normative feature ranges and correlations between features. A distance threshold of 1.0 to split clusters is chosen manually to select clusters that represent sensible feature groupings in terms of the domain (e.g. frequency or timing related speech features) or the area of the face (e.g. features pertaining to jaw movement). In one example, this threshold results in twenty-seven clusters.

Next, a representative feature for every cluster is selected to form the final feature set. Receiver operating characteristic (ROC) curve analysis is used in a 5-fold cross validation setup to determine the area under the ROC curve (AUC) for distinguishing sign onset participants from non-sign onset participants (for every individual feature). 5-fold cross validation is used to ensure generalizability. This was implemented with sklearn's Stratified-GroupKFold function, where the samples were stratified by the class label non-bulbar/bulbar onset, and it was ensured that there is no overlap of a participant's data between training and test folds. FIG. 17 shows the clusters and the selected representative features. To further filter features, a minimum threshold is imposed for the ROC-AUC. Only features with an AUC>0.65 and for which the MCID was larger than the standard error of the mean (SE) are considered in the longitudinal analysis.

Operation 200 proceeds at block 216 where longitudinal modeling is applied. Responsiveness and sensitivity of features over time are evaluated using growth curve models (GCMs), which provide a linear fit for a non-linear mixed effects model to estimate the trajectory of a metric over time with random slopes and intercepts for each participant. Growth curve models produce estimates of smoothed trajectories of change over time by using observed repeated measures of each individual. GCM fitting is performed in R. GCM curves for distinct cohorts can help identify differences in the longitudinal trajectory of measures in the two cohorts. In one example, more than 80% of participants had at least 3 repeated measures, thus minimizing any impact of variability in the number of sessions per participant on the growth curve models.

For the responsiveness analysis, the two cohorts chosen for growth curve modeling are sessions from pALS with sign onset and those from pALS with non-sign onset. First, for every selected feature, the rate of change (or slope of the linear fit) is examined to determine whether it is significantly different between the two cohorts. Then, for those features that showed differences, responsiveness is evaluated in two ways: (i) the time taken in weeks to detect deterioration greater than the standard error of the mean for the cohort (statistical utility) and (ii) the time taken in weeks to detect deterioration greater than the MCID value (clinical utility).

To investigate the relationship between responsiveness and sample size of the participant cohort, sample sizes of 30, 25, 20, 15 and 10 participants are randomly sampled 100 times, without replacement, from both cohorts. GCMs are performed for each of these 100 iterations. Mean responsiveness for a sample size is calculated by taking the average slope for each cohort across the 100 iterations.

To explore the relationship between responsive metrics and the ALSFRS-R scale, Spearman correlations are performed between metrics that showed differences in slopes of bulbar and non-bulbar onset pALS and the ALSFRS-R total score, ALSFRS-R bulbar subscore and the ALSFRS-R speech question.

For sensitivity analysis, the two cohorts analyzed are sessions from healthy controls and all contiguous pALS sessions with a speech score of 3. pALS sessions with a speech score of 3 are analyzed because these pALS are deemed to exhibit bulbar impairment but still had speech that was intact enough for objective analysis. A feature is determined to be sensitive if the slope of the GCM for pALS with a steady speech score of 3 varied as compared to the slope of participants from the control cohort with a steady speech score of 4. Note that longitudinal data may be confounded by the presence of learning effects due to the repetition of the same tasks over time. For example, in the case of the Bamboo passage, familiarity with the words in the passage may lead to a decreased speaking duration. The advantage of comparing the trajectory of metrics in 'clinically-stable' pALS with that in controls is that it will demonstrate a difference in slopes over any learning effects (assuming the learning effects are equal across cohorts).

Performance Results as Objective Indicia of Inventiveness and Non-Obviousness

All analyses were performed using Python (v3.10) and R (v4.3.1). The following open-source Python libraries were used: Pandas (v1.5.3), Numpy (v1.24.3), scikit-learn (v1.2.2), Matplotlib (v3.7.1), spaCy (v3.5.3), and SciPy (v1.10.1). The following R packages were used: ROCR (v1.0.11), pROC (v1.18.2), ggplot2 (v3.4.4), nlme (v3.1.162), and the rpy2 interface (v3.5.13).

FIG. 13 is a table showing one example of participant statistics used for identifying efficacious markers. FIG. 13 summarizes participant statistics in a study and provides information on the ALSFRS-R scores at baseline (participants' first session). Data was collected between 2020 Nov. 3 and 2023 Oct. 6 from 143 pALS (70 female, mean age+standard deviation=60.4±10.2 years, Bulbar onset: n=36, Non-Bulbar onset: n=107) and 135 age and sex-matched controls (71 female, mean age+standard deviation=59.9±10.3 years). For age matching, a tolerance threshold of ±3 years was set. A total number of 6,816 recording sessions were conducted (3,388 sessions from pALS-598 bulbar onset and 2,790 non-bulbar onset- and 3,428 sessions from healthy controls). Out of 3,388 sessions from pALS, the ALSFRS-R total score was available for 1,879 sessions. As shown in FIG. 13, "F" corresponds to the number of female participants. "M" corresponds to the number of male participants. "BL" corresponds to baseline (first session) values. The time span first-to-last is the mean number of days between participants' first and last session in the data collection. The large variation of the number of samples per participant in this data collection is due to the continuous and ongoing recruitment of new participants in this study. Statistics are reported as median; mean (standard deviation) for ALSFRS-R scores, and as mean (standard deviation) otherwise.

Figure 14:
FIG. 14 is a diagram showing one example operation of obtaining multimodal digital markers.

FIG. 14 is a diagram showing one example operation of obtaining multimodal digital markers. Operation 400 begins with a virtual guide prompting a user to perform one or more associated tasks. In particular, after completing microphone and camera checks to ensure data collection of good quality, participants engage in a conversation with the virtual guide. The virtual guide can be, for example, virtual agent 106 described above with respect to FIGS. 11A, 11B, 11C. The dialog protocol elicits different types of speech samples. For example, the following tasks may be included: (a) read speech (sentence intelligibility test (SIT), 5-15 words; Bamboo reading passage (RP), 99 words), (b) measure of diadochokinesis (DDK, rapidly repeating the syllables/pAtAkA/), (c) single breath counting (SBC), and (d) free speech in form of a picture description task (PD). During the assessment, the virtual agent asks participants to do the aforementioned tasks. Due to the conversational nature, participants receive feedback (e.g., when they spoke shorter than a predefined threshold for a given task), and the virtual agent can provide demonstrations of how a task should be performed. Participants' audio and video streams are uploaded to the cloud and segmented in real-time for downstream analysis. After dialog completion, participants were asked to fill out the ALS functional rating scale-revised (ALSFRS-R), the standard clinical scale to capture progression in ALS. As indicated above, the dialog platform is equipped with analytics modules that automatically extract metrics to capture information from acoustic (energy, timing, voice quality, spectral), facial (articulatory kinematics, range of motion, eye and facial movement), motoric (finger tapping kinematics) and textual (lexico-semantic, sentiment) domains during the different tasks. For example, from the audio and/or voice recordings obtained during the assessment, speech, facial, cognitive, linguistic, limb-motor, and/or eye-gaze metrics can be extracted.

FIG. 15 is a table showing an overview of extracted metrics from remotely collected multimodal digital markers. For visual metrics, functionals (minimum, maximum, average) are applied to produce one value across all video frames of an utterance. Visual distance metrics are measured in pixels and are normalized by dividing them by the intercanthal distance (distance between inner corners of the eyes) for each participant. As shown, the remotely collected multimodal digital markers extracted by the virtual agent can span across an audio domain, a text domain, and/or a video domain, with associated metrics being measured for each utilized domain. For example, multimodal digital markers from an audio domain can include one or more energy metrics, one or more timing metrics, one or more voice quality metrics, and/or one or more frequency metrics. The energy metrics can include, for example, include shimmer (indicated as a percent), intensity (i.e., in decibels), and/or signal-to-noise ratio (i.e., in decibels). Additionally, the timing metrics can include, for example, timing speaking and articulation duration (indicated in seconds), articulation, and speaking rate (measured in words-per-minute), percent pause time (PPT, indicated as a percent) canonical timing agreement (CTA, indicated as a percent), cycle-to-cycle temporal variability (cTV, measured in seconds), syllable rate (i.e., syllables per second), and/or number of syllables. The voice quality metrics can include, for example, voice quality cepstral peak prominence (CPP, measured in decibels), and/or harmonics-to-noise ratio (HNR, measured in decibels). The frequency metrics can include, for example, frequency mean, frequency maximum, minimum fundamental frequency F0 (measured in Hertz), first three formants F1, F2, F3 (measured in Hertz), slope of 2nd formant (measured in Hertz per second), and/or jitter (indicated as a percent).

In another example, multimodal digital markers from a text domain can include one or more lexico-semantic metrics. The lexico-semantic metrics can include, for example, word count, percentage of content words, noun rate, verb rate, pronoun rate, noun-to-verb ratio, noun-to-pronoun ratio, closed class word ratio, and/or idea density.

In another example, multimodal digital markers from a video domain can include one or more mouth (distance) metrics, one or more lip/jaw movement metrics, and/or one or more eyes metrics. The mouth (distance) metrics can include, for example, lip aperture/opening, lip width, mouth surface area, and/or mean symmetry ratio between left and right half of the mouth. The lip/jaw movement metrics can include, for example, velocity, acceleration, jerk, and/or speed of the lower lip and jaw center. The eyes metrics can include, for example, number of eye blinks per second, eye opening, and/or vertical displacement of eyebrows.

Figure 16:
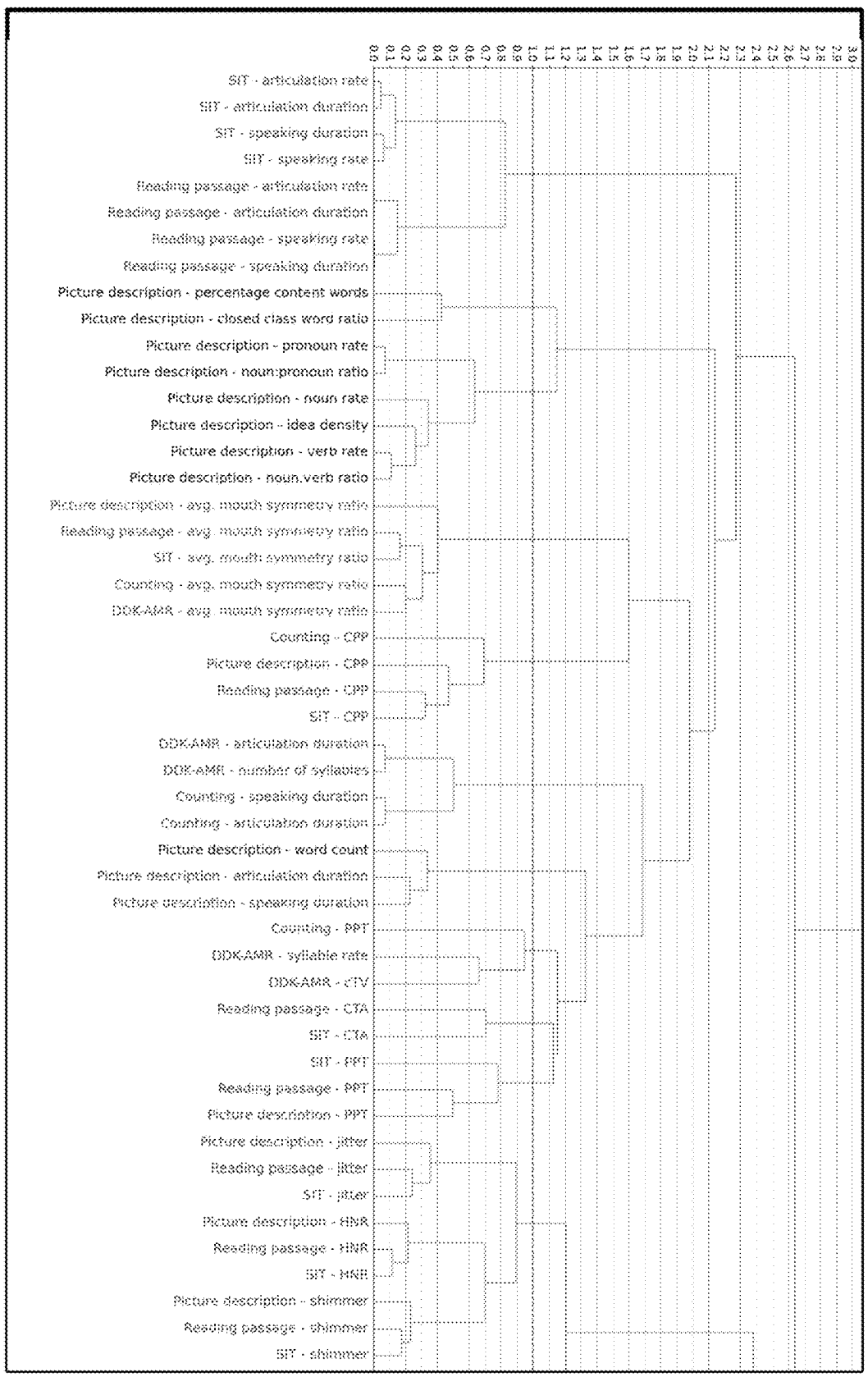
FIG. 16 is a chart showing an example dendrogram for visualizing feature clusters of varying features.

FIG. 16 is a chart showing an example dendrogram for visualizing feature clusters of varying features. In the example shown in FIG. 16, acoustic, linguistic, and facial features are clustered. The dashed line shows the distance threshold for splitting the clusters. As shown, FIG. 16 provides a chart for visually interpreting and inspecting formed feature clusters. A distance threshold of 1.0 to split clusters was chosen manually to select clusters that represent sensible feature groupings in terms of the domain (e.g. frequency or timing related speech features) or the area of the face (e.g. features pertaining to jaw movement). This threshold resulted in 27 clusters.

FIG. 17 is a table showing resulting feature clusters from hierarchical clustering and the corresponding selected representative features. FIG. 17 shows the clusters and the selected representative features. To further filter features, a minimum threshold for the ROC-AUC was imposed. Only features with an AUC>0.65 and for which the MCID was larger than the standard error of the mean (SE) were considered in the longitudinal analysis. AUC represents the mean AUC for distinguishing bulbar onset and non-bulbar onset pALS samples across five cross validation folds. "Resp. p" are the p-values of the responsiveness analysis and an asterisk indicates features that showed signal in the sensitivity analysis. "LL" corresponds to lower lip, "JC" corresponds to jaw center, "RP" corresponds to reading passage, "DDK" corresponds to diadochokinesis, "PD" corresponds to picture description, "SBC" corresponds to single breath counting, and "SIT" corresponds to sentence intelligibility test.

FIG. 18 is a table showing resulting metric responsiveness for both bulbar and non-bulbar onsets. Out of the 17 features selected, 9 features showed differences in slopes between bulbar onset and non-bulbar onset pALS with the bulbar onset cohort exhibiting a steeper slope, as shown below in FIG. 20. Details of the slopes per cohort and responsiveness in terms of time to detect change are also found in FIG. 18. RP speaking duration was found to be the measure with the most responsive statistical utility (2.11 weeks in pALS with bulbar onset). When both statistical and clinical utility are taken into account, RP CTA was the most responsive measure in both cohorts. RP CTA showed statistical and clinical utility in detecting changes in bulbar onset pALS within less than 4 weeks and in non-bulbar onset pALS within 9 weeks. PD word count also seemed responsive in detecting changes in bulbar onset pALS within less than 11 weeks and in non-bulbar onset pALS within 9 weeks. The shorter duration in the non-bulbar onset cohort is due to an increase in word count over time. However, the bulbar onset cohort shows a sharp decrease in PD word count over time despite any learning effect, thus capturing the rapid decline of articulatory and perhaps respiratory function. RP speaking duration demonstrated good responsiveness in detecting statistical changes in both cohorts and clinical change in the bulbar onset cohort. However, when it comes to detecting clinical change in the non-bulbar onset cohort, it takes 23.5 weeks.

Mean responsiveness of RP speaking duration, PD word count, RP CTA and RP mean F0 remains stable, with narrow confidence intervals, even with sample sizes as low as 15 per cohort, as shown in FIGS. 11A, 11B, 11C. However, it is observed that the uncertainty about this estimate generally increases as the sample size decreases. For all other features, the number of weeks required to detect a statistical and clinical change in the non-bulbar cohort is either unstable or too large to be of any clinical utility. Surprisingly, for some of the metrics, responsiveness was greater at a sample size of 10 than that of 15.

Certain speech metrics (like RP speaking duration, RP CTA and SIT PPT) showed moderate to strong correlations with the ALSFRS-R speech question score and the ALSFRS-R bulbar subscore but not the ALSFRS-R total score, as shown in more detail in FIG. 12.

FIG. 19 is a table showing corresponding metric sensitivity. As shown, four features were sensitive enough to show a longitudinal change before any change in the ALSFRS-R speech score of patients from three when compared to controls. These features were: RP speaking duration, PD word count, RP CPP and RP CTA. However, for three of these four features (RP speaking duration, PD word count and RP CTA), a learning effect in controls can be observed through the negative slope for RP speaking duration and RP CTA and a positive slope for PD word count. Since clinical deterioration of speech in controls is not expected, any changes in features can be attributed to familiarization with the task or learning effects. Note that the slope for CTA is negative in controls because an increase in speaking rate would reduce the CTA value because the elicitation will be faster than the canonical elicitation of the reading passage. Differences between controls and pALS were observed despite the presence of these learning effects. In FIG. 19, controls had a slope significantly different from zero for metrics with an asterisk next to them. pALS had a slope significantly different from controls for metrics with two asterisks next to their p-value of difference.

Figure 20:
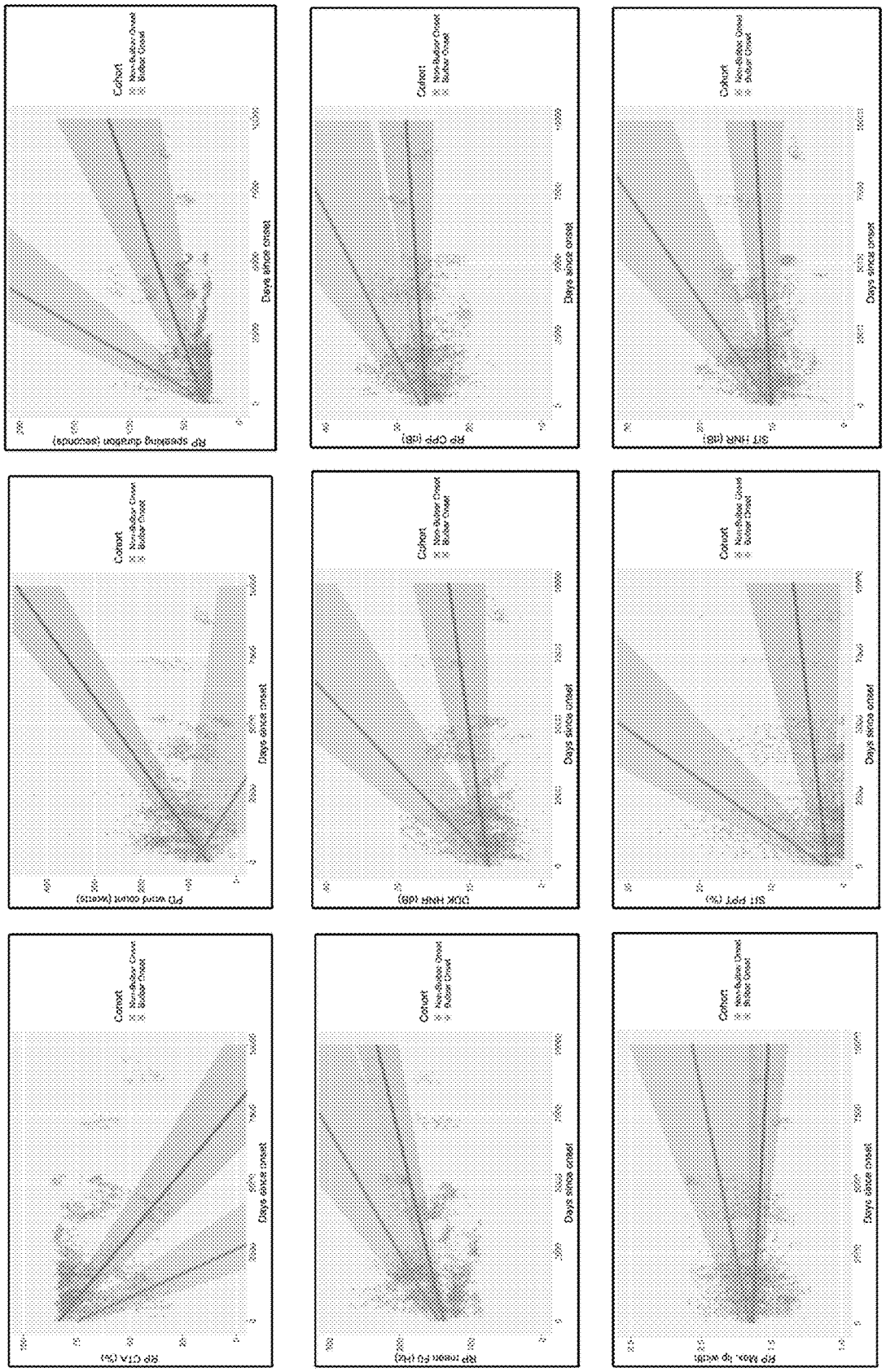
FIG. 20 is a plurality of growth curve model charts showing rates of change for sign onsets as compared to non-sign onsets.

FIG. 20 is a plurality of growth curve model charts showing rates of change for bulbar onsets as compared to non-bulbar onsets. Rates of change for bulbar onset pALS are indicated in blue, and non-bulbar onset pALS is indicated in red. The cohort-specific lines in the growth curve model charts of FIG. 20 represent the average intercept and sclope across all participants in the respective cohorts. Each data point represents a session. As shown, of the 17 features selected, 9 features showed differences in slopes between bulbar onset and non-bulbar onset pALS with the bulbar onset cohort exhibiting a steeper slope.

Figure 21:
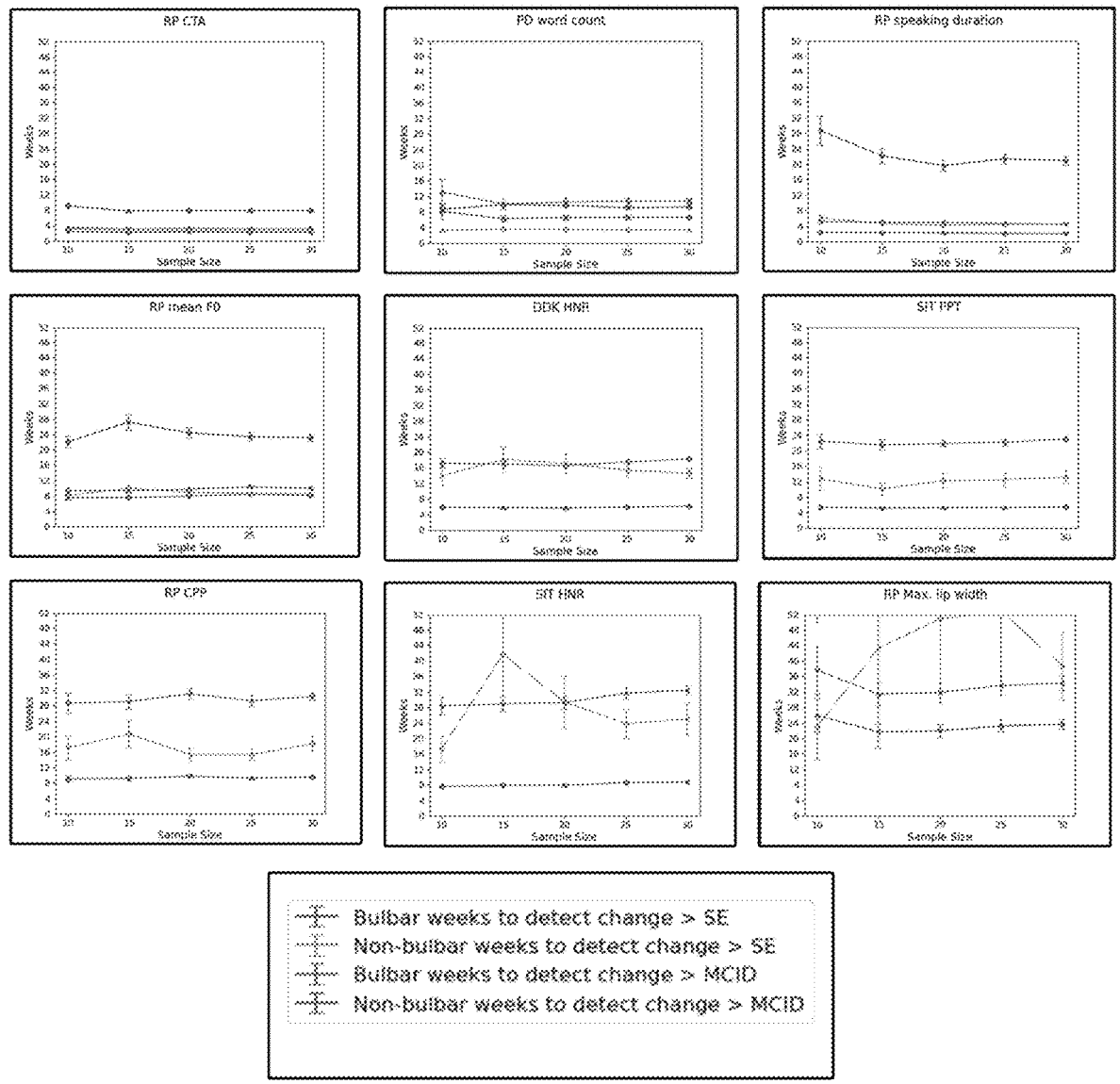
FIG. 21 is a plurality of charts showing time required to detect metric change as a function of sample size.

FIG. 21 is a plurality of charts showing time required to detect metric change as a function of sample size. In particular, FIG. 21 shows the weeks required to detect a change greater than SE and MCID as a function of sample size. For these plots, the vertical limit of the y-axis was set to 52 weeks. As shown, mean responsiveness of RP speaking duration, PD word count, RP CTA and RP mean F0 remains stable, with narrow confidence intervals, even with sample sizes as low as fifteen per cohort.

Figure 22:
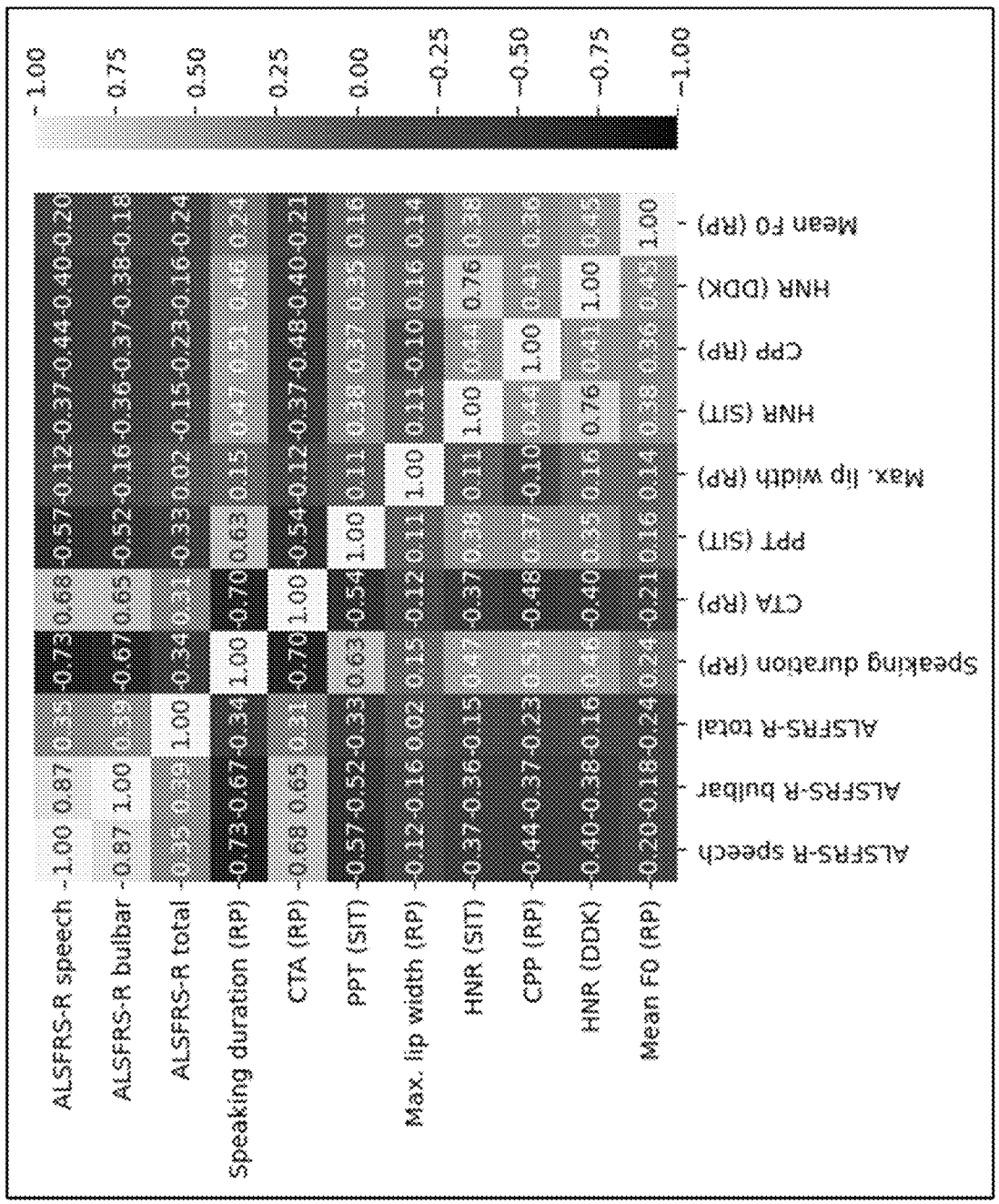
FIG. 22 is a chart showing a correction matrix indicating the correlation between responsive metrics and current clinical gold standard scores.

FIG. 22 is a chart showing a correction matrix indicating the correlation between responsive metrics and current clinical gold standard scores. In particular, FIG. 22 is a correlation matrix with Spearman's values indicating the correlation between responsive metrics and ALSFRS-R scores. As shown, certain speech metrics (like RP speaking duration, RP CTA and SIT PPT) showed moderate to strong correlations with the ALSFRS-R speech question score and the ALSFRS-R bulbar subscore but not the ALSFRS-R total score.

As shown by FIGS. 15-22, four speech features (RP CTA, PD word count, RP speaking duration and RP CPP) also showed a statistically significant change over time even when the clinical gold standard indicated no clinical change in bulbar-impaired pALS. For this, those with pALS were chosen who perceived their speech to be impaired, i.e., a score of 3 on the ALSFRS-R speech question. Healthy controls showed a learning effect over time for three of these four features (a slope statistically different from 0): RP speaking duration, PD word count, RP CTA. Under the assumption that pALS and controls exhibit similar learning effect rates, progression in pALS was significantly different as compared to controls, indicating that these metrics are more sensitive than the clinical gold standard ALSFRS-R at detecting speech deterioration. Thus, it is determined that the longitudinal trajectories of certain digital speech markers are useful in distinguishing between persons with bulbar onset ALS and non-bulbar onset ALS. These trajectories suggest that clinical change associated with bulbar decline could be detected in a matter of a few weeks in pALS. Among the markers investigated, the timing alignment of read speech as compared to a canonical reading of the passage was the most responsive to bulbar decline. This responsiveness holds true even at low sample sizes. Additionally, some markers are sensitive enough to detect a change before any clinical change is detected by the prevalent gold-standard survey instrument, the ALSFRS-R scale. The findings disclosed herein highlight the importance of including multimodal speech markers from remotely-collected data in clinical trials. Their inclusion can facilitate accessible, speedier and cost-effective randomized controlled trials.

Figure 23:
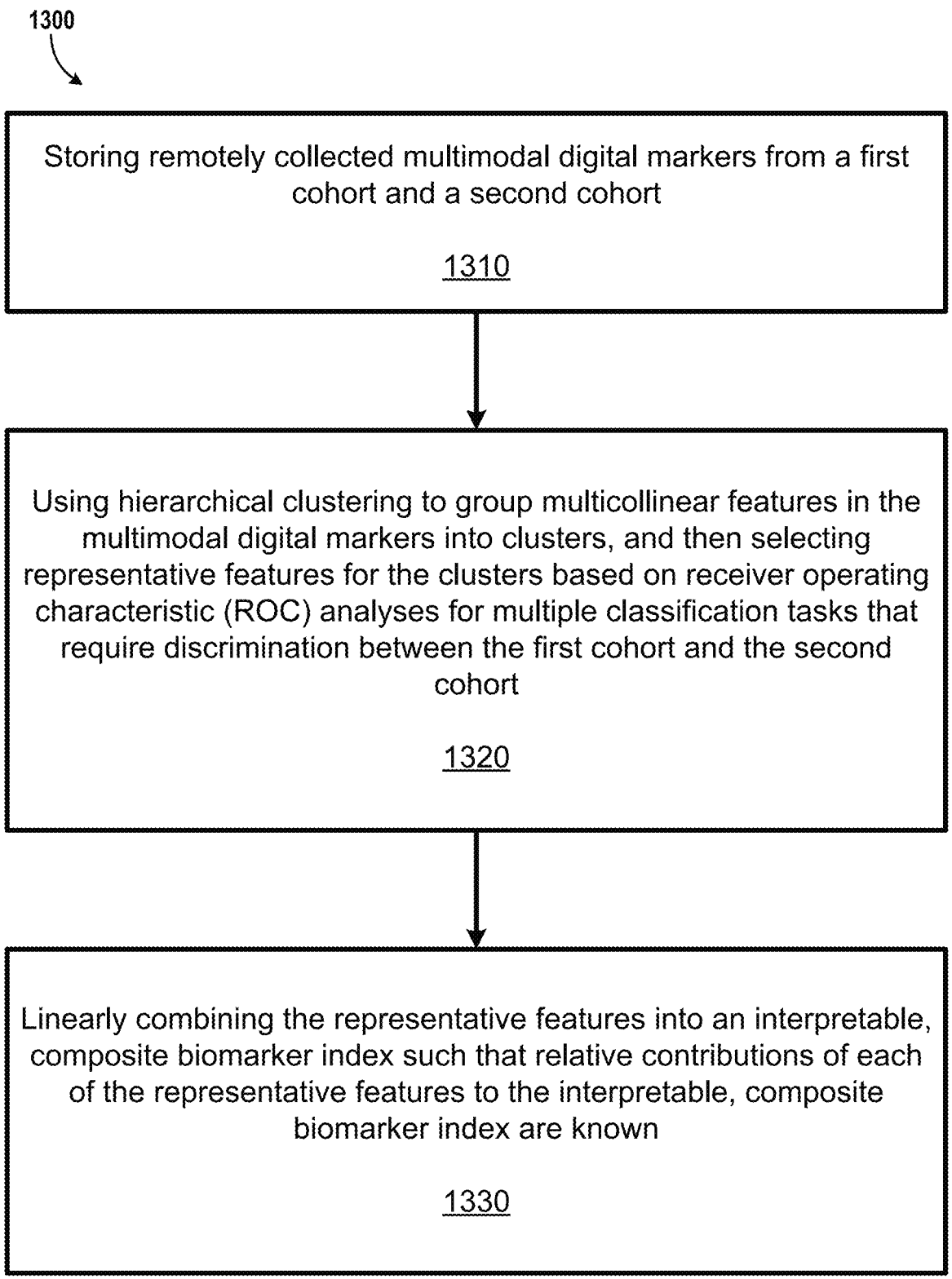
FIG. 23 is a flowchart showing one example operation of generating interpretable, composite marker indexes.

FIG. 23 is a flowchart showing an example operation of generating interpretable, composition marker indexes that are discriminative and noise-robust. Operation 1300 begins at block 1310 where remotely collected multimodal digital markers from a first cohort and a second cohort are stored. Multimodal digital markers from the first cohort and second cohort can be obtained and stored by, for example, utilizing virtual agent 106 described above with respect to FIGS.

11A, 11B, 11C. For instance, in one example, the remotely collected multimodal digital markers can be stored in the same manner as remotely collected multimodal digital markers 108 described above with respect to FIGS. 11A, 11B, 11C. Specifically, a cloud-based multimodal dialog system can be utilized as a virtual agent to collect media recordings from participants who engage in a structured conversation with the virtual agent. Each participant within the first cohort and second cohort is provided with a unique website link to the multimodal dialog system platform, which a participant can access to start the assessment. The assessment can be accessed by any suitable computing device, such as a mobile phone, laptop, or other computing device.

After completing microphone and camera checks to ensure data collection of good quality, participants engage in a conversation with the virtual agent. The dialog protocol elicits different types of speech samples. For example, one or more of the following tasks can be included in a dialog protocol: read speech (sentence intelligibility test (SIT), 5-15 words; Bamboo reading passage (RP), 99 words), measure of diadochokinesis (DDK, rapidly repeating the syllables "pA-tA-kA"), single breath counting (SBC), and/or free speech in form of a picture description task (PD). During the assessment, the virtual agent can ask participants to do the aforementioned tasks. Due to the conversational nature, participants receive feedback (e.g., when they spoke shorter than a predefined threshold for a given task), and the virtual agent can provide demonstrations of how a given task should be performed. Participants' audio and video streams are subsequently uploaded and segmented in real-time, and stored in a memory as remotely collected multimodal digital markers. After dialog completion, participants are subsequently prompted to fill out the ALSFRS-R scale, the clinical gold standard to capture progression in ALS.

Operation 1300 proceeds at block 1320 where hierarchical clustering is utilized to group multicollinear features in the multimodal digital markers into clusters, and then select representative features for the clusters based on receiver operating characteristic (ROC) analyses for multiple classification tasks that require discrimination between the first cohort and the second cohort. To handle multicollinear features and identify a good set of representative features, hierarchical clustering is applied. A distance threshold can be determined manually to select clusters that represent sensible feature groupings in terms of the domain (e.g. frequency or timing related speech features) or the area of the face (e.g. features pertaining to jaw movement). Alternatively, selecting the threshold for splitting clusters can also be done in a data-driven way as well.

The final feature set determined at block 1320 is versatile with respect to different aspects, like progress monitoring in pALS and early diagnosis (classifying between controls and the PRE group). In some examples, ROC analyses on the individual features can be conducted for the following binary classification tasks: healthy controls (CON) vs. those with ALS (pALS), CON vs. sign symptomatic (BUL), CON vs. pre-symptomatic (PRE), PRE vs. BUL, and bulbar onset vs non-bulbar onset. In addition, to assess associations between features and the ALSFRS-R bulbar subscore, the total information coefficient (TICe) and the maximum information coefficient (MICe) can be estimated (e.g., by utilizing the MICtools software package).

For every cluster, the metric that yields the best result in the majority of tests (highest area under curve (AUC) of the ROC curve and highest MICe) is selected as representative. For this, metrics are considered independent of the task first. For example, when the average jaw center speed metric extracted from the SIT and DDK tasks both performed similarly, DDK may be preferred because it was already in the set of tasks selected for other feature groups. In this manner, the tasks are reduced to DDK, picture description and the reading passage.

Operation 1300 proceeds at block 1330 where representative features are linearly combined into an interpretable, composite marker index such that the relative contributions of each of the representative features to the interpretable, composite marker index are known. Three methods of index computation to optimize linear discriminability between cohorts can be utilized: Youden Index optimization, Fisher's Linear Discriminant Function, and Logistic Regression. Each of these methods will be described in turn.

Youden Index Optimization is defined as J=sensitivity+ specificity−1. The objective is to find the cut-off point for a diagnostic test or marker that maximizes J. The advantage of this stepwise approach is that it is non-parametric and distribution-free.

Fisher's Linear Discriminant Function provides a closed form solution to find the best linear combination that maximizes the AUC, which is based on Fisher's linear discriminant analysis (LDA). Under assumption of Gaussian distributions, the coefficients are proportional to $$\left(\frac{Sx}{m-1} + \frac{Sy}{n-1}\right)^{-1} (Y^- - X^-) \quad (1)$$

where Sx and Sy are sample covariance matrices of the two cohorts, m and n the respective number of samples in each group, and $X^-$ and $Y^-$ the sample means.

Logistic Regression can also be utilized to calculate the model coefficients that serve as feature weights. In particular, a liblinear solver and L1 regularization is utilized, a grid search cross validation (within each train partition) was used over the parameter C to optimize for AUC. L1 regularization is chosen because it enforces a sparse weight vector, which is beneficial because a minimal number of features is desired to improve clinical utility.

FIG. 24 is a table showing extracted metrics, feature clusters, and selected representative metrics. For visual metrics, functionals (minimum, maximum, average) are applied to produce one value across all video frames of an utterance. Visual distance metrics are measured in pixels and are normalized by dividing them by the intercanthal distance (distance between inner corners of the eyes) for each subject. As shown in FIG. 24, "TRR" corresponds to test-retest reliability. "LL" corresponds to lower lip. "JC" corresponds to jaw center. "RP" corresponds to reading passage. "PD" corresponds to picture description. "DDK" corresponds to diadochokinesis. Additionally, as shown, the right-hand side of FIG. 24 shows the final feature set along with each feature's test-retest reliability.

FIG. 25 is a table showing mean results from 5-fold cross validation. In particular, FIG. 25 shows mean results from 5-fold cross validation for the binary classification task bulbar onset vs. non-bulbar onset. As used in FIG. 25, "UAR" corresponds to unweighted average recall. "Sen." corresponds to sensitivity. "Spec." corresponds to specificity.

FIG. 25 shows the mean results for the index scores and individual features across 5 folds, including the Youden index and AUC on the train set, and sensitivity, specificity, and UAR on the test set. To obtain results on the test set, the optimal cut-off point was computed that maximizes the Youden index on the train set (using the R package pROC) and applied as a threshold to classify the test samples.

Speaking duration (sp. dur) of the reading passage is the best single feature, which establishes a strong baseline. The Youden J-based method yields a slightly higher test result than speaking duration and all three index scores yield better results than the baseline index (in terms of train AUC and test UAR).

In general, high variance is observed between the individual cross validation folds. For individual features the standard deviation of UAR across folds ranges between 0.036 and 0.096, depending on the feature (0.046 for speaking duration (RP)). For the index scores, the standard deviation was 0.035, 0.037, and 0.048 for logistic regression, LDA, and Youden J respectively. This suggests that overall the variance is reduced when applying an index as compared to individual features, which supports the use of such an optimal composite index as a relatively more noise-robust composite marker.

Figure 26:
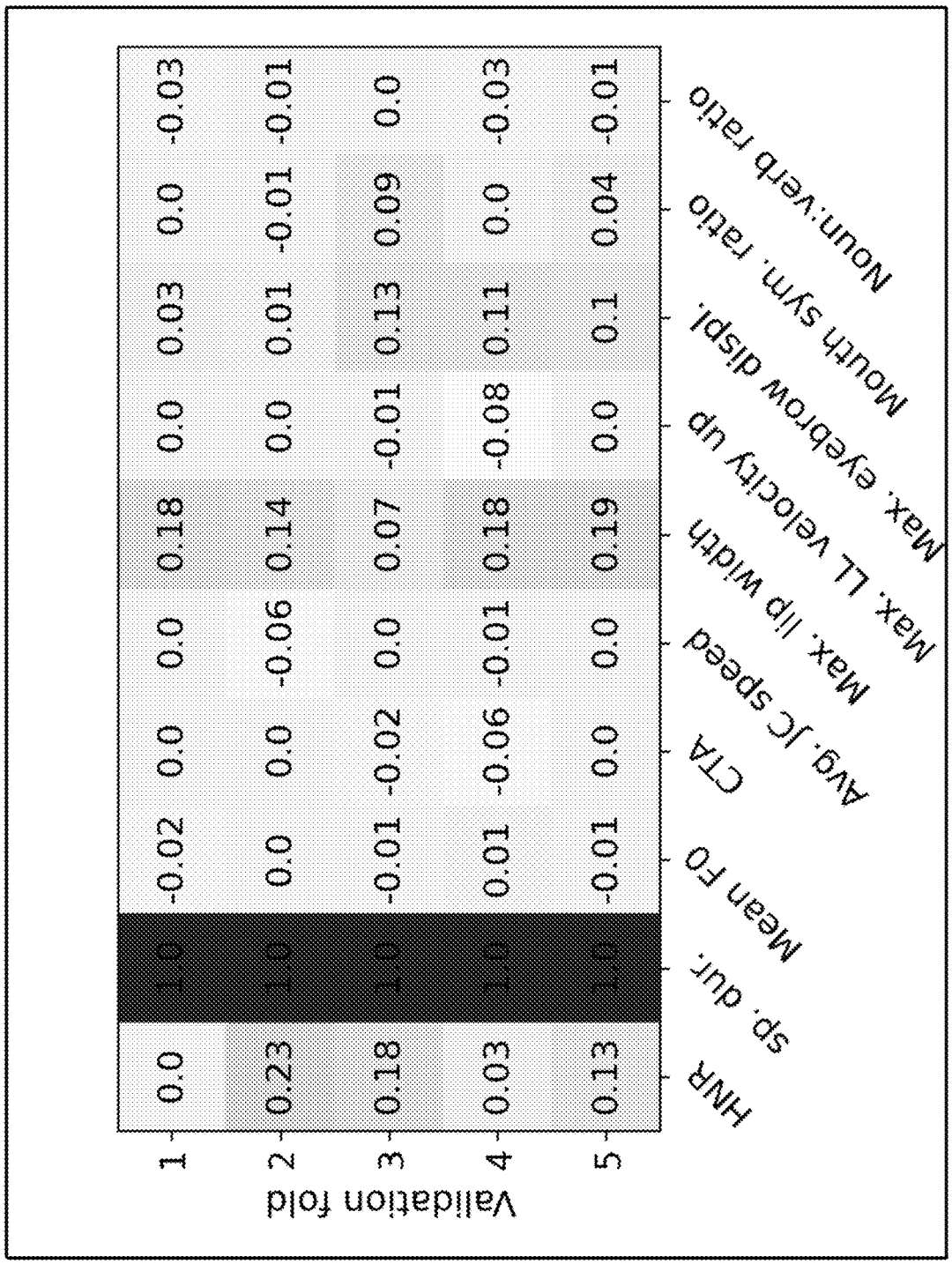
FIG. 26 is a chart showing feature weights across five validation folds.
Figure 27:
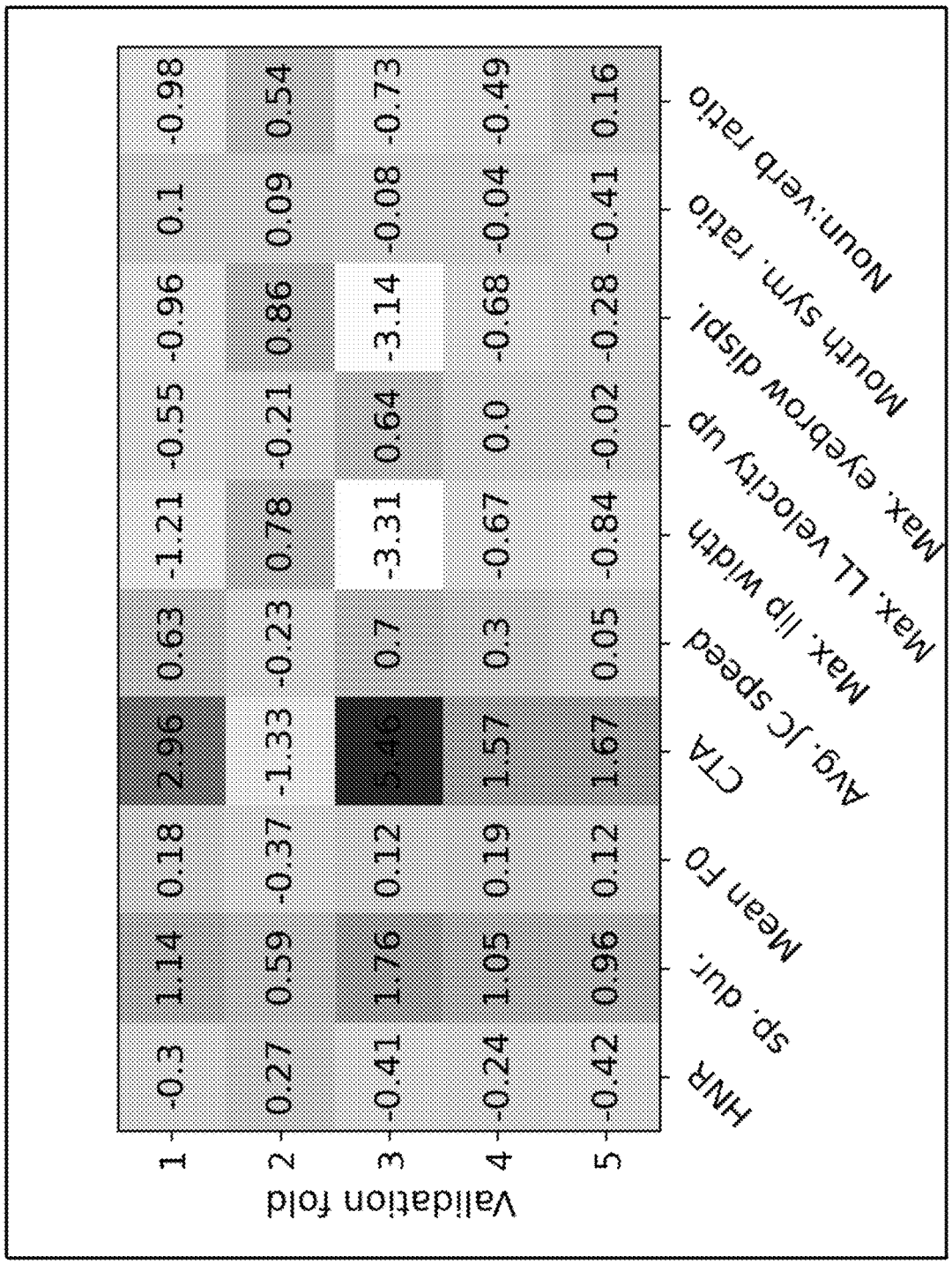
FIG. 27 is a chart showing feature weights across five validation folds.

FIGS. 26-27 are charts showing feature weights across five validation folds. FIG. 26 is a chart showing feature wights across five validation folds for the Youden J based index. FIG. 27 is a chart showing feature weights across five validation folds for the LDA based index. As shown, speaking duration is selected as the most relevant feature in the Youden J based index and the weights are relatively stable across test folds compared to the LDA based method. In contrast, the LDA based method assigns the largest weights to CTA, and the weights are more unstable across folds. For logistic regression, L1 regularization was utilized (enforcing coefficient sparsity), setting most feature weights (close) to zero. Features that had non-zero weights across most test folds were CTA, max. lip width, and max. eyebrow displacement.

As shown in FIGS. 24-27, the three investigated methods for index computation-logistic regression, LDA based, and Youden index optimization-all yield indexes that perform better than the baseline of equally weighted features and most of the individual features, while returning lower performance variability overall (and therefore better noise-robustness) across test partitions. Overall, the Youden index based composite score yielded the best result (approximately on par with speaking duration as individual feature). The methods for linear combinations of features are clinically interpretable because the relative contributions of in-di-vidual features to the overall index are known. Furthermore, the metrics themselves are chosen to be meaningful and interpretable, as opposed to learnt representations. Additionally, the results set forth in FIGS. 24-27 show that the Youden index based and the logistic regression coefficients are more stable across different train/test splits of the data than the LDA based weights, in terms of the relative contribution of each feature.

Multiple speech biomarkers have been shown to carry useful information regarding diseases like Amyotrophic Lateral Sclerosis (ALS) pathology and Schizophrenia. We propose a two-step framework to compute optimal linear combinations (indexes) of these biomarkers that are more discriminative and noise-robust than the individual markers, which is important for clinical care and pharmaceutical trial applications. First, we use a hierarchical clustering-based method to select representative speech metrics from a dataset comprising 143 people with ALS and 135 age- and sex-matched healthy controls. Second, we analyze three methods of index computation that optimize linear discrim-inability, Youden Index, and sparsity of logistic regression model weights, respectively, and evaluate their performance with 5-fold cross validation. We find that the proposed indexes are generally more discriminative of bulbar vs non-bulbar onset in ALS than their individual component metrics as well as an equally weighted baseline.

Schizophrenia Embodiment

Speech and oro-facial biomarkers have shown great promise for remote assessment and monitoring of neurological and mental health conditions. Automated and scalable remote monitoring solutions are capable of collecting a variety of different measurements from speech and video recordings. A critical question for clinical practice and pharmaceutical trial applications is how to combine these biomarkers into a single index to strengthen statistical power and enhance the interpretation of the outcomes. In this contribution, we propose a method to compute an interpretable index score based on multiple acoustic, linguistic, and visual features and present our findings on its efficacy for the assessment of Schizophrenia.

We collected video recordings from 48 people diagnosed with Schizophrenia and 63 healthy controls using a multi-modal remote patient monitoring platform. A virtual dialog agent guides participants through a structured speech assessment designed to elicit different types of speech samples and facial movements. Speech and oro-facial features are extracted in real-time, and linguistic features are computed based on automatically obtained transcriptions. We present a two-step process to obtain a weighted linear combination as a single index: (a) features are selected based on a redundancy analysis and receiver-operator characteristics (ROC) analysis, and (b) index scores are computed based on linear discriminant analysis (LDA) and logistic regression. We evaluate the efficacy of these indexes in distinguishing people with Schizophrenia from controls with 5-fold cross validation. Additionally, we report correlations between the proposed index scores and the Positive and Negative Syndrome Scale (PANSS), and the Brief Negative Symptom Scale (BNSS).

Both LDA and logistic regression yield index scores that perform significantly better in discriminating people with Schizophrenia from healthy controls compared to each individual component feature. The best result was obtained with the logistic regression-based index (85.80% unweighted average recall (UAR)). The best individual feature was canonical timing alignment, a measure of phonetic alignment between the participant's utterance and a canonical pronunciation (73.95% UAR). The index weights indicate that a variety of speech and facial features contribute useful information, including cepstral peak prominence (measure of voice quality), average eye opening, acoustic shimmer (amplitude variation), and velocity of the lower lip.

Preliminary correlation analyses showed that the Pearson correlation between the logistic regression-based index and the PANSS total score was 0.19 (p=0.072). It was 0.00 (p=0.981) for the PANSS positive score, 0.29 (p=0.005) for the PANSS negative score and 0.34 (p=0.001) for the BNSS total score, which indicates that the index is more sensitive to capturing negative symptoms.

A weighted linear combination of speech and oro-facial biomarkers extracted automatically using a multimodal remote patient monitoring platform can serve as a single index score for the assessment of Schizophrenia. We showed that such an index improves the discriminability compared to the individual component features. Future work will focus on optimizing the index score towards severity grading of negative symptoms, crucial for progress monitoring.

Computer System

Figure 28:
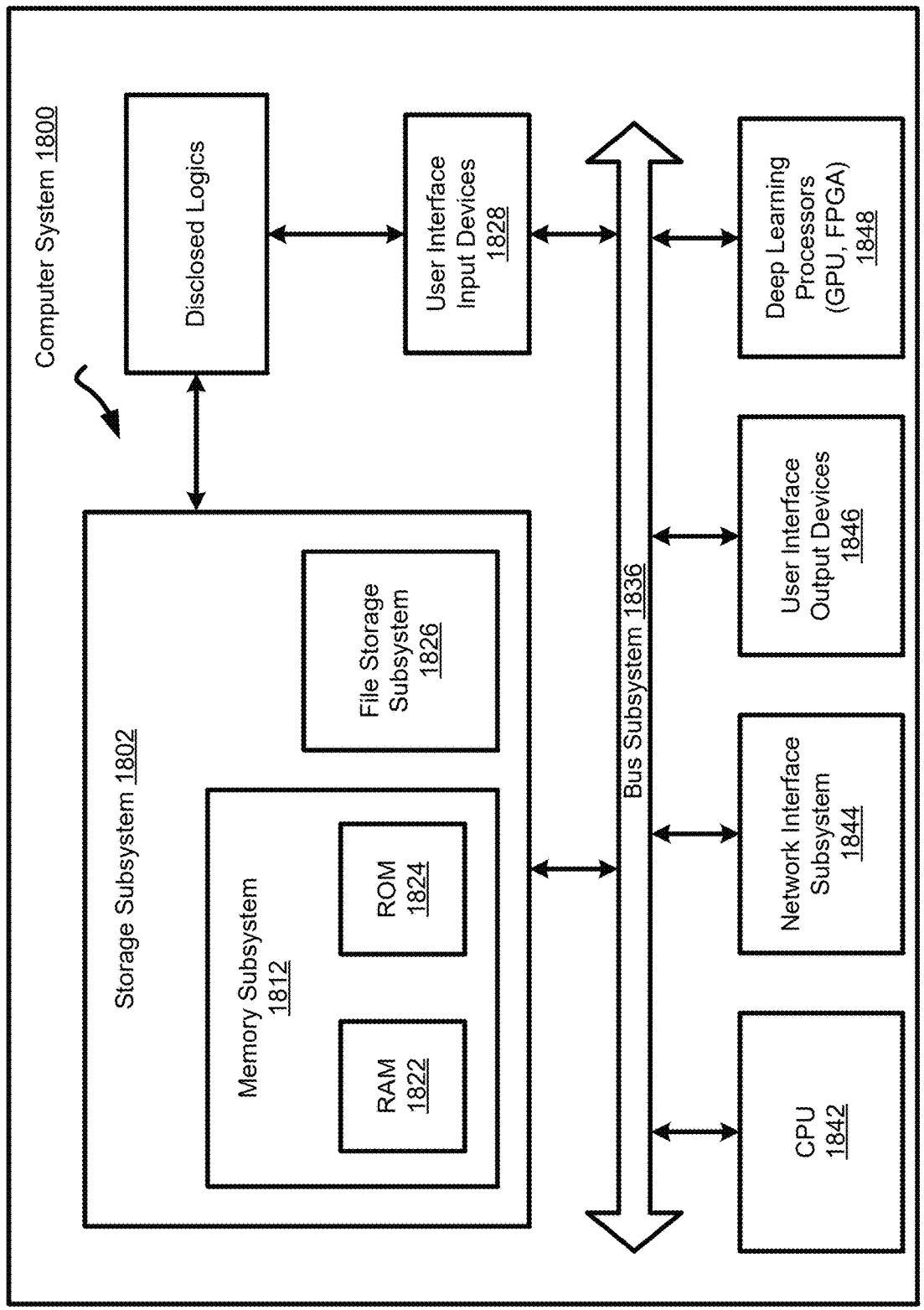
FIG. 28 is a block diagram of a computer system that can be used to implement the technology disclosed.

FIG. 28 shows an example computer system 1800 that can be used to implement the technology disclosed. Computer system 1800 includes at least one central processing unit (CPU) 1842 that communicates with a number of peripheral devices via bus subsystem 1826. These peripheral devices can include a storage subsystem 1802 including, for example, memory devices and a file storage subsystem 1826, user interface input devices 1828, user interface output devices 1846, and a network interface subsystem 1844. The input and output devices allow user interaction with computer system 1800. Network interface subsystem 1844 provides an interface to outside networks, including an interface to corresponding interface devices in other computer systems.

In one implementation, the various logics disclosed here is communicably linked to the storage subsystem 1802 and the user interface input devices 1828.

User interface input devices 1828 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1800.

User interface output devices 1846 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1800 to the user or to another machine or computer system.

Storage subsystem 1802 stores programming and data constructs that provide the functionality of some or all of the modules and methods described herein. These software modules are generally executed by processors 1848.

Processors 1848 can be graphics processing units (GPUs), field-programmable gate arrays (FPGAs), application-specific integrated circuits (ASICs), and/or coarse-grained reconfigurable architectures (CGRAs). Processors 1848 can be hosted by a deep learning cloud platform such as Google Cloud Platform™, Xilinx™, and Cirrascale™. Examples of processors 1848 include Google's Tensor Processing Unit (TPU)™, rackmount solutions like GX4 Rackmount Series™, GX18 Rackmount Series™, NVIDIA DGX-1™, Microsoft' Stratix V FPGA™, Graphcore's Intelligent Processor Unit (IPU)™, Qualcomm's Zeroth Platform™ with Snapdragon processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 1812 used in the storage subsystem 1802 can include a number of memories including a main random access memory (RAM) 1822 for storage of instructions and data during program execution and a read only memory (ROM) 1824 in which fixed instructions are stored. A file storage subsystem 1826 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1826 in the storage subsystem 1802, or in other machines accessible by the processor.

Bus subsystem 1836 provides a mechanism for letting the various components and subsystems of computer system 1800 communicate with each other as intended. Although bus subsystem 1836 is shown schematically as a single bus, alternative implementations of the bus subsystem can use multiple busses.

Computer system 1800 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1800 depicted in FIG. 28 is intended only as a specific example for purposes of illustrating the preferred implementations of the present invention. Many other configurations of computer system 1800 are possible having more or less components than the computer system depicted in FIG. 28.

In various implementations, a learning system is provided. In some implementations, a feature vector is provided to a learning system. Based on the input features, the learning system generates one or more outputs. In some implementations, the output of the learning system is a feature vector. In some implementations, the learning system comprises an SVM. In other implementations, the learning system comprises an artificial neural network. In some implementations, the learning system is pre-trained using training data. In some implementations training data is retrospective data. In some implementations, the retrospective data is stored in a data store. In some implementations, the learning system may be additionally trained through manual curation of previously generated outputs.

In some implementations, the sequence generator 172 is a trained classifier. In some implementations, the trained classifier is a random decision forest. However, it will be appreciated that a variety of other classifiers are suitable for use according to the present disclosure, including linear classifiers, support vector machines (SVM), or neural networks such as recurrent neural networks (RNN).

Suitable artificial neural networks include but are not limited to a feedforward neural network, a radial basis function network, a self-organizing map, learning vector quantization, a recurrent neural network, a Hopfield network, a Boltzmann machine, an echo state network, long short term memory, a bi-directional recurrent neural network, a hierarchical recurrent neural network, a stochastic neural network, a modular neural network, an associative neural network, a deep neural network, a deep belief network, a convolutional neural networks, a convolutional deep belief network, a large memory storage and retrieval neural network, a deep Boltzmann machine, a deep stacking network, a tensor deep stacking network, a spike and slab restricted Boltzmann machine, a compound hierarchical-deep model, a deep coding network, a multilayer kernel machine, or a deep Q-network.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

FIG. 28 is a schematic of an exemplary computing node. Computing node 1800 is only one example of a suitable computing node and is not intended to suggest any limitation as to the scope of use or functionality of embodiments described herein. Regardless, computing node 1800 is capable of being implemented and/or performing any of the functionality set forth hereinabove.

In computing node 1800 there is a computer system/server, which is operational with numerous other general purpose or special purpose computing system environments or configurations. Examples of well-known computing systems, environments, and/or configurations that may be suitable for use with computer system/server include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed computing environments that include any of the above systems or devices, and the like.

Computer system/server may be described in the general context of computer system-executable instructions, such as program modules, being executed by a computer system. Generally, program modules may include routines, programs, objects, components, logic, data structures, and so on that perform particular tasks or implement particular abstract data types. Computer system/server may be practiced in distributed computing environments where tasks are performed by remote processing devices that are linked through a communications network. In a distributed computing environment, program modules may be located in both local and remote computer system storage media including memory storage devices.

As shown in FIG. 28, computer system/server in computing node 1800 is shown in the form of a general-purpose computing device. The components of computer system/server may include, but are not limited to, one or more processors or processing units, a system memory, and a bus that couples various system components including system memory to processor.

The Bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server typically includes a variety of computer system readable media. Such media may be any available media that is accessible by computer system/server, and it includes both volatile and non-volatile media, removable and non-removable media.

System memory can include computer system readable media in the form of volatile memory, such as random access memory (RAM) and/or cache memory. Algorithm Computer system/server may further include other removable/non-removable, volatile/non-volatile computer system storage media. By way of example only, storage system can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus by one or more data media interfaces. As will be further depicted and described below, memory may include at least one program product having a set (e.g., at least one) of program modules that are configured to carry out the functions of embodiments of the disclosure.

Program/utility, having a set (at least one) of program modules, may be stored in memory by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments as described herein.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some implementations, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to implementations of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures above illustrate the architecture, functionality, and operation of possible implementations of systems, methods, and computer program products according to various implementations of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures above. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

CLAUSES

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

We disclose the following clauses:

Clause Set 1

1. A system for identifying efficacious biomarkers to improve predictive modelling of neurodegenerative disease progression, comprising:
    memory storing remotely collected multimodal digital biomarkers from a first cohort experiencing a bulbar onset in the neurodegenerative disease progression and a second cohort experiencing a non-bulbar onset in the neurodegenerative disease progression;
    feature selection logic configured to identify a subset of the multimodal digital biomarkers that are best at capturing differences between the bulbar onset and the non-bulbar onset;
    responsiveness determination logic configured to determine a responsiveness parameter that specifies how a rate of change in the identified subset of the multimodal digital biomarkers differs between the bulbar onset and the non-bulbar onset;
    time to detect change determination logic configured to determine a time to detect change parameter that specifies a time period required to detect a clinically meaningful change in the identified subset of the multimodal digital biomarkers from disease onset in the first cohort and the second cohort;
    sample size effect determination logic configured to determine how the responsiveness parameter and the time to detect change parameter change depending on a sample size of the first cohort and the second cohort; and
    sensitivity determination logic configured to determine a sensitivity parameter that specifies whether the identified subset of the multimodal digital biomarkers detect disease deterioration during intervals of time when no changes are reported in an external clinical gold standard.
2. The system of clause 1, wherein the remotely collected multimodal digital biomarkers span across an audio domain, a text domain, and/or a video domain.
3. The system of clause 2, wherein the audio domain includes one or more energy metrics, one or more timing metrics, one or more voice quality metrics, and/or one or more frequency metrics.
4. The system of clause 3, wherein the energy metrics include shimmer (%), intensity (dB), and/or signal-to-noise ratio (dB).
5. The system of clause 3, wherein the timing metrics include timing speaking and articulation duration (sec.), articulation, and speaking rate (WPM), percent pause time (PPT, %), canonical timing agreement (CTA, %), cycle-to-cycle temporal variability (cTV, sec.), syllable rate (syl./sec.), and/or number of syllables.
6. The system of clause 3, wherein the voice quality metrics include voice quality cepstral peak prominence (CPP, dB), and/or harmonics-to-noise ratio (HNR, dB).
7. The system of clause 3, wherein the frequency metrics include frequency mean, max., min. fundamental frequency F0 (Hz), first three formants F1, F2, F3 (Hz), slope of 2nd formant (Hz/sec.), and/or jitter (%).
8. The system of clause 2, wherein the text domain includes one or more lexico-semantic metrics.
9. The system of clause 8, wherein the lexico-semantic metrics include word count, percentage of content words, noun rate, verb rate, pronoun rate, noun-to-verb ratio, noun-to-pronoun ratio, closed class word ratio, and/or idea density.
10. The system of clause 2, wherein the video domain includes one or more mouth (distances) metrics, one or more lip/jaw movement metrics, and/or one or more eyes metrics.
11. The system of clause 10, wherein the mouth (distances) metrics include lip aperture/opening, lip width, mouth surface area, and/or mean symmetry ratio between left and right half of the mouth.
12. The system of clause 10, wherein the lip/jaw movement metrics include velocity, acceleration, jerk, and/or speed of lower lip and jaw center.
13. The system of clause 10, wherein the eyes metrics include number of eye blinks per sec., eye opening, and/or vertical displacement of eyebrows.
14. The system of clause 1, wherein the remotely collected multimodal digital biomarkers include features that are metrics extracted for a specific stimulus or task.
15. The system of clause 14, wherein the feature selection logic is further configured to group the features into clusters, and to identify one or more representative features for each of the clusters.
16. The system of clause 15, wherein the clusters include timing: duration and rates, temporal diadochokinesis (DDK) measures, timing alignment, duration and word count for picture description (PD), eyebrow displacement, pause time, lip width, voice quality (read/free speech), cepstral peak prominence (CPP), voice quality for single breath counting (SBC) and DDK, lip aperture, mouth surface area, eye opening measures, content and closed class words, min. and mean F0, jaw center (JC) velocity for sentence intelligibility test (SIT), duration measures for SBC and DDK, JC velocity for reading passage (RP), verb/noun/pronoun rates, lower lip (LL) velocity, JC velocity, JC velocity, max. F0 and F0 stdev., LL velocity for read speech, JC velocity for DDK, LL velocity for DDK, LL velocity for SBC, and/or mouth symmetry ratio.
17. The system of clause 16, wherein the representative features include speaking duration (RP), cycle-to-cycle temporal variability (cTV) (DDK), canonical timing agreement (CTA) (RP), word count (PD), max. eyebrow displacement (SIT), percent pause time (PPT) (SIT), max. lip width (RP), harmonics-to-noise ratio (HNR) (SIT), CPP (RP), HNR (DDK), mean lip aperture (SIT), max. eye opening (SIT), closed class word ratio (PD), mean F0 (RP), max. JC velocity down (SIT), number of syllables (DDK), max. JC velocity up (RP), pronoun rate (PD), max. LL jerk up (PD), max. JC velocity down (PD), mean JC speed (SBC), max. F0 (SIT), mean LL speed (SIT), max. JC velocity down (DDK), mean LL jerk (DDK), max. LL speed (SBC), and/or mean mouth symmetry ratio (RP).
18. The system of clause 1, wherein the remotely collected multimodal digital biomarkers are extracted using a structured conversational dialog with a virtual agent.
19. The system of clause 1, wherein the external clinical gold standard is Revised Amyotrophic Lateral Sclerosis Functional Rating Scale (ALSFRS-R).
20. The system of clause 1, wherein the sensitivity determination logic is further configured to determine which of the identified subset of the multimodal digital biomarkers are clinically meaningful using a minimal clinically important difference (MCID) parameter.
21. The system of clause 20, wherein the MCID parameter is a smallest domain-specific change that is considered to be clinically relevant, and is quantified as a threshold for a change corresponding to clinical improvement or deterioration as measured by the external clinical gold standard.
22. The system of clause 1, wherein the responsiveness determination logic is further configured to determine the responsiveness parameter using growth curve models (GCMs).
23. The system of clause 22, wherein the responsiveness determination logic is further configured to determine the responsiveness parameter based on a statistical utility that specifies whether time taken in weeks to detect the disease deterioration greater than a standard error of a mean for a corresponding cohort.
24. The system of clause 23, wherein the responsiveness determination logic is further configured to determine the responsiveness parameter based on a clinical utility that specifies whether time taken in weeks to detect the disease deterioration greater than a MCID value.
25. The system of clause 1, wherein the sensitivity determination logic is further configured to determine the sensitivity parameter using the GCMs.
26. The system of clause 1, wherein the identified subset of the multimodal digital biomarkers includes speaking duration (RP), cycle-to-cycle temporal variability (cTV) (DDK), canonical timing agreement (CTA) (RP), word count (PD), max. eyebrow displacement (SIT), percent pause time (PPT) (SIT), max. lip width (RP), harmonics-to-noise ratio (HNR) (SIT), CPP (RP), HNR (DDK), mean lip aperture (SIT), max. eye opening (SIT), closed class word ratio (PD), mean F0 (RP), max. JC velocity down (SIT), number of syllables (DDK), and/or max. JC velocity up (RP).
27. The system of clause 16, based on the responsiveness parameter, further configured to identify from the identified subset of the multimodal digital biomarkers, a further subset of multimodal digital biomarkers that show a significantly different change over time in the first cohort with the bulbar onset as compared to the second cohort with the non-bulbar onset.
28. The system of clause 27, wherein the further subset of multimodal digital biomarkers includes RP CTA (%), PD word count (words), RP speaking duration (seconds), RP mean F0 (Hz), DDK HNR (dB), RP CPP (dB), RP max. lip width, SIT PPT (%), and/or SIT HNR (dB).
29. The system of clause 28, based on the time to detect change parameter, further configured to identify that the RP CTA and the PD word count are most responsive digital biomarkers that showed the shortest time to detect a change that was statistically and clinically relevant.
30. The system of clause 29, further configured to determine that the responsiveness of the identified subset of the multimodal digital biomarkers remains relatively stable even with small sample sizes.
31. The system of clause 30, based on the sensitivity parameter, further configured to identify that the RP CTA, the PD word count, the RP speaking duration, and the RP CPP showed a statistically significant change over time even when the external clinical gold standard indicated no clinical change in the first cohort with the bulbar onset.
32. A system for identifying efficacious biomarkers to improve predictive modelling of disease progression, comprising:
memory storing remotely collected multimodal digital biomarkers from a first cohort and a second cohort;
feature selection logic configured to identify a subset of the multimodal digital biomarkers that are best at discriminating between the first cohort and the second cohort;
responsiveness determination logic configured to determine a responsiveness parameter that specifies how a rate of change in the identified subset of the multimodal digital biomarkers differs between the first cohort and the second cohort;
time to detect change determination logic configured to determine a time to detect change parameter that specifies a time period required to detect a clinically meaningful change in the identified subset of the multimodal digital biomarkers from disease onset in the first cohort and the second cohort;
sample size effect determination logic configured to determine how the responsiveness parameter and the time to detect change parameter change depending on a sample size of the first cohort and the second cohort; and
sensitivity determination logic configured to determine a sensitivity parameter that specifies whether the identified subset of the multimodal digital biomarkers detect disease deterioration during intervals of time when no changes are reported in an external clinical gold standard.

Clause Set 2

1. A computer-implemented method of generating interpretable, composite biomarker indexes that are discriminative and noise-robust, including:
storing remotely collected multimodal digital biomarkers from a first cohort and a second cohort;
using hierarchical clustering to group multicollinear features in the multimodal digital biomarkers into clusters, and then selecting representative features for the clusters based on receiver operating characteristic (ROC) analyses for multiple classification tasks that require discrimination between the first cohort and the second cohort; and
linearly combining the representative features into an interpretable, composite biomarker index such that relative contributions of each of the representative features to the interpretable, composite biomarker index are known.
2. The method of clause 1, furthering including linearly combining the representative features using Youden Index Optimization.
3. The method of clause 1, furthering including linearly combining the representative features using Fisher's Linear Discriminant Function.
4. The method of clause 1, furthering including linearly combining the representative features using Logistic Regression.
5. The method of clause 1, wherein the first cohort is healthy controls (CON), and the second cohort is all people with ALS (pALS).
6. The method of clause 1, wherein the first cohort is healthy controls (CON), and the second cohort is bulbar symptomatic (BUL).
7. The method of clause 1, wherein the first cohort is healthy controls (CON), and the second cohort is bulbar pre-symptomatic (PRE).
8. The method of clause 1, wherein the first cohort is bulbar pre-symptomatic (PRE), and the second cohort is bulbar symptomatic (BUL).
9. The method of clause 1, wherein the first cohort is bulbar onset, and the second cohort is non-bulbar onset.

Clause Set 3
1. A system for identifying efficacious markers to improve predictive modelling of condition progression, comprising:
   memory storing remotely collected multimodal digital markers from a first cohort experiencing a sign onset in the condition progression and a second cohort experiencing a non-sign onset in the condition progression;
   feature selection logic configured to identify a subset of the multimodal digital markers that are best at capturing differences between the sign onset and the non-sign onset;
   responsiveness determination logic configured to determine a responsiveness parameter that specifies how a rate of change in the identified subset of the multimodal digital markers differs between the sign onset and the non-sign onset;
   time to detect change determination logic configured to determine a time to detect change parameter that specifies a time period required to detect a meaningful change in the identified subset of the multimodal digital markers from condition onset in the first cohort and the second cohort;
   sample size effect determination logic configured to determine how the responsiveness parameter and the time to detect change parameter change depending on a sample size of the first cohort and the second cohort; and
   sensitivity determination logic configured to determine a sensitivity parameter that specifies whether the identified subset of the multimodal digital markers detect condition deterioration during intervals of time when no changes are reported in an external gold standard.
2. The system of clause 1, wherein the remotely collected multimodal digital markers span across an audio domain, a text domain, and/or a video domain.
3. The system of clause 2, wherein the audio domain includes one or more energy metrics, one or more timing metrics, one or more voice quality metrics, and/or one or more frequency metrics.
4. The system of clause 3, wherein the energy metrics include shimmer (%), intensity (dB), and/or signal-to-noise ratio (dB).
5. The system of clause 3, wherein the timing metrics include timing speaking and articulation duration (sec.), articulation, and speaking rate (WPM), percent pause time (PPT, %), canonical timing agreement (CTA, %), cycle-to-cycle temporal variability (cTV, sec.), syllable rate (syl./sec.), and/or number of syllables.
6. The system of clause 3, wherein the voice quality metrics include voice quality cepstral peak prominence (CPP, dB), and/or harmonics-to-noise ratio (HNR, dB).
7. The system of clause 3, wherein the frequency metrics include frequency mean, max., min. fundamental frequency F0 (Hz), first three formants F1, F2, F3 (Hz), slope of 2nd formant (Hz/sec.), and/or jitter (%).
8. The system of clause 2, wherein the text domain includes one or more lexico-semantic metrics.
9. The system of clause 8, wherein the lexico-semantic metrics include word count, percentage of content words, noun rate, verb rate, pronoun rate, noun-to-verb ratio, noun-to-pronoun ratio, closed class word ratio, and/or idea density.
10. The system of clause 2, wherein the video domain includes one or more mouth (distances) metrics, one or more lip/jaw movement metrics, and/or one or more eyes metrics.
11. The system of clause 10, wherein the mouth (distances) metrics include lip aperture/opening, lip width, mouth surface area, and/or mean symmetry ratio between left and right half of the mouth.
12. The system of clause 10, wherein the lip/jaw movement metrics include velocity, acceleration, jerk, and/or speed of lower lip and jaw center.
13. The system of clause 10, wherein the eyes metrics include number of eye blinks per sec., eye opening, and/or vertical displacement of eyebrows.
14. The system of clause 1, wherein the remotely collected multimodal digital markers include features that are metrics extracted for a specific stimulus or task.
15. The system of clause 14, wherein the feature selection logic is further configured to group the features into clusters, and to identify one or more representative features for each of the clusters.
16. The system of clause 15, wherein the clusters include timing: duration and rates, temporal diadochokinesis (DDK) measures, timing alignment, duration and word count for picture description (PD), eyebrow displacement, pause time, lip width, voice quality (read/free speech), cepstral peak prominence (CPP), voice quality for single breath counting (SBC) and DDK, lip aperture, mouth surface area, eye opening measures, content and closed class words, min. and mean F0, jaw center (JC) velocity for sentence intelligibility test (SIT), duration measures for SBC and DDK, JC velocity for reading passage (RP), verb/noun/pronoun rates, lower lip (LL) velocity, JC velocity, JC velocity, max. F0 and F0 stdev., LL velocity for read speech, JC velocity for DDK, LL velocity for DDK, LL velocity for SBC, and/or mouth symmetry ratio.
17. The system of clause 16, wherein the representative features include speaking duration (RP), cycle-to-cycle temporal variability (cTV) (DDK), canonical timing agreement (CTA) (RP), word count (PD), max. eyebrow displacement (SIT), percent pause time (PPT) (SIT), max. lip width (RP), harmonics-to-noise ratio (HNR) (SIT), CPP (RP), HNR (DDK), mean lip aperture (SIT), max. eye opening (SIT), closed class word ratio (PD), mean F0 (RP), max. JC velocity down (SIT), number of syllables (DDK), max. JC velocity up (RP), pronoun rate (PD), max. LL jerk up (PD), max. JC velocity down (PD), mean JC speed (SBC), max. F0 (SIT), mean LL speed (SIT), max. JC velocity down (DDK), mean LL jerk (DDK), max. LL speed (SBC), and/or mean mouth symmetry ratio (RP).
18. The system of clause 1, wherein the remotely collected multimodal digital markers are extracted using a structured conversational dialog with a virtual agent.
19. The system of clause 1, wherein the external gold standard is Revised Amyotrophic Lateral Sclerosis Functional Rating Scale (ALSFRS-R).
20. The system of clause 1, wherein the sensitivity determination logic is further configured to determine which of the identified subset of the multimodal digital markers are clinically meaningful using a minimal clinically important difference (MCID) parameter.

Clause Set 4
1. A computer-implemented method of generating interpretable, composite marker indexes that are discriminative and noise-robust, including:

storing remotely collected multimodal digital markers from a first cohort and a second cohort;

using hierarchical clustering to group multicollinear features in the multimodal digital markers into clusters, and then selecting representative features for the clusters based on receiver operating characteristic (ROC) analyses for multiple classification tasks that require discrimination between the first cohort and the second cohort; and linearly combining the representative features into an interpretable, composite marker index such that relative contributions of each of the representative features to the interpretable, composite marker index are known.

2. The method of clause 1, furthering including linearly combining the representative features using Youden Index Optimization.

3. The method of clause 1, furthering including linearly combining the representative features using Fisher's Linear Discriminant Function.

4. The method of clause 1, furthering including linearly combining the representative features using Logistic Regression.

5. The method of clause 1, wherein the first cohort is healthy controls (CON), and the second cohort is all people with ALS (pALS).

6. The method of clause 1, wherein the first cohort is healthy controls (CON), and the second cohort is sign symptomatic (BUL).

7. The method of clause 1, wherein the first cohort is healthy controls (CON), and the second cohort is sign pre-symptomatic (PRE).

8. The method of clause 1, wherein the first cohort is sign pre-symptomatic (PRE), and the second cohort is sign symptomatic (BUL).

9. The method of clause 1, wherein the first cohort is sign onset, and the second cohort is non-sign onset.

9A. The method of clause 1, further including selecting the representative features for the clusters based on redundancy analysis.

9B. The method of clause 1, furthering including linearly combining the representative features using linear discriminant analysis (LDA).

9C. The method of clause 1, wherein the first cohort is people with Schizophrenia, and the second cohort is controls.

10. A system including one or more processors coupled to memory, the memory loaded with computer instructions to generate interpretable, composite marker indexes that are discriminative and noise-robust, the instructions, when executed on the processors, implement actions comprising:

storing remotely collected multimodal digital markers from a first cohort and a second cohort;

using hierarchical clustering to group multicollinear features in the multimodal digital markers into clusters, and then selecting representative features for the clusters based on receiver operating characteristic (ROC) analyses for multiple classification tasks that require discrimination between the first cohort and the second cohort; and linearly combining the representative features into an interpretable, composite marker index such that relative contributions of each of the representative features to the interpretable, composite marker index are known.

11. The system of clause 10, further implementing actions comprising linearly combining the representative features using Youden Index Optimization.

12. The system of clause 10, further implementing actions comprising linearly combining the representative features using Fisher's Linear Discriminant Function.

13. The system of clause 10, further implementing actions comprising linearly combining the representative features using Logistic Regression.

14. The system of clause 10, wherein the first cohort is healthy controls (CON), and the second cohort is all people with ALS (pALS).

15. The system of clause 10, wherein the first cohort is healthy controls (CON), and the second cohort is sign symptomatic (BUL).

16. The system of clause 10, wherein the first cohort is healthy controls (CON), and the second cohort is sign pre-symptomatic (PRE).

17. The system of clause 10, wherein the first cohort is sign pre-symptomatic (PRE), and the second cohort is sign symptomatic (BUL).

18. The system of clause 10, wherein the first cohort is sign onset, and the second cohort is non-sign onset.

19. A non-transitory computer readable storage medium impressed with computer program instructions to generate interpretable, composite marker indexes that are discriminative and noise-robust, the instructions, when executed on a processor, implement a method comprising:

storing remotely collected multimodal digital markers from a first cohort and a second cohort;

using hierarchical clustering to group multicollinear features in the multimodal digital markers into clusters, and then selecting representative features for the clusters based on receiver operating characteristic (ROC) analyses for multiple classification tasks that require discrimination between the first cohort and the second cohort; and linearly combining the representative features into an interpretable, composite marker index such that relative contributions of each of the representative features to the interpretable, composite marker index are known.

20. The non-transitory computer readable storage medium of clause 19, implementing the method further comprising linearly combining the representative features using Youden Index Optimization, Fisher's Linear Discriminant Function, and/or Logistic Regression.

Clause Set 5

1. A computer-implemented method of generating interpretable, composite marker indexes that are discriminative and noise-robust, including:

storing remotely collected multimodal digital markers from a first cohort and a second cohort;

grouping multicollinear features in the multimodal digital markers into clusters, and then selecting representative features for the clusters for multiple classification tasks that require discrimination between the first cohort and the second cohort; and linearly combining the representative features into an interpretable, composite marker index such that relative contributions of each of the representative features to the interpretable, composite marker index are known.

2. The method of clause 1, furthering including using hierarchical clustering to group the multicollinear features in the multimodal digital markers into the clusters.
3. The method of clause 1, furthering including using non-hierarchical clustering to group the multicollinear features in the multimodal digital markers into the clusters.
4. The method of clause 1, furthering including selecting the representative features for the clusters based on receiver operating characteristic (ROC) analyses for the multiple classification tasks that require the discrimination between the first cohort and the second cohort.
5. The method of clause 1, furthering including selecting the representative features for the clusters based on redundancy analysis for the multiple classification tasks that require the discrimination between the first cohort and the second cohort.
6. The method of clause 1, furthering including linearly combining the representative features using Youden Index Optimization.
7. The method of clause 6, furthering including linearly combining the representative features using Fisher's Linear Discriminant Function.
8. The method of clause 7, furthering including linearly combining the representative features using Logistic Regression.
9. The method of clause 8, furthering including determining which between the Youden Index Optimization, the Fisher's Linear Discriminant Function, and the Logistic Regression produces a best linear combination of the representative features.
10. The method of clause 1, wherein the first cohort is healthy controls (CON), and the second cohort is all people with ALS (pALS), wherein the first cohort is healthy controls (CON), and the second cohort is sign symptomatic (BUL), wherein the first cohort is healthy controls (CON), and the second cohort is sign pre-symptomatic (PRE), and/or wherein the first cohort is sign onset, and the second cohort is non-sign onset.
11. The method of clause 1, furthering including linearly combining the representative features using linear discriminant analysis (LDA).
12. The method of clause 1, wherein the first cohort is people with Schizophrenia, and the second cohort is controls.
13. A system including one or more processors coupled to memory, the memory loaded with computer instructions to generate interpretable, composite marker indexes that are discriminative and noise-robust, the instructions, when executed on the processors, implement actions comprising:
storing remotely collected multimodal digital markers from a first cohort and a second cohort;
grouping multicollinear features in the multimodal digital markers into clusters, and then selecting representative features for the clusters for multiple classification tasks that require discrimination between the first cohort and the second cohort; and
linearly combining the representative features into an interpretable, composite marker index such that relative contributions of each of the representative features to the interpretable, composite marker index are known.
14. The system of clause 13, further implementing actions comprising using hierarchical clustering and/or non-hierarchical clustering to group the multicollinear features in the multimodal digital markers into the clusters.
15. The system of clause 14, further implementing actions comprising selecting the representative features for the clusters based on receiver operating characteristic (ROC) analyses and/or redundancy analysis for the multiple classification tasks that require the discrimination between the first cohort and the second cohort.
16. The system of clause 15, further implementing actions comprising linearly combining the representative features using Youden Index Optimization, Fisher's Linear Discriminant Function, and/or Logistic Regression.
17. The system of clause 16, furthering including determining which between the Youden Index Optimization, the Fisher's Linear Discriminant Function, and the Logistic Regression produces a best linear combination of the representative features.
18. The system of clause 13, wherein the first cohort is healthy controls (CON), and the second cohort is all people with ALS (pALS), wherein the first cohort is healthy controls (CON), and the second cohort is sign symptomatic (BUL), wherein the first cohort is healthy controls (CON), and the second cohort is sign pre-symptomatic (PRE), and/or wherein the first cohort is sign onset, and the second cohort is non-sign onset.
19. The system of clause 13, wherein the first cohort is people with Schizophrenia, and the second cohort is controls.
20. A non-transitory computer readable storage medium impressed with computer program instructions to generate interpretable, composite marker indexes that are discriminative and noise-robust, the instructions, when executed on a processor, implement a method comprising:
storing remotely collected multimodal digital markers from a first cohort and a second cohort;
grouping multicollinear features in the multimodal digital markers into clusters, and then selecting representative features for the clusters for multiple classification tasks that require discrimination between the first cohort and the second cohort; and
linearly combining the representative features into an interpretable, composite marker index such that relative contributions of each of the representative features to the interpretable, composite marker index are known.

What is claimed is:
1. A computer-implemented method, executed on a processor-based system for generating interpretable, composite marker indexes that are discriminative and noise-robust, including:
storing multimodal digital markers remotely collected through structured dialog tasks from a first cohort and a second cohort;
grouping multicollinear features in the multimodal digital markers into clusters, and then selecting representative features for the clusters for multiple classification tasks that require discrimination between the first cohort and the second cohort;
linearly combining the representative features to generate an interpretable, composite marker index using a statistically interpretable model, wherein the composite marker index is optimized and wherein the relative contribution of each representative feature to the composite marker index is explicitly quantified; and generating, via the processor-based system, an actionable output comprising the composite marker index and corresponding interpretability metrics, and outputting the same for display, integration with clinical systems, or longitudinal condition tracking.

2. The method of claim 1, further including using hierarchical clustering to group the multicollinear features in the multimodal digital markers into the clusters.

3. The method of claim 1, further including using non-hierarchical clustering to group the multicollinear features in the multimodal digital markers into the clusters.

4. The method of claim 1, further including selecting the representative features for the clusters based on receiver operating characteristic (ROC) analyses for the multiple classification tasks that require the discrimination between the first cohort and the second cohort.

5. The method of claim 1, further including selecting the representative features for the clusters based on redundancy analysis for the multiple classification tasks that require the discrimination between the first cohort and the second cohort.

6. The method of claim 1, further including linearly combining the representative features using Youden Index Optimization.

7. The method of claim 6, further including linearly combining the representative features using Fisher's Linear Discriminant Function.

8. The method of claim 7, further including linearly combining the representative features using Logistic Regression.

9. The method of claim 8, further including determining which between the Youden Index Optimization, the Fisher's Linear Discriminant Function, and the Logistic Regression produces a best linear combination of the representative features.

10. The method of claim 1, wherein the first cohort is healthy controls (CON), and the second cohort is all people with ALS (pALS), wherein the first cohort is healthy controls (CON), and the second cohort is sign symptomatic (BUL), wherein the first cohort is healthy controls (CON), and the second cohort is sign pre-symptomatic (PRE), and/or wherein the first cohort is sign onset, and the second cohort is non-sign onset.

11. The method of claim 1, further including linearly combining the representative features using linear discriminant analysis (LDA).

12. The method of claim 1, wherein the first cohort is people with Schizophrenia, and the second cohort is controls.

13. A system including one or more processors coupled to memory, the memory loaded with computer instructions to generate interpretable, composite marker indexes that are discriminative and noise-robust, the instructions, when executed on the processors, implement actions comprising:
storing multimodal digital markers remotely collected through structured dialog tasks from a first cohort and a second cohort;
grouping multicollinear features in the multimodal digital markers into clusters, and then selecting representative features for the clusters for multiple classification tasks that require discrimination between the first cohort and the second cohort;
linearly combining the representative features to generate an interpretable, composite marker index using a statistically interpretable model, wherein the composite marker index is optimized and wherein the relative contribution of each representative feature to the composite marker index is explicitly quantified; and
generating, via the processor-based system, an actionable output comprising the composite marker index and corresponding interpretability metrics, and outputting the same for display, integration with clinical systems, or longitudinal condition tracking.

14. The system of claim 13, further implementing actions comprising using hierarchical clustering and/or non-hierarchical clustering to group the multicollinear features in the multimodal digital markers into the clusters.

15. The system of claim 14, further implementing actions comprising selecting the representative features for the clusters based on receiver operating characteristic (ROC) analyses and/or redundancy analysis for the multiple classification tasks that require the discrimination between the first cohort and the second cohort.

16. The system of claim 15, further implementing actions comprising linearly combining the representative features using Youden Index Optimization, Fisher's Linear Discriminant Function, and/or Logistic Regression.

17. The system of claim 16, further including determining which between the Youden Index Optimization, the Fisher's Linear Discriminant Function, and the Logistic Regression produces a best linear combination of the representative features.

18. The system of claim 13, wherein the first cohort is healthy controls (CON), and the second cohort is all people with ALS (pALS), wherein the first cohort is healthy controls (CON), and the second cohort is sign symptomatic (BUL), wherein the first cohort is healthy controls (CON), and the second cohort is sign pre-symptomatic (PRE), and/or wherein the first cohort is sign onset, and the second cohort is non-sign onset.

19. The system of claim 13, wherein the first cohort is people with Schizophrenia, and the second cohort is controls.

20. A non-transitory computer readable storage medium impressed with computer program instructions to generate interpretable, composite marker indexes that are discriminative and noise-robust, the instructions, when executed on a processor, implement a method comprising:
storing multimodal digital markers remotely collected through structured dialog tasks from a first cohort and a second cohort;
grouping multicollinear features in the multimodal digital markers into clusters, and then selecting representative features for the clusters for multiple classification tasks that require discrimination between the first cohort and the second cohort;
linearly combining the representative features into an interpretable, composite marker index using a statistically interpretable model, wherein the composite marker index is optimized and wherein the relative contribution of each representative feature to the composite marker index is explicitly quantified; and
generating, via the processor-based system, an actionable output comprising the composite marker index and corresponding interpretability metrics, and outputting the same for display, integration with clinical systems, or longitudinal condition tracking.

* * * * *